(12) United States Patent
Orimoto et al.

(10) Patent No.: US 11,084,815 B2
(45) Date of Patent: Aug. 10, 2021

(54) HETEROCYCLIC COMPOUND AND HARMFUL ARTHROPOD CONTROLLING AGENT CONTAINING SAME

(71) Applicant: Sumitomo Chemical Company, Limited, Tokyo (JP)

(72) Inventors: Kohei Orimoto, Takarazuka (JP); Naoya Sugimoto, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/650,433

(22) PCT Filed: Sep. 25, 2018

(86) PCT No.: PCT/JP2018/035302
§ 371 (c)(1),
(2) Date: Mar. 25, 2020

(87) PCT Pub. No.: WO2019/065570
PCT Pub. Date: Apr. 4, 2019

(65) Prior Publication Data
US 2020/0231587 A1    Jul. 23, 2020

(30) Foreign Application Priority Data
Sep. 26, 2017 (JP) ............... JP2017-184465

(51) Int. Cl.
*C07D 471/04* (2006.01)
*A01N 43/90* (2006.01)

(52) U.S. Cl.
CPC ........... *C07D 471/04* (2013.01); *A01N 43/90* (2013.01)

(58) Field of Classification Search
CPC ....... A01N 43/90; A01N 47/02; C07D 471/04
See application file for complete search history.

(56) References Cited

U.S. PATENT DOCUMENTS

| | | | |
|---|---|---|---|
| 5,599,832 A | 2/1997 | Gange | |
| 2010/0184598 A1 | 7/2010 | Selles et al. | |
| 2017/0305896 A1 | 10/2017 | Tanabe et al. | |

(Continued)

FOREIGN PATENT DOCUMENTS

| | | | |
|---|---|---|---|
| EP | 697172 A1 | 2/1996 | |
| EP | 3730494 A1 | 10/2020 | |
| JP | H08119807 A | 5/1996 | |

(Continued)

OTHER PUBLICATIONS

English Translation of International Search Report dated Dec. 25, 2018 in International Application No. PCT/JP2018/035302.

English Translation of International Preliminary Report on Patentability dated Mar. 31, 2020 in International Application No. PCT/JP2018/035302.

Extended European Search Report dated Apr. 16, 2021 in EP Application No. 18863320.0.

Examination Report dated Jun. 15, 2021 in IN Application No. 202047016819.

*Primary Examiner* — Jianfeng Song

(74) *Attorney, Agent, or Firm* — Panitch Schwarze Belisario & Nadel LLP

(57) ABSTRACT

A composition containing a compound having excellent controlling effects against a harmful arthropod is represented by formula (I). In formula (I), Q represents a group represented by formula Q1; a group represented by formula Q2 or a group represented by formula Q3; a combination of $A^2$ and $A^3$ represents a combination in which $A^2$ is a nitrogen atom and $A^3$ is $CR^{4b}$, or a combination in which $A^2$ is $CR^{4a}$ and $A^3$ is a nitrogen atom; Z represents an oxygen atom or a sulfur atom; and T represents a C2-C10 chain hydrocarbon group having one or more halogen atoms.

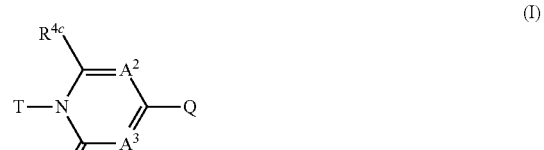

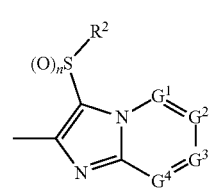

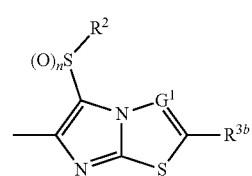

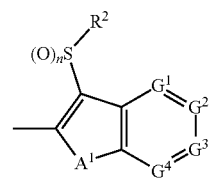

8 Claims, No Drawings

(56) References Cited

U.S. PATENT DOCUMENTS

2018/0022760 A1  1/2018  Kudo et al.
2019/0223436 A1  7/2019  Orimoto et al.

FOREIGN PATENT DOCUMENTS

| JP | 2002220377 A | 8/2002 | |
|----|---|---|---|
| JP | 2010525039 A | 7/2010 | |
| JP | 2018024672 A | 2/2018 | |
| WO | 2001068613 A1 | 9/2001 | |
| WO | 2015087458 A1 | 6/2015 | |
| WO | 2016052247 A1 | 4/2016 | |
| WO | WO-2016052247 A1 * | 4/2016 | ........... C07D 239/40 |
| WO | 2016129684 A1 | 8/2016 | |
| WO | 2017061497 A1 | 4/2017 | |
| WO | 2018052119 A1 | 3/2018 | |

* cited by examiner

HETEROCYCLIC COMPOUND AND HARMFUL ARTHROPOD CONTROLLING AGENT CONTAINING SAME

CROSS-REFERENCE TO RELATED APPLICATION

This application is a Section 371 of International Application No. PCT/JP2018/035302, filed Sep. 25, 2018, which was published in the Japanese language on Apr. 4, 2019 under International Publication No. WO 2019/065570 A1, which claims priority under 35 U.S.C. § 119(b) to Japanese Application No. 2017-184465, filed on Sep. 26, 2017, the disclosures of which are incorporated herein by reference in their entireties.

TECHNICAL FIELD

The present invention is related to a certain class of heterocyclic compound and an agent for controlling harmful arthropods comprising the same.

BACKGROUND ART

To date, in order to control harmful arthropods, some compounds have been developed and come into practical use.

Also, a certain class of compound has been known to have an effect on controlling pests (see Patent Document 1).

CITATION LIST

Patent Document

Patent Document 1: WO 2016/052247

SUMMARY OF THE INVENTION

Problems to be Solved by Invention

An object of the present invention is to provide a compound having an excellent efficacy for controlling harmful arthropods.

Means to Solve Problems

The present inventors have intensively studied to find compounds having an excellent efficacy for controlling harmful arthropods, and as a result, found that a compound represented by the below-mentioned formula (I) has an excellent efficacy for controlling harmful arthropods.

That is, the present invention includes the followings.
[1] A compound represented by formula (I):

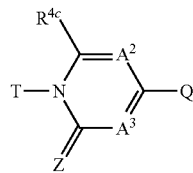

[wherein
Q represents a group represented by formula Q1, a group represented by formula Q2, or a group represented by formula Q3,

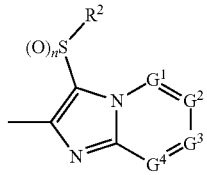

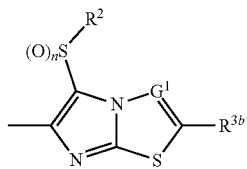

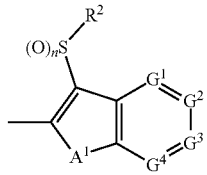

n is 0, 1 or 2,
$G^1$ represents a nitrogen atom or $CR^{3a}$,
$G^2$ represents a nitrogen atom or $CR^{3b}$,
$G^3$ represents a nitrogen atom or $CR^{3c}$,
$G^4$ represents a nitrogen atom or $CR^{3d}$,
$R^{3a}$, $R^{3b}$, $R^{3c}$ and $R^{3d}$ are identical to or different from each other and each represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five (5) or six (6) membered aromatic heterocyclic group optionally having one or more substituents selected from Group H, $OR^{12}$, $NR^{11}NR^{12}$, $NR^{11a}R^{12a}$, $NR^{24}NR^{11}R^{12}$, $NR^{24}OR^{11}$, $NR^{11}C(O) R^{13}$, $NR^{24}NR^{11}C(O) R^{13}$, $NR^{11}C(O) OR^{14}$, $NR^{24}NR^{11}C(O) OR^{14}$, $NR^{11}C(O) NR^{15x}R^{16x}$, $NR^{24}NR^{11}C(O) NR^{15x}R^{16x}$, $N=CHNR^{15x}R^{16x}$, $N=S(O)_pR^{15}R^{16}$, $C(O)R^{13}$, $C(O)OR^{17}$, $C(O)NR^{15x}R^{16x}$, $C(O)NR^{11}S(O)_2R^{23}$, $CR^{30}=NOR^{17}$, $NR^{11}CR^{24}=NOR^{17}$, a cyano group, a nitro group, a hydrogen atom, or a halogen atom,
p represents 0 or 1,
$A^1$ represents $NR^5$, an oxygen atom or a sulfur atom,
a combination of $A^2$ and $A^3$ represents a combination wherein $A^2$ represents a nitrogen atom and $A^3$ represents $CR^{4b}$; or a combination wherein $A^2$ represents $CR^{4a}$ and $A^3$ represents a nitrogen atom,
$R^{4a}$, $R^{4b}$ and $R^{4c}$ are identical to or different from each other and each represents a C1-C6 chain hydrocarbon group optionally having one or more halogen atoms, a nitro group, $OR^{18}$, $NR^{18}R^{19}$, a cyano group, a halogen atom, or a hydrogen atom,
Z represents an oxygen atom or a sulfur atom,
T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy)C2-C5 alkyl group having one or more halogen atoms, a (C3-C7 cycloalkyl)C1-C3 alkyl group having one or more substituents selected from Group G, a (C1-C5 alkyl)-S(O)$_m$—(C2-C5 alkyl) group having one or more halogen atoms, a (C3-C5 alkenyl)-S(O)$_m$—(C2-C5 alkyl) group having one or more halogen atoms, a (C3-C5 alkynyl)-S(O)$_m$—(C2-C5 alkyl) group having one or more halogen atoms, a (C1-C5 alkyl)-C(O)—(C1-C5 alkyl) group having one or more halogen atoms, a group represented by formula T-1, a group represented by formula T-2, a group represented by formula T-3, a group represented by formula T-4, a group represented by formula T-5, a group represented by formula T-6, a group represented by formula T-7, or a group represented by formula T-8,

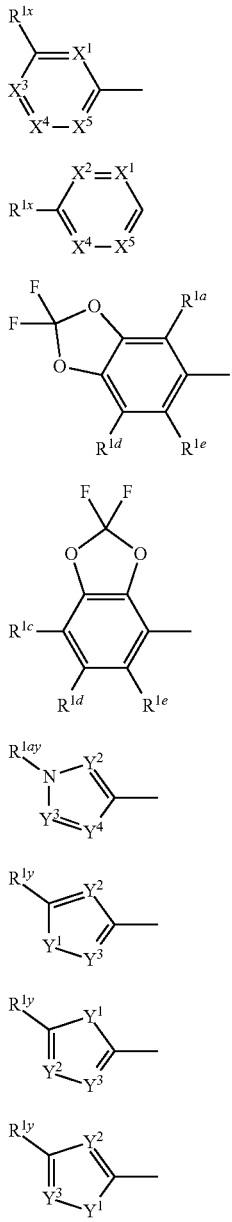

T-1

T-2

T-3

T-4

T-5

T-6

T-7

T-8

$X^1$ represents a nitrogen atom or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{1e}$,
$R^{1x}$ represents a C1-C5 chain hydrocarbon group having one or more halogen atoms, $OR^7$, $OS(O)_2R^7$, $S(O)_mR^7$, $NR^1R^{29}$, $NR^8S(O)_2R^7$, or a halogen atom, $R^{1a}$, $R^{1b}$, $R^{1c}$, $R^{1d}$ and $R^{1e}$ are identical to or different from each other and each represents a C1-C6 chain hydrocarbon group optionally having one or more halogen atoms, a C3-C6 cycloalkyl group optionally having one or more halogen atoms, a halogen atom, or a hydrogen atom,
$Y^1$ represents $NR^{25}$, an oxygen atom or a sulfur atom,
$Y^2$ represents a nitrogen atom, or $CR^{26}$,
$Y^3$ represents a nitrogen atom, or $CR^{27}$,
$Y^4$ represents a nitrogen atom, or $CR^{28}$,
$R^5$ and $R^{25}$ are identical to or different from each other and each represents a C1-C6 chain hydrocarbon group optionally having one or more halogen atoms, a C1-C6 alkoxy group optionally having one or more halogen atoms, a C3-C7 cycloalkyl group optionally having one or more halogens, a (C3-C7 cycloalkyl)C1-C6 alkyl group optionally having one or more halogens, or a hydrogen atom,
$R^{26}$, $R^{27}$, and $R^{28}$ are identical to or different from each other and each represents a C1-C6 chain hydrocarbon group optionally having one or more halogen atoms, a C3-C6 cycloalkyl group optionally having one or more halogen atoms, a halogen atom, or a hydrogen atom;
$R^{1y}$ represents a C1-C5 chain hydrocarbon group having one or more halogen atoms, $OR^7$, $OS(O)_2R^7$, $S(O)_mR^7$, $NR^8S(O)_2R^7$, a cyano group, or a halogen atom,
$R^{1ay}$ and $R^7$ are identical to or different from each other and each represents a C1-C6 chain hydrocarbon group having one or more halogen atoms,
$R^8$ represents a C1-C6 chain hydrocarbon group optionally having one or more halogen atoms, or a hydrogen atom,
m is 0, 1 or 2,
$R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G,
$R^2$ represents a C1-C6 alkyl group optionally having one or more halogens, a cyclopropyl group, or a cyclopropylmethyl group,
$R^{11}$, $R^{17}$, $R^{19}$, $R^{24}$, and $R^{29}$ are identical to or different from each other and each represents a C1-C6 chain hydrocarbon group optionally having one or more halogen atoms, or a hydrogen atom,
$R^{30}$ represents a C1-C6 chain hydrocarbon group optionally having one or more halogen atoms, an amino group, or a hydrogen atom,
$R^{18}$ represents a C1-C6 chain hydrocarbon group optionally having one or more halogen atoms,
$R^{12}$ represents a C1-C6 chain hydrocarbon group optionally having one or more halogen atoms, a C1-C6 alkyl group having one substituent selected from Group F, a C3-C7 cycloalkyl group optionally having one substituent selected from Group J, a C3-C7 cycloalkenyl group optionally having one substituent selected from Group J, a phenyl group, a six membered aromatic heterocyclic group {the phenyl group and the six membered aromatic heterocyclic group each independently may have optionally one or more substituents selected from Group D}, $S(O)_2R^{23}$, or a hydrogen atom,
$R^{23}$ represents a C1-C6 chain hydrocarbon group optionally having one or more halogen atoms, a C3-C7 cycloalkyl group optionally having one or more halogens, or a phenyl group optionally having one or more substituents selected from Group D, $R^{11a}$ and $R^{12a}$ combined together with a nitrogen atom to which they are attached represent a three (3) to seven (7) membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogens, a (C3-C6 cycloalkyl)C1-C3 alkyl group optionally having one or more halogens, a phenyl group optionally having one or more substituents selected from Group D, a five (5) or six (6) membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogens, a (C3-C6 cycloalkyl)C1-C3 alkyl group optionally having one or more halogens, or a phenyl C1-C3 alkyl group {the phenyl moiety in the phenyl C1-C3 alkyl group may have optionally one or more substituents selected from Group D}, $R^{15}$ and $R^{16}$ are identical to or different from each other and each represents a C1-C6 alkyl group optionally having one or more halogens, $R^{15x}$ represents a C1-C6 alkyl group optionally having one or more halogens, or a hydrogen atom, $R^{16x}$ represents a C1-C6 chain hydrocarbon group optionally having one or more substituents selected from Group F, a C3-C7 cycloalkyl group optionally having one substituent selected from Group J, or a hydrogen atom, Group B: a group consisting of a C1-C6 alkoxy group optionally having one or more halogens, a C3-C6 alkenyloxy group optionally having one or more halogens, a C3-C6 alkynyloxy group optionally having one or more halogens, a C1-C6 alkylsulfanyl group optionally having one or more halogens, a C1-C6 alkylsulfinyl group optionally having one or more halogens, a C1-C6 alkylsulfonyl group optionally having one or more halogens, a C3-C6 cycloalkyl group optionally having one or more halogen atoms, a cyano group, a hydroxy group, and a halogen atom, Group C: a group consisting of a C1-C6 chain hydrocarbon group optionally having one or more halogen atoms, a C1-C6 alkoxy group optionally having one or more halogens, a C3-C6 alkenyloxy group optionally having one or more halogens, a C3-C6 alkynyloxy group optionally having one or more halogens, and a halogen atom, Group D: a group consisting of a C1-C6 chain hydrocarbon group optionally having one or more halogen atoms, a hydroxy group, a C1-C6 alkoxy group optionally having one or more halogens, a C3-C6 alkenyloxy group optionally having one or more halogens, a C3-C6 alkynyloxy group optionally having one or more halogens, a sulfanyl group, a C1-C6 alkylsulfanyl group optionally having one or more halogens, a C1-C6 alkylsulfinyl group optionally having one or more halogens, a C1-C6 alkylsulfonyl group optionally having one or more halogens, an amino group, $NHR^{21}$, $NR^{21}R^{22}$, $C(O)R^{21}$, $OC(O) R^{21}$, $C(O)OR^{21}$, a cyano group, a nitro group, and a halogen atom, $R^{21}$ and $R^{22}$ are identical to or different from each other and each represents a C1-C6 alkyl group optionally having one or more halogens, Group E: a group consisting of a C1-C6 chain hydrocarbon group optionally having one or more halogen atoms, a C1-C6 alkoxy group optionally having one or more halogens, a C3-C6 alkenyloxy group optionally having one or more halogens, a C3-C6 alkynyloxy group optionally having one or more halogens, a halogen atom, an oxo group, a hydroxy group, a cyano group, and a nitro group, Group F: a group consisting of a C1-C6 alkoxy group optionally having one or more halogens, a phenyl group optionally having one or more substituents selected from Group D, a five (5) or six (6) membered aromatic heterocyclic group optionally having one or more substituents selected from Group D, a C3-C7 cycloalkyl group optionally having one or more halogens, a three (3) to seven (7) membered nonaromatic heterocyclic group optionally having one or more substituents selected from Group C, an amino group, $NHR^{21}$, $NR^{21}R^{22}$, and a cyano group, Group G: a group consisting of a halogen atom and a C1-C6 haloalkyl group, Group H: a group consisting of a C1-C6 alkyl group optionally having one or more halogens, $OR^{10}$, $NR^9R^{10}$, $C(O)R^{10}$, $C(O)NR^9R^{10}$, $OC(O)R^9$, $CC(O)OR^9$, $NR^{10}C(O) R^9$, $NR^{10}C(O)$ $OR^9$, $C(O)OR^{10}$, a halogen atom, a nitro group, a cyano group, an amino group, and a five (b) or six (6) membered aromatic heterocyclic group, $R^9$ represents a C1-C6 alkyl group optionally having one or more halogens, or a C3-C6 cycloalkyl group optionally having one or more halogen atoms, $R^{10}$ represents a C1-C6 alkyl group optionally having one or more halogens, a C3-C6 cycloalkyl group optionally having one or more halogen atoms, or a hydrogen atom, Group J: a group consisting of a C1-C6 alkyl group optionally having one or more halogens, a halogen atom, and a cyano group]

(hereinafter, referred to as "Present compound" or "Compound of the present invention").

[2] The compound according to [1] wherein Q represents a group represented by formula Q1, or a group represented by formula Q2.

[3] The compound according to [1] wherein Q represents a group represented by formula Q1.

[4] The compound according to any one of [1] to [3] wherein $A^2$ represents a nitrogen atom, and $A^3$ represents $CR^{4b}$.

[5] The compound according to any one of [1] to [4] wherein T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy)C2-C5 alkyl group having one or more halogen atoms, a (C3-C7 cycloalkyl)C1-C3 alkyl group having one or more substituents selected from Group G, a group represented by formula T-1, a group represented by formula T-2, a group represented by formula T-5, a group represented by formula T-6, a group represented by formula T-7, or a group represented by formula T-8, $R^{1x}$, $R^{1y}$ and $R^{1ay}$ are identical to or different from each other and each represents a C1-C5 chain hydrocarbon group having one or more halogen atoms.

[6] The compound according to any one of [1] to [4] wherein T represents a C2-C10 chain hydrocarbon group having one or more halogen atoms.

[7] The compound according to any one of [1] to [4] wherein T represents a C2-C10 alkyl group having three or more fluorine atoms.

[8] The compound according to any one of [1] to [7] wherein $R^{3a}$, $R^{3b}$, $R^{3c}$, and $R^{3d}$ are identical to or different from each other and each represents a C1-C6 alkyl group, a C3-C7 cycloalkyl group {the C1-C6 alkyl group and the C3-C7 cycloalkyl group each independently may have optionally one or more substituents selected from a group consisting of halogen atom and cyano group}, a phenyl group, a pyridyl group, a pyrimidinyl group {the phenyl group, the pyridyl group, and the pyrimidinyl group each independently may have optionally one or more substituents selected from Group J}, $OR^{12}$, $CR^{30}=NOR^{17}$, a hydrogen atom, or a halogen atom, $R^{4a}$, $R^{4b}$ and $R^{4c}$ are identical to or different from each other and each represents a C1-C3 alkyl group, a C1-C3 alkoxy group, a cyano group, a halogen atom, or a hydrogen atom. [9] The compound according to any one of [1] to [7] wherein $G^1$ represents a nitrogen atom or CH, $G^2$ represents $CR^{3b}$, $G^3$ represents $CR^{3c}$, $G^4$ represents CH, $R^{3b}$ and $R^{3c}$ are identical to or different from each other and each represents a C1-C6 alkyl group, a C3-C7 cycloalkyl group {the C1-C6 alkyl group and the C3-C7 cycloalkyl group each independently may have optionally one or more substituents selected from a group consisting of halogen atom and cyano group}, $OR^{12}$, a hydrogen atom, or a halogen atom, and $R^{4a}$, $R^{4b}$ and $R^{4c}$ represent a hydrogen atom.

[10] The compound according to any one of [1] to [7] wherein $G^1$ represents a nitrogen atom or CH, $G^2$ represents $CR^{3b}$, $G^3$ represents $CR^{3c}$, $G^4$ represents CH, and $R^{3b}$ and $R^{3c}$ each independently represents a C1-C6 alkyl group optionally having one or more halogens, or a hydrogen atom.

[11] The compound according to any one of [1] to [10] wherein $R^2$ represents an ethyl group.

[12] A composition for controlling harmful arthropod which comprises the compound according to any one of [1] to [11] and an inert carrier.

[13] A method for controlling harmful arthropod which comprises applying an effective amount of the compound according to any one of [1] to [11] to a harmful arthropod or a habitat where a harmful arthropod lives.

[14] A composition comprising one or more ingredients selected from the group consisting of the following Groups (a) and (b) and the compound according to any one of [1] to [11] (hereinafter, referred to as "Present Composition"):

Group (a): a group consisting of insecticidal ingredients, miticidal ingredients, and nematicidal ingredients; and Group (b): fungicidal ingredients.

Effect of Invention

The present invention can control harmful arthropod.

MODE FOR CARRYING OUT THE INVENTION

The substituent(s) as described herein is/are explained.

The term "halogen atom" represents fluorine atom, chlorine atom, bromine atom, or iodine atom.

When the substituents have two or more halogen atoms, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, hexyl group, octyl group, nonyl group, and decyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, 5-hexenyl group, 7-octenyl group, nonenyl group, and decenyl group.

Example of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, 7-octynyl group, nonynyl group, and decynyl group.

The term of "alkoxy group" represents a monovalent group in which the alkyl group binds to an oxygen atom, and includes, for example, methoxy group, ethoxy group, propoxy group, butoxy group, pentoxy group, and hexyloxy group.

The term of "alkenyloxy group" represents a monovalent group in which the alkenyl group binds to an oxygen atom, and includes, for example, vinyloxy group, 1-propenyloxy group, 1-bunyloxy group, 1-pentenyloxy group, and 1-hexenyloxy group.

The term of "alkynyloxy group" represents a monovalent group in which the above-mentioned alkynyl group binds to an oxygen atom, and ethynyloxy group, 1-propynyloxy group, 1-butynyloxy group, 1-pentynyloxy group, and 1-hexynyloxy group.

Examples of "haloalkyl group" include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, perfluorohexyl group, perfluoroocthyl group, perfluorononyl group, and perfluorodecyl group.

Examples of "C1-C5 chain hydrocarbon group having one or more halogen atoms", "C1-C6 chain hydrocarbon group having one or more halogen atoms", "C2-C5 chain hydrocarbon group having one or more halogen atoms", "C2-C10 chain hydrocarbon group having one or more halogen atoms", and "C1-C10 chain hydrocarbon group having one or more halogen atoms" include 2,2,3,3,3-pentafluoropropyl group, 2,2,3,3-tetrafluoropropyl group, 2,2,3,4,4,4-hexafluorobutyl group, 2,2,3,3,4,4,4-heptafluorobutyl group, and also include perfluoroalkyl group.

Examples of "cycloalkyl group" include cyclopropyl group, cyclobutyl group, cyclopentyl group, cyclohexyl group, and cycloheptyl group.

Examples of "cycloalkenyl group" include cyclopropenyl group, cyclobutenyl group, cyclopentenyl group, cyclohexenyl group, and cycloheptenyl group.

Examples of "C3-C6 cycloalkyl group optionally having one or more halogen atoms", and "C3-C7 cycloalkyl group optionally having one or more halogens" include 2-fluorocyclopropyl group.

Examples of "three (3) to seven (7) membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the three (3) to seven (7) membered nonaromatic heterocyclic group optionally having one or more substituents selected from Group E include the followings:

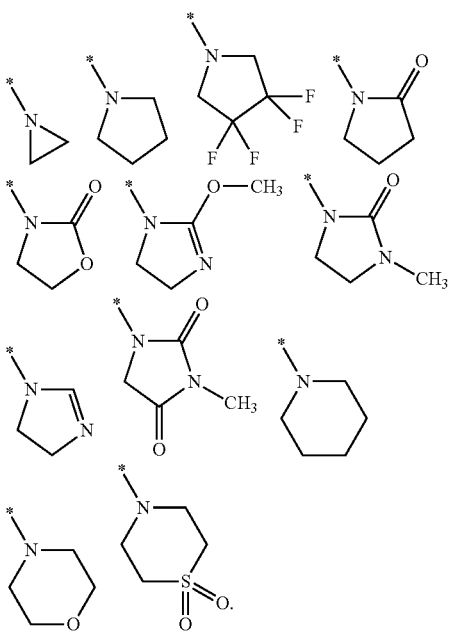

The term of "(C1-C5 alkoxy)C2-C5 alkyl group having one or more halogen atoms" represents a group in which the (C1-C5 alkoxy) and/or the (C2-C5 alkyl) has/have one or more halogen atoms, and includes, for example, 2-(trifluoromethoxy)ethyl group, 2,2-difluro-3-methoxypropyl group, 2,2-difluoro-3-(2,2,2-trifluoroethoxy)propyl group, and 3-(2-chloroethoxy)propyl group.

The term of "(C3-C5 alkenyloxy)C2-C5 alkyl group having one or more halogen atoms" represents a group in which the (C3-C5 alkenyloxy) and/or the (C2-C5 alkyl) has/have one or more halogen atoms, and includes, for example, 2-(2-trifluoro-1-propenyloxy)ethyl group, 3-(1-propenyloxy)-2,2-difluoropropyl group, and 3-(3-chloro-1-propenyloxy)propyl group. The term of "a (C3-C5 alkynyloxy)C2-C5 alkyl group having one or more halogen atoms" represents a group in which the (C3-C5 alkynyloxy) and/or the (C2-C5 alkyl) has/have one or more halogen atoms, and includes, for example, 2-(2-trifluoro-1-propynyloxy)ethyl group, 3-(1-propynyloxy)-2,2-difluoropropyl group, and 3-(3-chloro-1-propynyloxy)propyl group.

The terms of "alkylsulfanyl group", "alkylsulfinyl group" and "alkylsulfonyl group" represent an alkyl group containing a S(O)$_m$ moiety, respectively.

For example, examples of the "alkylsulfanyl" when m is 0 include methylsulfanyl group, ethylsulfanyl group, propylsulfanyl group, and isopropylsulfanyl group.

For example, examples of the "alkylsulfinyl" when m is 1 include methylsulfinyl group, ethylsulfinyl group, propylsulfinyl group, and isopropylsulfinyl group.

For example, examples of the "alkylsulfonyl" when m is 2 include methylsulfonyl group, ethylsulfonyl group, propylsulfonyl group, and isopropylsulfonyl group.

The term of "(C1-C5 alkylsulfanyl)C2-C5 alkyl group having one or more halogen atom" represents a group in which the (C1-C5 alkylsulfanyl) and/or the (C2-C5 alkyl) has/have one or more halogen atoms, and includes, for example, 2,2-difluoro-2-(trifluoromethylthio)ethyl group.

The term of "(C1-C5 alkylsulfinyl)C2-C5 alkyl group having one or more halogen atoms" represents a group in which the (C1-C5 alkylsulfinyl) and/or the (C2-C5 alkyl) has/have one or more halogen atoms, and includes, for example, 2,2-difluoro-2-(trifluoromethansulfinyl)ethyl group.

The term of "(C1-C5 alkylsulfonyl)C2-C5 alkyl group having one or more halogen atoms" represents a group in which the (C1-C5 alkylsulfonyl) and/or the (C2-C5 alkyl) has/have one or more halogen atoms, and includes, for example, 2,2-difluro-2-(trifluoromethansulfonyl)ethyl group.

The term of "(C3-C5 alkenylsulfanyl)C2-C5 alkyl group having one or more halogen atoms" represents a group in which the (C3-C5 alkenylsulfanyl) and/or the (C2-C5 alkyl) has/have one or more halogen atoms, and includes, for example, 2,2-difluoro-2-(3-trifluoro-1-propenylthio)ethyl group.

The term of "(C3-C5 alkenylsulfinyl)C2-C5 alkyl group having one or more halogen atoms" represents a group in which the (C3-C5 alkenylsulfinyl) and/or the (C2-C5 alkyl) has/have one or more halogen atoms, and includes, for example, 2,2-difluoro-2-(3-trifluoro-1-propenesulfinyl)ethyl group.

The term of "(C3-C5 alkenylsulfonyl)C2-C5 alkyl group having one or more halogen atoms" represents a group in which the (C3-C5 alkenylsulfonyl) and/or the (C2-C5 alkyl) has/have one or more halogen atoms, and includes, for example, 2,2-difluoro-2-(3-trifluoro-1-propenesulfonyl) ethyl group.

The term of "(C3-C5 alkynylsulfanyl)C2-C5 alkyl group having one or more halogen atoms" represents a group in which the (C3-C5 alkynylsulfanyl) and/or the (C2-C5 alkyl) has/have one or more halogen atoms, and includes, for example, 2,2-difluoro-2-(3-trifluoro-1-propynylthio)ethyl group.

The term of "(C3-C5 alkynylsulfinyl)C2-C5 alkyl group having one or more halogen atoms" represents a group in which the (C3-C5 alkynylsulfinyl) and/or the (C2-C5 alkyl) has/have one or more halogen atoms, and include, for example, 2,2-difluoro-2-(3-trifluoro-1-propynesulfinyl)ethyl group.

The term of "(C3-C5 alkynylsulfonyl)C2-C5 alkyl group having one or more halogen atoms" represents a group in which the (C3-C5 alkynylsulfonyl) and/or the (C2-C5 alkyl) has/have one or more halogen atoms, and includes, for example, 2,2-difluoro-2-(3-trifluoro-1-propynesulfonyl) ethyl group.

Examples of "(C1-C5 alkyl)-C(O)—(C1-C5 alkyl) group having one or more halogen atoms" include trifluoroacetyl-methyl group.

The term of "(C3-C7 cycloalkyl)C1-C6 alkyl group optionally having one or more halogens" represents a group in which the (C3-C7 cycloalkyl) and/or the (C1-C6 alkyl) may have optionally one or more halogens, and includes, for example, (2,2-difluorocyclopropyl)methyl group, 2-cyclopropyl-1,1,2,2-tetrafluoroethyl group, 2-(2,2-difluorocyclopropyl)-1,1,2,2-tetrafluoroethyl group, (2,2-difluorocyclopropyl)propyl group, (2,2-difluorocyclopropyl)butyl group, (2,2-difluorccyclopropyl)pentyl group, and (2,2-difluorocyclopropyl)hexyl group.

Examples of "C3-C7 cycloalkyl group having one or more substituents selected from Group G" include 2,2-difluorocyclopropyl group.

The term of "(C3-C7 cycloalkyl)C1-C3 alkyl group having one or more substituents selected from Group G" represents a group in which the (C3-C7 cyclopropyl) and/or the (C1-C3 alkyl) has/have one or more substituents selected from Group G, and include, for example, (2,2-difluorocyclopropyl)methyl group, [1-(trifluoromethyl)cyclopropyl]

methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

Examples of "phenyl C1-C3 alkyl group {the phenyl moiety in the phenyl C1-C3 alkyl group may have optionally one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "five (5) or six (6) membered aromatic heterocyclic group" represents five (5) membered aromatic heterocyclic group or six (6) membered aromatic heterocyclic group, and examples of the five (5) membered aromatic heterocyclic group include pyrrolyl group, furyl group, thienyl group, pyrazolyl group, imidazolyl group, triazolyl group, tetrazolyl group, oxazclyl group, isoxazolyl group, thiazolyl group, isothiazolyl group, oxadiazolyl group, and thiadiazolyl group. Examples of six (6) membered aromatic heterocyclic group include pyridyl group, pyridazinyl group, pyrimidinyl group, pyrazinyl group, and triazinyl group.

Examples of the embodiment of the compound of the present invention include the followings.

[Embodiment 1] A compound of the present invention where Q represents a group represented by formula Q1 or a group represented by formula Q2.

[Embodiment 2] A compound of the present invention where Q represents a group represented by formula Q1.

[Embodiment 3] The compound according to the Embodiment 2 wherein $R^2$ represents a C1-C6 alkyl group, and $R^{3a}$, $R^{3b}$, $R^{3c}$ and $R^{3d}$ are identical to or different from each other and each represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may have optionally one or more substituents selected from Group J}, $OR^{12}$, $NR^{11}R^{12}$, $NR^{11a}R^{12a}$, $C(O) NR^{15x}R^{16x}$, $CR^{30}=NOR^{17}$, a hydrogen atom, or a halogen atom.

[Embodiment 4] The compound according to embodiment 2 wherein $R^2$ represents a C1-C6 alkyl group, $R^{3a}$, $R^{3b}$, $R^{3c}$ and $R^{3d}$ are identical to or different from each other and each represents, a C1-C6 alkyl group, a C3-C7 cycloalkyl group {the C1-C6 alkyl group and the C3-C7 cycloalkyl group each independently may have one or more substituents selected from a group consisting of halogen atom and cyano group}, a phenyl group, a pyridyl group, a pyrimidinyl group {the phenyl group, the pyridyl group, and the pyrimidinyl group each independently may have optionally one or more substituents selected from Group J}, $OR^{12}$, $CR^{30}=NOR^{17}$, a hydrogen atom, or a halogen atom, $R^{4a}$, $R^{4b}$ and $R^{4c}$ are identical to or different from each other and each represents a C1-C3 alkyl group, a C1-C3 alkoxy group, a cyano group, a halogen atom, or a hydrogen atom.

[Embodiment 5] The compound according to embodiment 2 wherein $R^2$ represents an ethyl group, $R^{3a}$, $R^{3b}$, $R^{3c}$ and $R^{3d}$ are identical to or different from each other and each represents a C1-C6 alkyl group, a C3-C7 cycloalkyl group {the C1-C6 alkyl group and the C3-C7 cycloalkyl group each independently may have optionally one or more substituents selected from a group consisting of halogen atom and cyano group}, a phenyl group, a pyridyl group, a pyrimidinyl group {the phenyl group, the pyridyl group, and the pyrimidinyl group each independently may have optionally one or more substituents selected from Group J}, $OR^{12}$, $CR^{30}=NOR^{17}$, a hydrogen atom, or a halogen atom, $R^{4a}$, $R^{4b}$ and $R^{4c}$ represent a hydrogen atom.

[Embodiment 6] The compound according to embodiment 5 wherein $G^1$ represents a nitrogen atom or CH, $G^2$ represents $CR^{3b}$, $G^3$ represents $CR^{3c}$, $G^4$ represents CH, and $R^{3b}$ and $R^{3c}$ are identical to or different from each other and each represents a C1-C6 alkyl group, a C3-C7 cycloalkyl group {the C1-C6 alkyl group and the C3-C7 cycloalkyl group each independently may have optionally one or more substituents selected from a group consisting of halogen atom and cyano group}, $OR^{12}$, a hydrogen atom, or a halogen atom.

[Embodiment 7] The compound according to embodiment 6 wherein $G^1$ represents a nitrogen atom,

[Embodiment 8] The compound according to embodiment 6 wherein $G^1$ represents CH.

[Embodiment 9] The compound according to embodiment 5 wherein $G^1$ represents a nitrogen atom or CH, $G^2$ represents $CR^{3b}$, $G^3$ represents $CR^{3c}$, $G^4$ represents CH, $R^{3b}$ and $R^{3c}$ are identical to or different from each other and each represents a C1-C6 alkyl group optionally having one or more halogens, or a hydrogen atom.

[Embodiment 10] The compound according to embodiment 9 wherein $G^1$ represents a nitrogen atom.

[Embodiment 11] The compound according to embodiment 9 wherein $G^1$ represents CH.

[Embodiment 12] A compound of the present invention wherein Q represents a group represented by formula $Q^2$, $R^2$ represents a C1-C6 alkyl group, $R^{3a}$ and $R^{3b}$ are identical to or different from each other and each represents a C1-C6 alkyl group, a C3-C7 cycloalkyl group {the C1-C6 alkyl group and the C3-C7 cycloalkyl group each independently may have optionally one or more substituents selected from a group consisting of halogen atom and cyano group}, a phenyl group, a pyridyl group, a pyrimidinyl group {the phenyl group, the pyridyl group, and the pyrimidinyl group each may have optionally one or more substituents selected from Group J}, $OR^{12}$, $CR^{30}=NOR^{17}$, a hydrogen atom, or a halogen atom, $R^{4a}$, $R^{4b}$ and $R^{4c}$ are identical to or different from each other and each represents a C1-C3 alkyl group, a C1-C3 alkoxy group, a cyano group, a halogen atom, or a hydrogen atom.

[Embodiment 13] The compound according to embodiment 12 wherein $R^2$ represents an ethyl group, and $R^{4a}$, $R^{4b}$ and $R^{4c}$ represent a hydrogen atom.

[Embodiment 14] The compound according to embodiment 13 wherein $G^1$ represents a nitrogen atom or CH, $R^{3b}$ represents a C1-C6 alkyl group, a C3-C7 cycloalkyl group {the C1-C6 alkyl group and the C3-C7 cycloalkyl group each independently may have optionally one or more substituents selected from a group consisting of halogen atom and cyano group}, $OR^{12}$, a hydrogen atom, or a halogen atom.

[Embodiment 15] The compound according to embodiment 14 wherein $G^1$ represents a nitrogen atom.

[Embodiment 16] The compound according to embodiment 14 wherein $G^1$ represents CH.

[Embodiment 17] The compound according to embodiment 13 wherein $G^1$ represents a nitrogen atom or CH, and $R^{3b}$ represents a C1-C6 alkyl group optionally having one or more halogens, or a hydrogen atom.

[Embodiment 18] The compound according to embodiment 17 wherein $G^1$ represents a nitrogen atom.

[Embodiment 19] The compound according to embodiment 17 wherein $G^1$ represents CH.

[Embodiment 20] A compound of the present invention wherein T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy)C2-C5 alkyl group having one or more halogen atoms, a (C3-C7 cycloalkyl)C1-C3 alkyl group having one or more substituents selected from Group G, a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 chain hydrocarbon group having one or more halogen atoms.

[Embodiment 21] The compound according to embodiment 20 wherein $R^{1x}$, $R^{1y}$ and $R^{1ay}$ are identical to or different from each other and each represents a C1-C5 alkyl group having three or more fluorine atoms.

[Embodiment 22] A compound of the present invention wherein T represents a C2-C10 chain hydrocarbon group having one or more halogen atoms.

[Embodiment 23] A compound of the present invention wherein T represents a C2-C10 alkyl group having three or more fluorine atoms.

[Embodiment 24] A compound of the present invention wherein T represents a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 chain hydrocarbon group having one or more halogen atoms.

[Embodiment 25] The compound according to embodiment 24 wherein $R^{1x}$, $R^{1y}$ and $R^{1ay}$ are identical to or different from each other and each represents a C1-C5 alkyl group having three or more fluorine atoms.

[Embodiment 26] The compound according to any one of embodiments 1 to 19 wherein T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy) C2-C5 alkyl group having one or more halogen atoms, a (C3-C7 cycloalkyl)C1-C3 alkyl group having one or more substituents selected from Group G, a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 chain hydrocarbon group having one or more halogen atoms.

[Embodiment 27] The compound according to any one of embodiments 1 to 19 wherein T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy) C2-C5 alkyl group having one or more halogen atoms, a (C3-C7 cycloalkyl)C1-C3 alkyl group having one or more substituents selected from Group G, a group represented by formula T-1, a group represented by formula T-2, a group represented by formula T-5, a group represented by formula T-6, a group represented by formula T-7, or a group represented by formula T-8, $R^{1x}$, and $R^{1y}$ and $R^{1ay}$ are identical to or different from each other and each represents a C1-C5 alkyl group having three or more fluorine atoms.

[Embodiment 28] The compound according to any one of embodiments 1 to 19 wherein T represents a C2-C10 chain hydrocarbon group having one or more halogen atoms.

[Embodiment 29] The compound according to any one of embodiments 1 to 19 wherein T represents a C2-C10 alkyl group having three or more fluorine atoms.

[Embodiment 30] The compound according to any one of embodiments 1 to 19 wherein T represents a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 chain hydrocarbon group having one or more halogen atoms.

[Embodiment 31] The compound according to any one of embodiments 1 to 19 wherein T represents a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 alkyl group having three or more fluorine atoms.

[Embodiment 32] The compound according to any one of embodiments 1 to 19 wherein $A^2$ represents a nitrogen atom, $A^3$ represents $CR^{4b}$, and T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy) C2-C5 alkyl group having one or more halogen atoms, a (C3-C7 cycloalkyl)C1-C3 alkyl group having one or more substituents selected from Group G, a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 chain hydrocarbon group having one or more halogen atoms.

[Embodiment 33] The compound according to any one of embodiments 1 to 19 wherein $A^2$ represents a nitrogen atom, $A^3$ represents $CR^{4b}$, and T represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy) C2-C5 alkyl group having one or more halogen atoms, a (C3-C7 cycloalkyl)C1-C3 alkyl group having one or more substituents selected from Group G, a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents a C1-C5 alkyl group having three or more fluorine atoms.

[Embodiment 34] The compound according to any one of embodiments 1 to 19 wherein $A^2$ represents a nitrogen atom, $A^3$ represents $CR^{4b}$, and T represents a C2-C10 chain hydrocarbon group having one or more halogen atoms.

[Embodiment 35] The compound according to any one of embodiments 1 to 19 wherein $A^2$ represents a nitrogen atom, $A^3$ represents $CR^{4b}$, and T represents a C2-C10 alkyl group having three or more fluorine atoms.

[Embodiment 36] The compound according to any one of embodiments 1 to 19 wherein $A^2$ represents a nitrogen atom, $A^3$ represents $CR^{4b}$, and T represents a group represented by formula T-1, a group represented by formula T-2, a group represented by formula T-5, a group represented by formula T-6, a group represented by formula T-7, or a group represented by formula T-8, $R^{1x}$, $R^{1y}$ and $R^{1ay}$ are identical to or different from each other and each represents a C1-C5 chain hydrocarbon group having one or more halogen atoms.

[Embodiment 37] The compound according to any one of embodiments 1 to 19 wherein $A^2$ represents a nitrogen atom, $A^3$ represents $CR^{4b}$, and T represents a group represented by formula T-1, a group represented by formula T-2, a group represented by formula T-5, a group represented by formula T-6, a group represented by formula T-7, or a group represented by formula T-8, and $R^{1x}$, $R^{1y}$ and $R^{1ay}$ are identical to or different from each other and each represents, a C1-C5 alkyl group having three or more fluorine atoms.

Next, a process for preparing a compound of the present invention is explained.

Process 1

A compound represented by formula (II-1-b) (hereinafter, referred to as compound (II-1-b)) or a compound represented by formula (II-1-c) (hereinafter, referred to as compound (II-1-c)) can be prepared by oxidizing a compound represented by formula (II-1-a) (hereinafter, referred to as compound (II-1-a)).

Examples of the catalyst to be used in the reaction include tungstic acid, and sodium tungstate.

In the reaction, the oxidizing agent is usually used within a range of 1 to 1.2 molar ratio(s), the base is usually used within a range of 0.01 to 1 molar ratio(s), and the catalyst is usually used within a range of 0.01 to 0.5 molar ratios, as opposed to 1 mole of the compound (II-1-a).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (II-1-b).

Next, a process for preparing the compound (II-1-c) from the compound (II-1-b) is described.

The reaction is usually carried out in a solvent. Examples of the solvents to be used in the reaction include halogenated hydrocarbons, nitriles, alcohols, acetic acid, water, and mixed solvents of two or more kinds of the solvents.

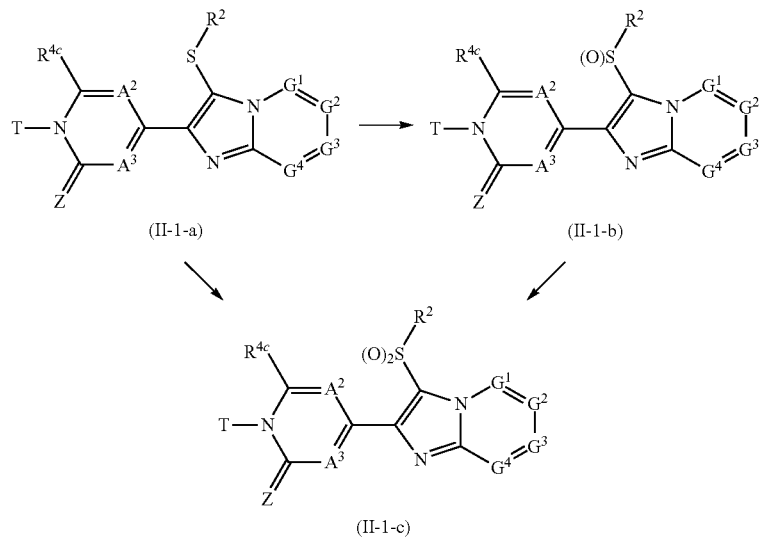

[wherein the symbols are the same as defined above.]

Firstly, a process for preparing the compound (II-1-b) from the compound (II-1-a) is described.

The reaction is usually carried out in a solvent. Examples of the solvent to be used in the reaction include halogenated hydrocarbons such as dichloromethane and chloroform (hereinafter, collectively referred to as halogenated hydrocarbons); nitriles such as acetonitrile (hereinafter collectively referred to as nitriles); alcohols such as methanol and ethanol (hereinafter, collectively referred to as alcohols); acetic acid; water; and mixed solvents of two or more kinds of the solvents.

Examples of the oxidizing agent to be used in the reaction include sodium periodate, m-chloroperoxybenzoic acid (hereinafter, referred to as mCPBA) and hydrogen peroxide.

When hydrogen peroxide is used as an oxidizing agent, a base or a catalyst may be added as needed.

Examples of the base include sodium carbonate.

Examples of the oxidizing agent to be used in the reaction include mCPBA and peroxide hydrogen.

When peroxide hydrogen is used an oxidizing agent, a base or a catalyst may be added as needed.

Examples of the base to be used in the reaction include sodium carbonate.

Examples of the catalyst to be used in the reaction include sodium tungstate.

In the reaction, the oxidizing agent is usually used within a range of 1 to 2 molar ratio(s), the base is usually used within a range of 0.01 to 1 molar ratio(s), and the catalyst is usually used within a range of 0.01 to 0.5 molar ratios, as opposed to 1 mole of the compound (II-1-b).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (II-1-c).

Also, the compound (II-1-c) can be prepared by reacting the compound (II-1-a) with an oxidizing agent in one step (one-spot).

The reaction may be carried out by using the oxidizing agent in a ratio of 2 to 5 molar ratios as opposed to 1 mole of the compound (II-1-a) according to the process for preparing the compound (II-1-c) from the compound (II-1-b).

Process 2

A compound represented by formula (II-2-b) and a compound represented by formula (II-2-c) can be prepared by oxidizing the compound represented by formula (II-2-a).

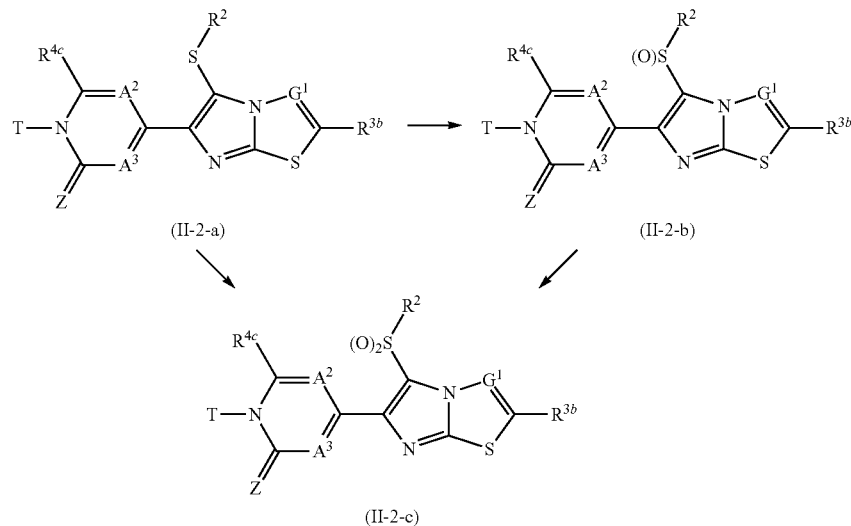

[wherein the symbols are the same as defined above.]

These reactions can be carried out according to the method described in the process 1.

Process 3

A compound represented by formula (II-3-b) and a compound represented by formula (II-3-c) can be prepared by oxidizing a compound represented by formula (II-3-a).

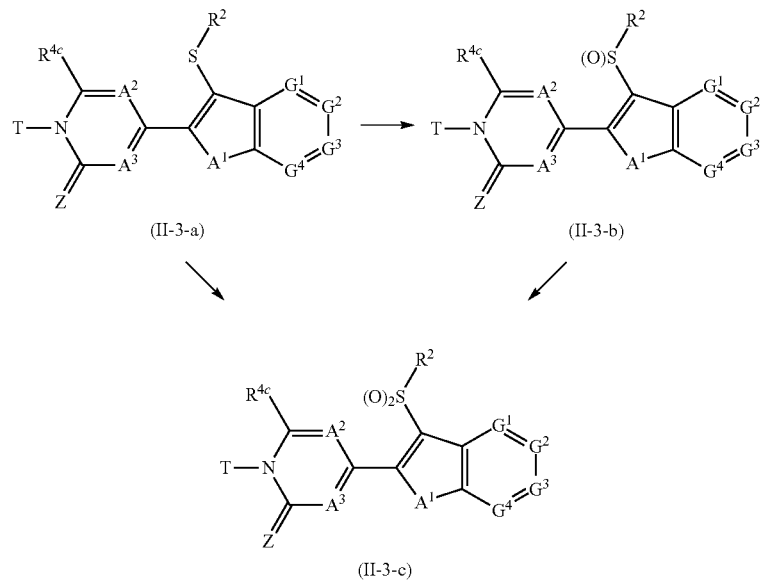

[wherein the symbols are the same as defined above.

These reactions can be carried out according to the method described in the process 1.

Process 4

A compound represented by formula (II-1-a1) (hereinafter, referred to as compound (II-1-a1)) can be prepared by reacting a compound represented by formula (M-1) (hereinafter, referred to as compound (M-1)) with a compound represented by formula (R1) (hereinafter, referred to as compound (R1)) in the presence of a base.

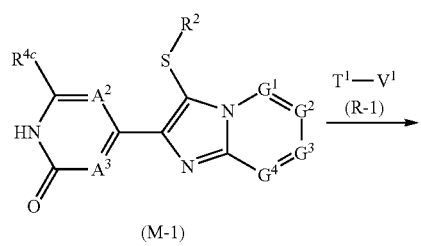

(M-1)

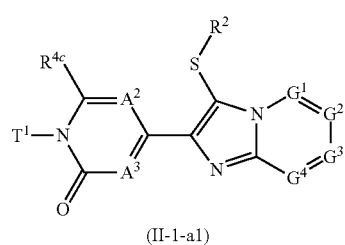

(II-1-a1)

[wherein $T^1$ represents a C2-C10 chain hydrocarbon group having one or more halogen atoms, a (C1-C5 alkoxy)C2-C5 alkyl group having one or more halogen atoms, a (C3-C5 alkenyloxy)C2-C5 alkyl group having one or more halogen atoms, a (C3-C5 alkynyloxy)C2-C5 alkyl group having one or more halogen atoms, a (C3-C7 cycloalkyl)C1-C3 alkyl group having one or more substituents selected from Group G, a (C1-C5 alkyl)-S(O)$_m$—(C2-C5 alkyl) group having one or more halogen atoms, a (C3-C5 alkenyl)-S(O)$_m$—(C2-C5 alkyl) group having one or more halogen atoms, a (C3-C5 alkynyl)-S(O)$_m$—(C2-C5 alkyl) group having one or more halogen atoms, or a (C1-C5 alkyl)-C(O)—(C1-C5 alkyl) group having one or more halogen atoms, $V^1$ represents a chlorine atom, a bromine atom, an iodine atom, or a C1-C10 alkylsulfonyloxy group, and the other symbols are the same as defined above.]

The reaction is usually carried out in a solvent. Examples of the solvents to be used in the reaction include ethers such as tetrahydrofuran (hereinafter, referred to as THF), 1,4-dioxane, ethylene glycol dimethyl ether (hereinafter, referred to as DME), methyl tert-butyl ether (hereinafter, referred to as MTBE) (hereinafter, collectively referred to as ethers); aromatic hydrocarbons such as toluene and xylene (hereinafter, collectively referred to as aromatic hydrocarbons); and polar aprotic solvents such as dimethylformamide (hereinafter, referred to as DMF), N-methyl pyrrolidone and dimethyl sulfoxide (hereinafter, referred to DMSO) (hereinafter, collectively referred to as polar aprotic solvents); and mixed solvents of two or more kinds of the solvents.

Examples of the base to be used in the reaction include organic bases such as triethylamine, diisopropylethylamine, pyridine, and 4-dimethylaminopyridine (hereinafter, collectively referred to as organic bases); alkali metal hydrides such as sodium hydride (hereinafter, collectively referred to as alkali metal hydrides); and alkali metal carbonates such as sodium carbonate, potassium carbonate (hereinafter, collectively referred to as alkali metal carbonates).

In the reaction, the compound (R1) is usually used within a range of 1 to 5 molar ratio(s), and the base is usually used within a range of 1 to 10 molar ratio(s), as opposed to 1 mole of the compound (M-1).

The reaction temperature is usually within a range of −20° C. to 150° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to obtain the compound (II-1-a1).

The compound (R1) is publicly known, or can be prepared according to a publicly known method.

Process 5

A compound represented by formula (II-1-a2) (hereinafter, referred to as compound (II-1-a2)) can be prepared by reacting the compound (M-1) with a compound represented by formula (R2) (hereinafter, referred to as compound (R2)) in the presence of a base.

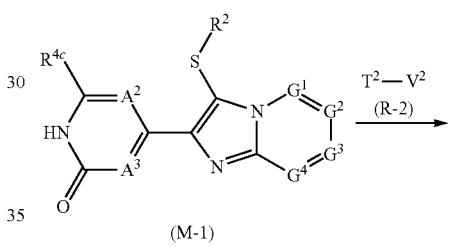

(M-1)

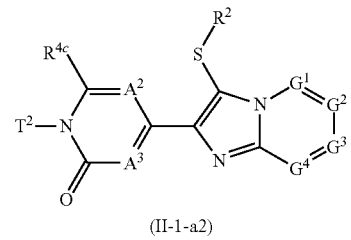

(II-1-a2)

[wherein $T^2$ represents a group represented by formula T-1, a group represented by formula T-2, a group represented by formula T-3, a group represented by formula T-4, a group represented by formula T-5, a group represented by formula T-6, a group represented by formula T-7, or a group represented by formula T-8, V2 represents a fluorine atom, a chlorine atom, or a C1-C10 alkylsulfonyloxy group, and the other symbols are the same as defined above.]

The reaction can be carried out according to the method described in the process 4.

The compound (R2) is publically known, or can be prepared according to a publically known method.

Preparation Example 6

The compound (II-1-a2) can be prepared by reacting the compound (M-1) with a compound represented by formula (R-3) (hereinafter, referred to as compound (R-3)) in the presence of a metal catalyst or a base.

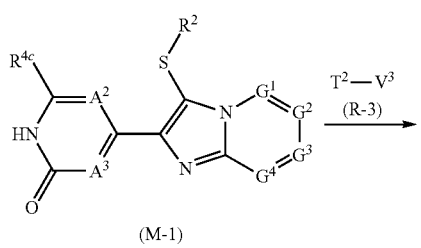

(M-1)

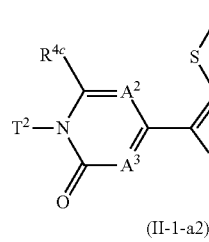

(II-1-a2)

[wherein $V^3$ represents a bromine atom or an iodine atom, and the other symbols are the same as defined above.]

The reaction is usually carried out in a solvent. Examples of the solvents to be used in the reaction include ethers, aromatic hydrocarbons, polar aprotic solvents, water, and mixed solvents of two or more kinds of the solvents.

Examples of the meal catalyst to be used in the reaction include copper catalysts such as copper(I) iodide, copper(I) bromide, copper(I) chloride, copper(I) oxide, copper(I) trifluoromethanesulfonate benzene complex, tetrakis(acetonitrile)copper(I) hexafluorophosphate, and copper(I) 2-thiophenecarboxylate; and nickel catalysts such as bis(cyclooctadiene)nickel(0) and nickel(II) chloride.

A ligand, a base, or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, 1,10-phenanthroline, trans-1,2-cyclohexanediamine, trans-N,N'-dimethylcyclohexane-1,2-diamine, and N,N'-dimethylethylenediamine.

Examples of the base to be used in the reaction include organic bases, alkali metal hydrides, and alkali metal carbonates.

Examples of the inorganic halogenated compounds include alkali metal fluorides such as potassium fluorides and sodium fluoride; and alkali metal chlorides such as sodium chloride.

In the reaction, the compound (R-2) is usually used within a range of 1 to 10 molar ratio(s), the metal catalyst is usually used within a range of 0.01 to 2 molar ratio(s), the ligand is usually used within a range of 0.01 to 1 molar ratio(s), the base is usually used within a range of 0.1 to 5 molar ratio(s), and the inorganic halogenated compound is usually used within a range of 0.1 to 5 molar ratio(s), as opposed to 1 mole of the compound (M-1).

The reaction temperature is usually within a range of −20 to 200° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (II-1-a2).

The compound (R-3) is publically known, or can be prepared according to a publically known method.

Process 7

A compound represented by formula (II-2-a1) (hereinafter, referred to as compound (II-2-a1)) can be prepared by reacting a compound represented by formula (M-2) (hereinafter, referred to as compound (M-2)) with the compound (R1) in the presence of a base.

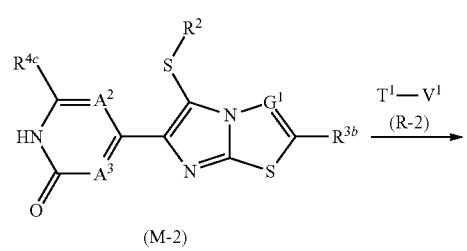

(M-2)

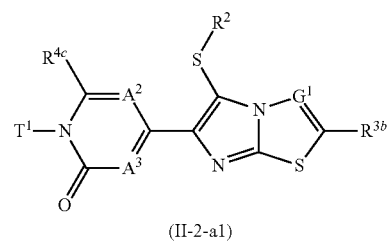

(II-2-a1)

[wherein the symbols are the same as defined above.]

The reaction can be carried out according to the method described in the process 4.

Process 8

A compound represented by formula (II-2-a2) (hereinafter, referred to as compound (II-2-a2)) can be prepared by reacting the compound (M-2) with the compound (R2) in the presence of a base.

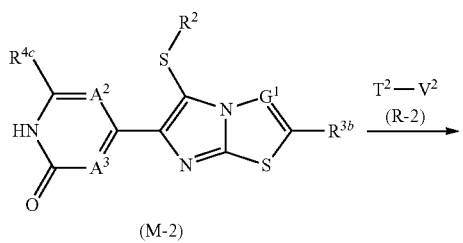

(M-2)

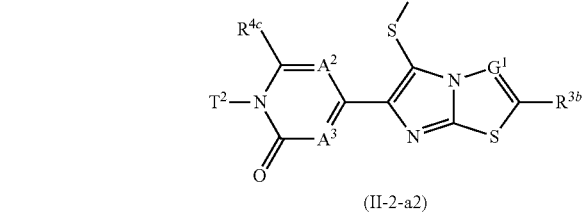

(II-2-a2)

[wherein the symbols are the same as defined above.]

The reaction can be carried out according to the method described in the process 5.

Process 9

The compound (II-2-a2) can be prepared by reacting the compound (M-2) with the compound (R-3) in the presence of a base.

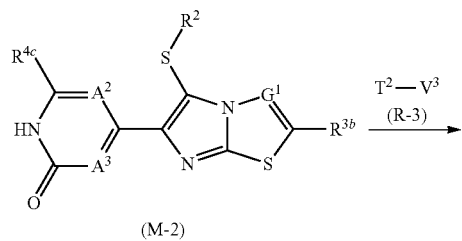

(M-2)

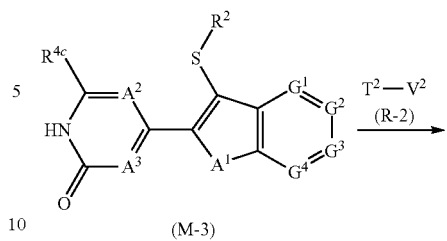

(M-3)

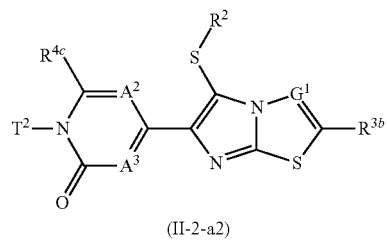

(II-2-a2)

[wherein the symbols are the same as defined as above.]

The reaction can be carried out according to the method described in the process 6.

Process 10

A compound represented by formula (II-3-a1) (hereinafter, referred to as compound (II-3-a1)) can be prepared by reacting a compound represented by formula (M-3) (hereinafter, referred to as compound (M-3)) with the compound (R1) in the presence of a base.

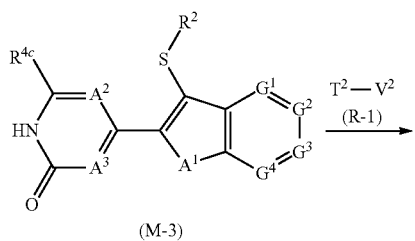

(M-3)

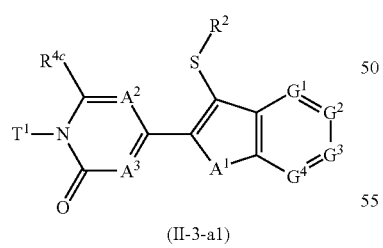

(II-3-a1)

[wherein the symbols are the same as defined above.]

The reaction can be carried out according to the method described in the process 4.

Process 11

A compound represented by formula (II-3-a2) (hereinafter, referred to as compound (II-3-a2)) can be prepared by reacting the compound (M-3) with the compound (R2) in the presence of a base.

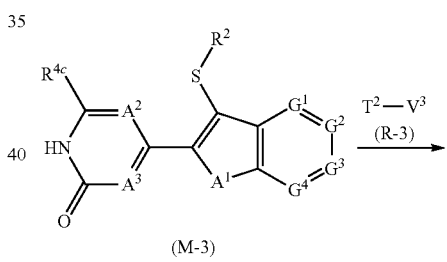

(II-3-a2)

[wherein the symbols are the same as defined above.]

The reaction can be carried out according to the method described in the process 5.

Process 12

The compound (II-3-a2) can be prepared by reacting the compound (M-3) with the compound (R-3) in the presence of a base.

(M-3)

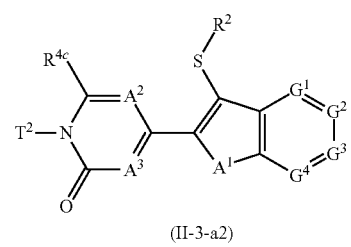

(II-3-a2)

[wherein the symbols are the same as defined above.]

The reaction can be carried out according to the method described in the process 6.

Process 13

The compound (M-1) can be prepared according to the below-mentioned scheme.

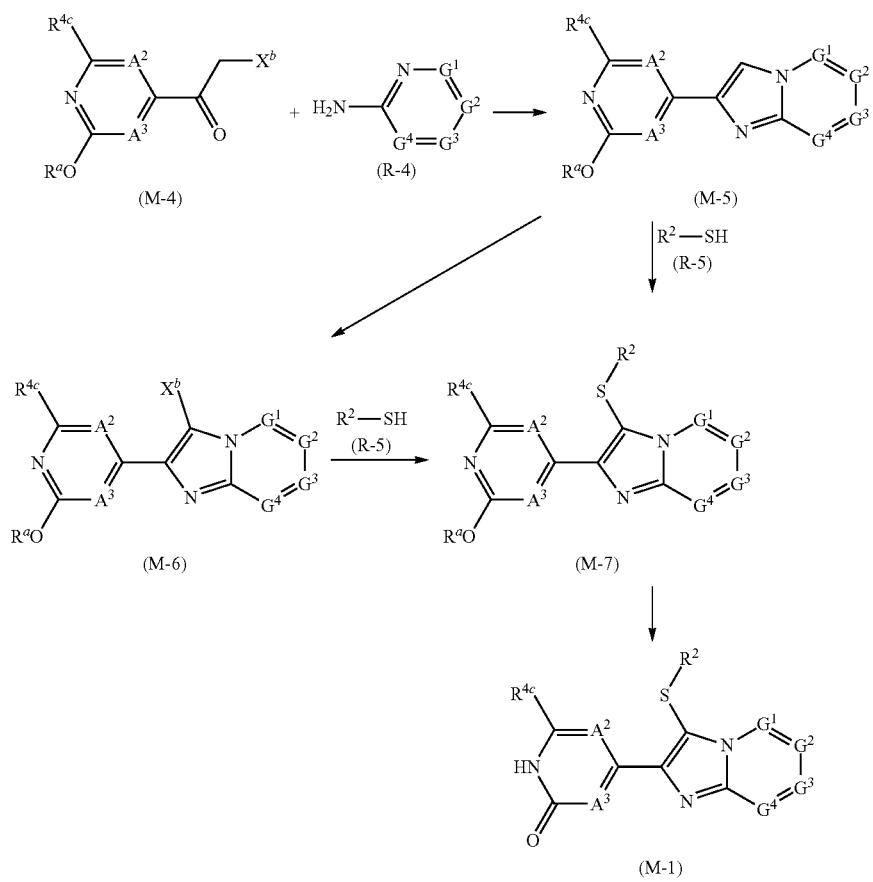

(M-4)  (R-4)  (M-5)  (M-6)  (M-7)  (M-1)

[wherein $R^a$ represents a methyl group or an ethyl group, $X^b$ represents a chlorine atom, a bromine atom, or an iodine atom, and the other symbols are the same as defined above.]

Firstly, the process for preparing a compound represented by formula (M-5) (hereinafter, referred to as compound (M-5)) is described.

The compound (M-5) can be prepared by reacting a compound represented by formula (M-4) (hereinafter, referred to as compound (M-4)) with a compound represented by formula (R-4) (hereinafter, referred to as compound (R-4)).

The reaction is usually carried out in a solvent. Examples of the solvents to be used in the reaction include ethers, aromatic hydrocarbons, polar aprotic solvents, alcohols, nitriles, water, and mixed solvents of two or more kinds of the solvents.

A base may be used in the reaction as needed. Examples of the base include organic bases and alkali metal carbonates.

In the reaction, the compound (R-4) is usually used within a range of 1 to 10 molar ratio(s), and the base is usually used within a range of 0.1 to 5 molar ratio(s), as opposed to 1 mole of the compound (M-4).

The reaction temperature of the reaction is usually within a range of −20 to 200° C. The reaction period of the reaction is usually within a range of 0.1 to 48 hours.

When the reaction is completed, water is added to the reaction mixtures, and the reaction mixtures are extracted with organic solvent(s), and the organic solvents are worked up (for example, drying and concentration) to give the compound (M-5).

The compound (R-4) is publically known, or can be prepared according to a publically known method.

Next, a process for preparing a compound represented by formula (M-6) (hereinafter, referred to compound (M-6)) is described.

The compound (M-6) can be prepared by reacting the compound (M-5) with the halogenating agent.

The reaction is usually carried out in a solvent. Examples of the solvents to be used in the reaction include alcohols, nitriles, ethers, aromatic hydrocarbons, polar aprotic solvents, halogenated hydrocarbons, water, and mixed solvents of two or more kinds of the solvents.

Examples of the halogenating agents include chlorine, bromine, iodine, N-chlorosuccinimide, N-bromosuccinimide, N-iodosuccinimide.

In the reaction, the halogenating agent is usually used within a range of 1 to 20 molar ratio(s), as opposed to 1 mole of the compound (M-5).

The reaction temperature of the reaction is usually within a range of −20 to 200° C. The reaction period of the reaction is usually within a range of 0.1 to 72 hours.

When the reaction is completed, water is added to the reaction mixtures, and the reaction mixtures are extracted with organic solvent(s), and the organic solvents are worked up (for example, drying and concentration) to give the compound (M-6).

Next, the process for preparing a compound represented by formula (M-7) (hereinafter, referred to as compound (M-7)) from the compound (M-5).

The compound (M-7) can be prepared by reacting the compound (M-5), a compound represented by formula (R5) (hereinafter, referred to as the compound (R5)) and a halogenating agent.

The reaction is usually carried out in a solvent. Examples of the solvents to be used include alcohols, nitriles, ethers, aromatic hydrocarbons, polar aprotic solvents, halogenated hydrocarbons, water, and mixed solvents of two or more kinds of the solvents.

Examples of the halogenating agent include chlorine bromine, iodine, N-chlorosuccinimide, N-bromosuccinimide, and N-iodosuccinimide.

In the reaction, the compound (R5) is usually used within a range of 1 to 2 molar ratio(s) as opposed to 1 mole of the compound (M-5).

The reaction temperature of the reaction is usually within a range of −20 to 200° C. The reaction period of the reaction is usually within a range of 0.1 to 72 hours.

When the reaction is completed, water is added to the reaction mixtures, and the reaction mixtures are extracted with organic solvent(s), and the organic solvents are worked up (for example, drying and concentration) to give the compound (M-7).

The compound (R5) is publically known, or can be prepared according to a publically known method.

Next, the process for preparing the compound (M-7) from the compound (M-6) is described.

The compound (M-7) can be also prepared by reacting the compound (M-6) with the compound (R5) in the presence of a metal catalyst and a bae.

The reaction is usually carried out in a solvent. Examples of the solvents to be used in the reaction include alcohols, nitriles, ethers, aromatic hydrocarbons, polar aprotic solvents, water, and mixed solvents of two or more kinds of the solvents.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

Examples of the base to be used in the reaction include alkali metal hydrides, alkali metal carbonates, and organic bases.

A ligand may be used in the reaction. Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

In the reaction, the compound (R5) is usually used within a range of 1 to 20 molar ratio(s), the metal catalyst is usually used within a range of 0.01 to 0.5 molar ratios, the ligand is usually used within a range of 0.01 to 1 molar ratio(s), and the base is usually used within a range of 0.1 to 5 molar ratio(s), as opposed to 1 mole of the compound (M-6).

The reaction temperature of the reaction is usually within a range of −20 to 200° C. The reaction period of the reaction is usually within a range of 0.1 to 72 hours.

When the reaction is completed, water is added to the reaction mixtures, and the reaction mixtures are extracted with organic solvent(s), and the organic solvents are worked up (for example, drying and concentration) to give the compound (M-7).

Next, the process for preparing the compound (M-1) from the compound (M-7) is described.

The compound (M-1) can be prepared by reacting the compound (M-7 in the presence of an acid.

The reaction is usually carried out in a solvent. Examples of the solvents to be used in the reaction include halogenated hydrocarbons, aromatic hydrocarbons, nitriles, alcohols, acetic acid, water, and mixed solvents of two or more kinds of the solvents.

Examples of the acid to be used in the reaction include mineral acids such as hydrochloric acid and sulfuric acid; borons such as boron trichloride and boron trifluoride; and metal chlorides such as titanium chloride and aluminium chloride.

In the reaction, the acid is usually used within a range of 0.1 to 10 molar ratio(s), as opposed to 1 mole of the compound (M-7). When the mineral acids are used in the reaction, the mineral acids are used also as a solvent.

The reaction temperature of the reaction is usually within a range of −20 to 150° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (M-1).

Process 14

The compound (M-7) can be prepared by reacting the compound (R-4) with a compound represented by formula (M-8) (hereinafter, referred to as compound (M-8)).

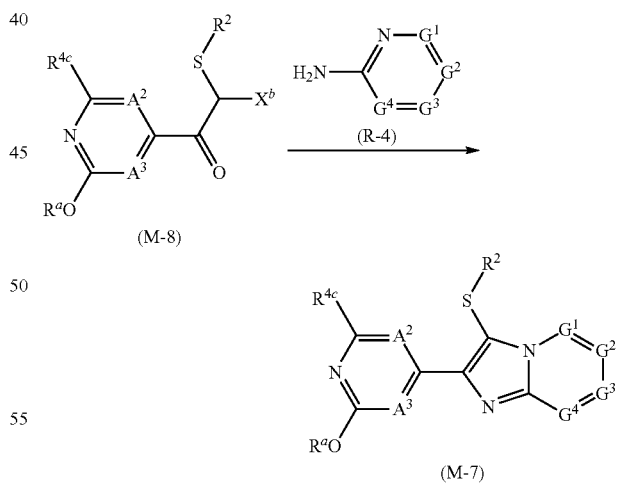

[wherein the symbols are the same as defined above.]

The reaction can be carried out according to the method for preparing the compound (M-5) from the compound (M-4) described in the process 13

Process 15

The compound (M-2) can be prepared according to the below-mentioned scheme.

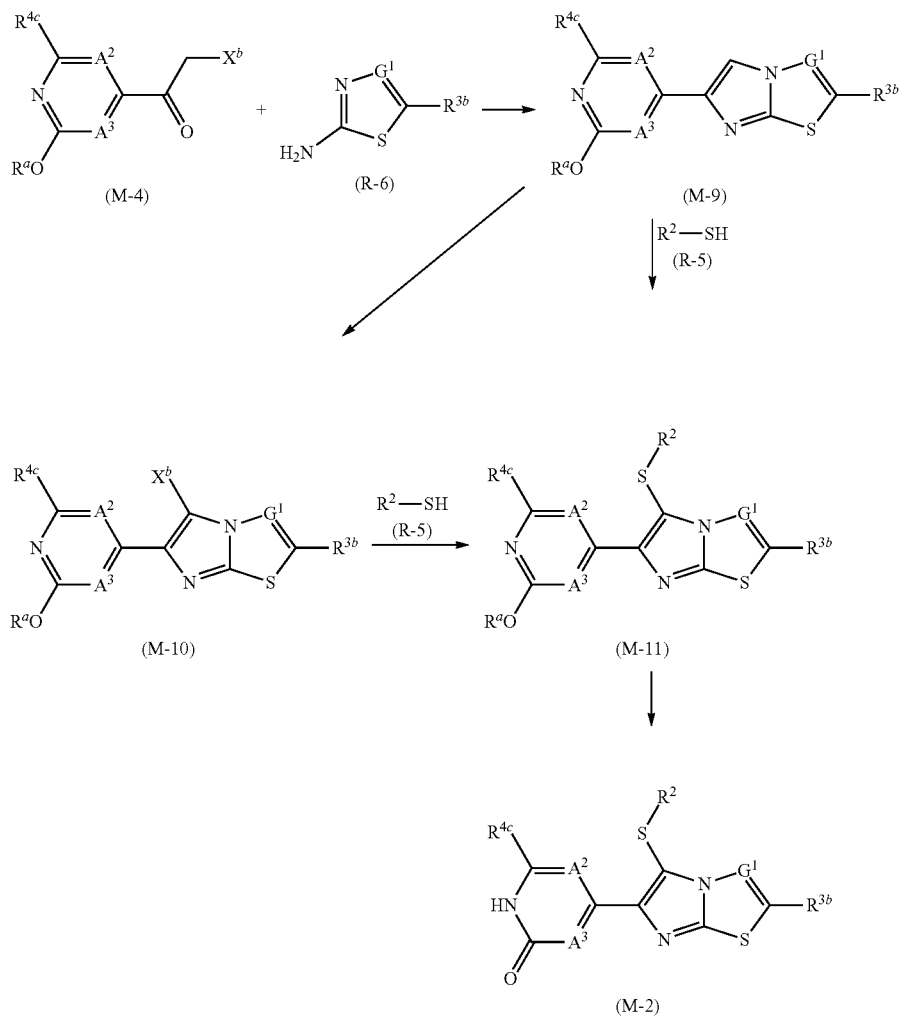

[wherein the symbols are the same as defined above.]

A compound represented by formula (M-9) (hereinafter, referred to as compound (M-9)) can be prepared by reacting the compound (M-4) with a compound represented by formula (R-6) (hereinafter, referred to as compound (R-6)).

A compound represented by formula (hereinafter, referred to as compound (M-11)) can be prepared by reacting the compound (M-9), the compound (R5) and a halogenating agent.

A compound represented by formula (M-10) (hereinafter, referred to as compound (M-10)) can be prepared by reacting the compound (M-9) with a halogenating agent.

The compound (M-11) can be also prepared by reacting the compound (M-10) with the compound (R5) in the presence of a metal catalyst and a base.

These reactions can be carried out according to the methods described in the process 13.

The compound (R-6) is publically known, or can be prepared according to the publically known method.

Process 16

The compound (M-11) can be prepared by reacting the compound (R-6) with the compound (M-8).

[wherein the symbols are the same as defined above.]

The reaction can be carried out according to the method for preparing the compound (N-5) from the compound (M-4) described in the process 13.

Process 17

The compound (M-3) can be prepared according to the below-mentioned scheme.

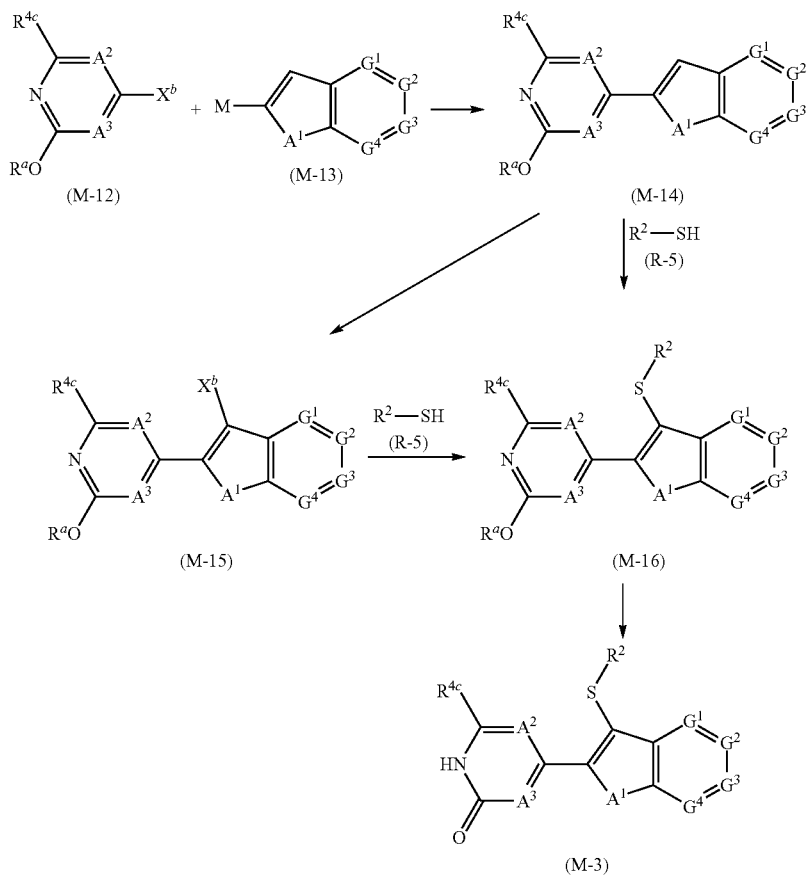

[wherein M represents a 9-borabicyclo[3.3.1]nonan-9-yl group, a borono group, a 4,4,5,5,-tetramethyl-1,3,2-dioxaborolan-2-yl, a tributylstannyl group, ZnCl, MgCl, or MgBr, and the other symbols are the same as defined above.]

Firstly, a process preparing a compound represented by formula (M-14) (hereinafter, referred to as compound (M-14)) is described.

The compound (M-14) can be prepared by reacting a compound represented by formula (M-12) (hereinafter, referred to as compound (M-12)) with a compound represented by formula (M-13) (hereinafter, referred to as compound (M-13)) in the presence of a metal catalyst.

The reaction is usually carried out in a solvent. Examples of the solvents to be used in the reaction include ethers, aromatic hydrocarbons, polar aprotic solvents, water, and mixed solvents of two or more kinds of the solvents.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

A ligand, a base, or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

The bases to be used in the reaction include alkali metal hydrides, alkali metal carbonates, and organic bases.

Examples of the inorganic halogenated compounds include alkali metal fluorides such as potassium fluorides and sodium fluorides; and alkali metal chlorides such as lithium chloride and sodium chloride.

In the reaction, the compound (M-13) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratio(s), and the inorganic halogenated compound is usually used within a range of 0.1 to 5 molar ratio(s), as opposed to 1 mole of the compound (M-12).

The reaction temperature of the reaction is usually within a range of −20 to 200° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (M-14).

The compound (M-13) is publically known, or can be prepared according to the publically known method.

Next, a process for preparing a compound represented by formula (M-15) (hereinafter, referred to as compound (M-15)) is described.

The compound. (M-15) can be prepared by reacting the compound (M-14) with a halogenating agent. The reaction can be carried out according to the method for preparing the compound (M-6) from the compound (M-5) described in the process 13.

Next, a process for preparing a compound represented by formula (M-16) (hereinafter, referred to as compound (M-16)) is described.

The compound (M-16) can be prepared by reacting the compound (M-14), the compound (R5) and a halogenating agent. The reaction can be carried out according to the method for preparing the compound (M-7) from the compound (M-5) described in the process 13.

The compound (M-16) can be also prepared by reacting the compound (M-15) with the compound (R5) in the presence of a metal catalyst and a base. The reaction can be carried out according to the method for preparing the compound (M-7) from the compound (M-6) described in the process 13.

Next, a process for preparing the compound (M-3) is described.

The compound (M-3) can be prepared by reacting the compound (M-16) in the presence of an acid. The reaction can be carried out according to the method for preparing the compound (M-1) from the compound (M-7) described in the process 13.

A method for synthesizing an intermediate compound is described below.

Reference Process 1

The compound (M-4) and the compound (M-8) can be prepared according to the below-mentioned scheme.

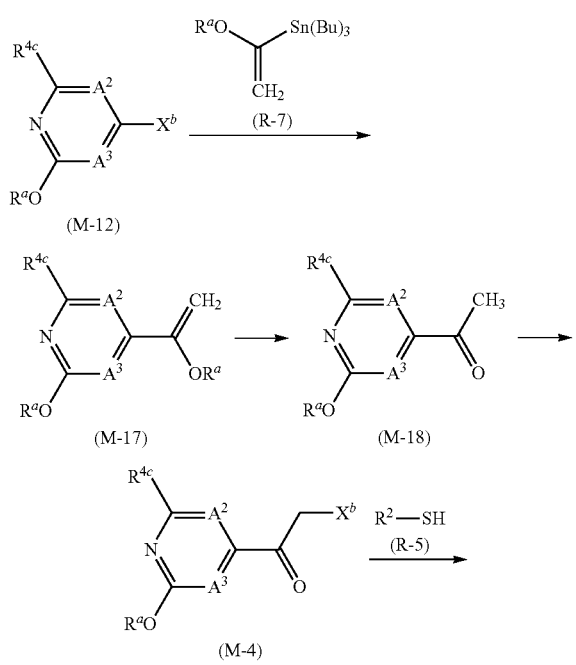

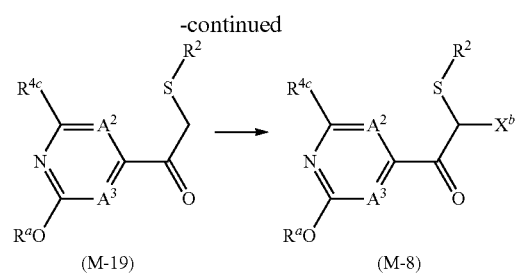

[wherein the symbols are the same as defined above.]

A compound represented by formula (M-17) (hereinafter, referred to as compound (M-17)) can be prepared by reacting the compound (M-12) with a compound represented by formula (R-7) (hereinafter, referred to as compound (R-7)). The reaction can be carried out according to the method described in, for example, WO 2016/123253.

The compound (M-12) and the compound (R-7) are publically known, or can be prepared according to the publically known method.

A compound represented by formula (M-18) (hereinafter, referred to as compound (M-18)) can be prepared by reacting the compound (M-18) in the presence of an acid. The reaction may be carried out according to the method described in, for example, WO 2016/123253.

The compound (M-4) can be prepared by reacting the compound (M-18) with a halogenating agent. The reaction can be carried out according to the method described in, for example, WO 2013/191113.

A compound represented by formula (M-19) (hereinafter, referred to as compound (M-19)) can be prepared by reacting the compound (M-4) with the compound (R5) in the presence of a base. The reaction can be carried out according to the method described in Tetrahedron Letters, 64, 7419 (2008).

The compound (M-8) can be prepared by reacting the compound (M-19) with a halogenating agent. The reaction can be carried out according to the method described in O 2013/191113.

Next, specific examples of the compound of the present invention are indicated below. These compounds can be prepared according to the Examples, the Processes and the Reference Processes described herein.

Herein, Me represents a methyl group, Et represents an ethyl group, Pr represents a propyl group, i-Pr represents an isopropyl group, c-Pr represents a cyclopropyl group, Ph represents a phenyl group, Py2 represents a 2-pyridyl group, Py3 represents a 3-pyridyl group, Py4 represents a 4-pyridyl group. When the c-Pr, Ph, Py2, Py3, and Py4 have any substituent(s), the substituent(s) is described together with a substitution position before the symbol. For example, 1-CN-c-Pr represents a 1-cyano-cyclopropyl group, 4-$CF_3$—Py2 represents a 4-(trifluoromethyl)-2-pyridyl group, and 3,5-$(CF_3)_2$-Ph represents a 3,5-bis(trifluoromethyl)phenyl group.

A compound represented by formula (L-1):

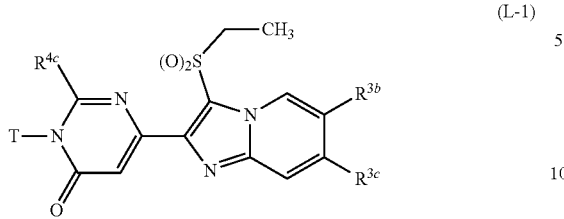

(hereinafter, referred to as compound (L-1)), wherein $R^{3b}$, $R^{3c}$ and $R^{4c}$ represent a hydrogen atom, and T represents any substituents indicated in Table 1 to Table 6 (hereinafter, referred to as Compound Class $SX_1$).

TABLE 1

| |
|---|
| $CH_2CHF_2$ |
| $CH_2CF_3$ |
| $CF_2CHF_2$ |
| $CF_2CF_3$ |
| $CH(CH_3)CF_3$ |
| $CH_2CF_2CHF_2$ |
| $CH_2CF_2CF_3$ |
| $CF_2CF_2CF$ |
| $CH_2CF_2CHFCF_3$ |
| $CH_2CF_2CF_2CF_3$ |
| $CF_2CF_2CF_2CF_3$ |
| $CH_2CF_2CF_2CF_2CF_3$ |
| $CF_2CF_2CF_2CF_2CF_3$ |
| $CH_2CH\text{-}CHCF_3$ |
| $CH_2CCl=CCl_2$ |
| $CH_2C\equiv CCF_3$ |
| $CH_2CH_2OCF_3$ |
| $CH_2CH_2OCH_2CF_3$ |
| $CH_2CH_2OCF_2CF_3$ |
| $CH_2\text{-}2,2\text{-}F_2\text{-}c\text{-}Pr$ |
| $CH_2\text{-}1\text{-}CF_3\text{-}c\text{-}Pr$ |

TABLE 2

| |
|---|
| $CH_2CH_2SCF_3$ |
| $CH_2CH_2SCH_2CF_3$ |
| $CH_2CH_2SCF_2CF_3$ |
| $CH_2CH_2SCH_2CF_2CF_3$ |
| $CH_2CH_2SCF_2CF_2CF_3$ |
| $CH_2CH_2SCH_2CF_2CF_2CF_3$ |
| $CH_2CH_2SCF_2CF_2CF_2CF_3$ |
| $CH_2CH_2S(O)CF_3$ |
| $CH_2CH_2S(O)CH_2CF_3$ |
| $CH_2CH_2S(O)CF_2CF_3$ |
| $CH_2CH_2S(O)CH_2CF_2CF_3$ |
| $CH_2CH_2S(O)CF_2CF_2CF_3$ |
| $CH_2CH_2S(O)CH_2CF_2CF_2CF_3$ |
| $CH_2CH_2S(O)CF_2CF_2CF_2CF_3$ |
| $CH_2CH_2S(O)_2CF_3$ |
| $CH_2CH_2S(O)_2CH_2CF_3$ |
| $CH_2CH_2S(O)_2CF_2CF_3$ |
| $CH_2CH_2S(O)_2CH_2CF_2CF_3$ |
| $CH_2CH_2S(O)_2CF_2CF_2CF_3$ |
| $CH_2CH_2S(O)_2CH_2CF_2CF_2CF_3$ |
| $CH_2CH_2S(O)_2CF_2CF_2CF_2CF_3$ |

TABLE 3

| |
|---|
| $CH_2C(O)CF_3$ |
| $CH_2C(O)CF_2CF_3$ |
| $CH_2C(O)CF_2CF_2CF_3$ |
| $CH_2CH_2C(O)CF_3$ |
| $CH_2CH_2C(O)CF_2CF_3$ |

TABLE 3-continued

| |
|---|
| $CH_2CH_2C(O)CF_2CF_2CF_3$ |
| $CH_2CH_2C(O)CF_3$ |
| $CH_2CH_2C(O)CF_2CF_3$ |
| $CH_2CH_2C(O)CF_2CF_2CF_3$ |
| $3\text{-}CF_3\text{-}Ph$ |
| $4\text{-}CF_3\text{-}Ph$ |
| $3,5\text{-}(CF_3)_2\text{-}Ph$ |
| $3\text{-}SCF_3\text{-}Ph$ |
| $3\text{-}S(O)CF_3\text{-}Ph$ |
| $3\text{-}S(O)_2CF_3\text{-}Ph$ |
| $4\text{-}SCF_3\text{-}Ph$ |
| $4\text{-}S(O)CF_3\text{-}Ph$ |
| $4\text{-}S(O)_2CF_3\text{-}Ph$ |

TABLE 4

| |
|---|
| $4\text{-}CF_3\text{-}Py2$ |
| $5\text{-}CF_3\text{-}Py2$ |
| $4\text{-}SCF_3\text{-}Py2$ |
| $4\text{-}S(O)CF_3\text{-}Py2$ |
| $4\text{-}S(O)_2CF_3\text{-}Py2$ |
| $5\text{-}SCF_3\text{-}Py2$ |
| $5\text{-}S(O)CF_3\text{-}Py2$ |
| $5\text{-}S(O)_2CF_3\text{-}Py2$ |
| $5\text{-}NMeCH_2CF_3\text{-}Py2$ |
| $5\text{-}CF_3\text{-}Py3$ |
| $6\text{-}CF_3\text{-}Py3$ |
| $5\text{-}SCF_3\text{-}Py3$ |
| $5\text{-}S(O)CF_3\text{-}Py3$ |
| $5\text{-}S(O)_2CF_3\text{-}Py3$ |
| $6\text{-}SCF_3\text{-}Py3$ |
| $6\text{-}S(O)_2CF_3\text{-}Py3$ |
| $6\text{-}S(O)_2CF_3\text{-}Py3$ |
| $6\text{-}NMeCH_2CF_3\text{-}Py3$ |

TABLE 5

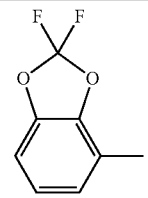

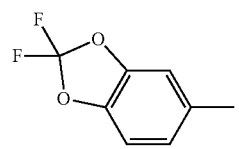

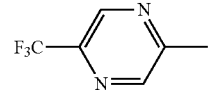

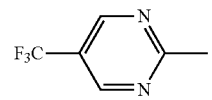

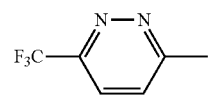

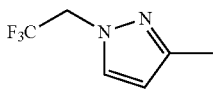

TABLE 5-continued

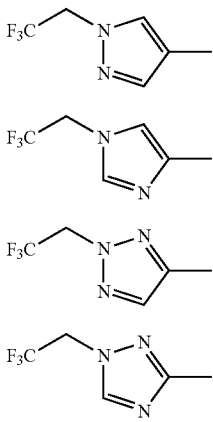

TABLE 6

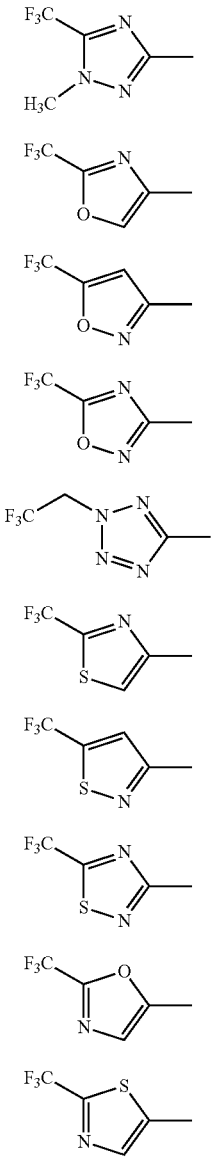

A compound (L-1) wherein $R^{3b}$ and $R^{3c}$ a represent hydrogen atom, $R^{4c}$ represents an ethyl group, and T represents any substituents indicated in Table 1 to Table 6 (hereinafter, referred to as Compound Class $SX_2$).

A compound (L-1) wherein $R^{3b}$ and $R^{3c}$ a represent hydrogen atom, $R^{4c}$ represents an ethyl group, and T represents any substituents indicated in Table 1 to Table 6 (hereinafter, referred to as Compound Class $SX_3$).

A compound (L-1) wherein $R^{3b}$ and $R^{3c}$ a represent hydrogen atom, $R^{4c}$ represents a methoxy group, and T represents any substituents indicated in Table 1 to Table 6 (hereinafter, referred to as Compound Class $SX_4$).

A compound (L-1) wherein $R^{3b}$ and $R^{3c}$ a represent hydrogen atom, $R^{4c}$ represents a chlorine atom, and T represents any substituents indicated in Table 1 to Table 6 (hereinafter, referred to as Compound Class $SX_5$).

A compound (L-1) wherein $R^{3b}$ and $R^{3c}$ a represent hydrogen atom, $R^{4c}$ represents a bromine atom, and T represents any substituents indicated in Table 1 to Table 6 (hereinafter, referred to as Compound Class $SX_6$).

A compound (L-1) wherein $R^{3b}$ and $R^{3c}$ a represent hydrogen atom, $R^{4c}$ represents a cyano group, and T represents any substituents indicated in Table 1 to Table 6 (hereinafter, referred to as Compound Class $SX_7$).

A compound (L-1) wherein $R^{3b}$ represents a trifluoromethyl group, $R^{3c}$ and $R^{4c}$ represent a hydrogen atom, and T represents any substituents indicated in Table 1 to Table 6 (hereinafter, referred to as Compound Class $SX_8$).

A compound (L-1) wherein $R^{3b}$ represents a trifluoromethyl group, $R^{3c}$ represents a hydrogen atom, and $R^{4c}$ represents a methyl group, and T represents any substituents indicated in Table 1 to Table 6 (hereinafter, referred to as Compound Class $SX_9$).

A compound (L-1) wherein $R^{3b}$ represents a trifluoromethyl group, $R^{3c}$ represents a hydrogen atom, and $R^{4c}$ represents an ethyl group, and T represents any substituents indicated in Table 1 to Table 6 (hereinafter, referred to as Compound Class $SX_{10}$).

A compound (L-1) wherein $R^{3b}$ represents a trifluoromethyl group, $R^{3c}$ represents a hydrogen atom, and $R^{4c}$ represents a methoxy group, and T represents any substituents indicated in Table 1 to Table 6 (hereinafter, referred to as Compound Class $SX_{11}$).

A compound (L-1) wherein $R^{3b}$ represents a trifluoromethyl group, $R^{3c}$ represents a hydrogen atom, and $R^{4c}$ represents a chlorine atom, and T represents any substituents indicated in Table 1 to Table 6 (hereinafter, referred to as Compound Class $SX_{12}$).

A compound (L-1) wherein $R^{3b}$ represents a trifluoromethyl group, $R^{3c}$ represents a hydrogen atom, and $R^{4c}$ represents a bromine atom, and T represents any substituents indicated in Table 1 to Table 6 (hereinafter, referred to as Compound Class $SX_{13}$).

A compound (L-1) wherein $R^{3b}$ represents a trifluoromethyl group, $R^{3c}$ represents a hydrogen atom, and $R^{4c}$ represents a cyano group, and T represents any substituents indicated in Table 1 to Table 6 (hereinafter, referred to as Compound Class $SX_{14}$).

A compound (L-1) wherein $R^{3c}$ represents a trifluoromethyl group, $R^{3b}$ and $R^{4c}$ represents a hydrogen atom, and T represents any substituents indicated in Table 1 to Table 6 (hereinafter, referred to as Compound Class $SX_{15}$).

A compound (L-1) wherein $R^{3c}$ represents a trifluoromethyl group, $R^{3b}$ represents a hydrogen atom, and $R^{4c}$ represents a methyl group, and T represents any substituents indicated in Table 1 to Table 6 (hereinafter, referred to as Compound Class $SX_{16}$).

A compound (L-1) wherein $R^{3c}$ represents a trifluoromethyl group, $R^{3b}$ represents a hydrogen atom, and $R^{4c}$ represents an ethyl group, and T represents any substituents indicated in Table 1 to Table 6 (hereinafter, referred to as Compound Class $SX_{17}$).

A compound (L-1) wherein $R^{3c}$ represents a trifluoromethyl group, $R^{3b}$ represents a hydrogen atom, and $R^{4c}$ represents a methoxy group, and T represents any substituents indicated in Table 1 to Table 6 (hereinafter, referred to as Compound Class $SX_{18}$).

A compound (L-1) wherein $R^{3c}$ represents a trifluoromethyl group, $R^{3b}$ represents a hydrogen atom, and $R^{4c}$ represents a chlorine atom, and T represents any substituents indicated in Table 1 to Table 6 (hereinafter, referred to as Compound Class $SX_{19}$).

A compound (L-1) wherein $R^{3c}$ represents a trifluoromethyl group, $R^{3b}$ represents a hydrogen atom, and $R^{4c}$ represents a bromine atom, and T represents any substituents indicated in Table 1 to Table 6 (hereinafter, referred to as Compound Class $SX_{20}$).

A compound (L-1) wherein $R^{3c}$ represents a trifluoromethyl group, $R^{3b}$ represents a hydrogen atom, and $R^{4c}$ represents a cyano group, and T represents any substituents indicated in Table 1 to Table 6 (hereinafter, referred to as Compound Class $SX_{21}$).

A compound represented by formula (L-2):

(L-2)

(hereinafter, referred to as compound (L-2)), wherein $R^{3b}$, $R^{3c}$ and $R^{4c}$ represent a hydrogen atom, and T represents any substituents indicated in Table 1 to Table 6 (hereinafter, referred to as Compound Class $SX_{22}$).

A compound (L-2) wherein $R^{3b}$ and $R^{3c}$ a represent hydrogen atom, $R^{4c}$ represents a methyl group, and T represents any substituents indicated in Table 1 to Table 6 (hereinafter, referred to as Compound Class $SX_{23}$).

A compound (L-2) wherein $R^{3b}$ and $R^{3c}$ a represent hydrogen atom, $R^4$ represents an ethyl group, and T represents any substituents indicated in Table 1 to Table 6 (hereinafter, referred to as Compound Class $SX_{24}$).

A compound (L-2) wherein $R^{3b}$ and $R^{3c}$ a represent hydrogen atom, $R^{4c}$ represents a methoxy group, and T represents any substituents indicated in Table 1 to Table 6 (hereinafter, referred to as Compound Class $SX_{25}$).

A compound (L-2) wherein $R^{3b}$ and $R^{3c}$ a represent hydrogen atom, $R^{4c}$ represents a chlorine atom, and T represents any substituents indicated in Table 1 to Table 6 (hereinafter, referred to as Compound Class $SX_{26}$).

A compound (L-2) wherein $R^{3b}$ and $R^{3c}$ a represent hydrogen atom, $R^{4c}$ represents a bromine atom, and T represents any substituents indicated in Table 1 to Table 6 (hereinafter, referred to as Compound Class $SX_{27}$).

A compound (L-2) wherein $R^{3b}$ and $R^{3c}$ a represent hydrogen atom, $R^{4c}$ represents a cyano group, and T represents any substituents indicated in Table 1 to Table 6 (hereinafter, referred to as Compound Class $SX_{28}$).

A compound (L-2) wherein $R^{3b}$ represents a trifluoromethyl group, $R^{3c}$ and $R^{4c}$ represent a hydrogen atom, and T represents any substituents indicated in Table 1 to Table 6 (hereinafter, referred to as Compound Class $SX_{29}$).

A compound (L-2) wherein $R^{3b}$ represents a trifluoromethyl group, $R^{3c}$ represents a hydrogen atom, and $R^{4c}$ represents a methyl group, and T represents any substituents indicated in Table 1 to Table 6 (hereinafter, referred to as Compound Class $SX_{30}$).

A compound (L-2) wherein $R^{3b}$ represents a trifluoromethyl group, $R^{3c}$ represents a hydrogen atom, and $R^{4c}$ represents an ethyl group, and T represents any substituents indicated in Table 1 to Table 6 (hereinafter, referred to as Compound Class $SX_{31}$).

A compound (L-2) wherein $R^{3b}$ represents a trifluoromethyl group, $R^{3c}$ represents a hydrogen atom, and $R^{4c}$ represents a methoxy group, and T represents any substituents indicated in Table 1 to Table 6 (hereinafter, referred to as Compound Class $SX_{32}$).

A compound (L-2) wherein $R^{3b}$ represents a trifluoromethyl group, $R^{3c}$ represents a hydrogen atom, and $R^{4c}$ represents a chlorine atom, and T represents any substituents indicated in Table 1 to Table 6 (hereinafter, referred to as Compound Class $SX_{33}$).

A compound (L-2) wherein $R^{3b}$ represents a trifluoromethyl group, $R^{3c}$ represents a hydrogen atom, and $R^{4c}$ represents a bromine atom, and T represents any substituents indicated in Table 1 to Table 6 (hereinafter, referred to as Compound Class $SX_{34}$).

A compound (L-2) wherein $R^{3b}$ represents a trifluoromethyl group, $R^{3c}$ represents a hydrogen atom, and $R^{4c}$ represents a cyano group, and T represents any substituents indicated in Table 1 to Table 6 (hereinafter, referred to as Compound Class $SX_{35}$).

A compound (L-2) wherein $R^{3c}$ represents a trifluoromethyl group, $R^3$ and $R^{4c}$ represents a hydrogen atom, and T represents any substituents indicated in Table 1 to Table 6 (hereinafter, referred to as Compound Class $SX_{36}$).

A compound (L-2) wherein $R^{3c}$ represents a trifluoromethyl group, $R^{3b}$ represents a hydrogen atom, and $R^{4c}$ represents a methyl group, and T represents any substituents indicated in Table 1 to Table 6 (hereinafter, referred to as Compound Class $SX_{37}$).

A compound (L-2) wherein $R^{3c}$ represents a trifluoromethyl group, $R^{3b}$ represents a hydrogen atom, and $R^{4c}$ represents an ethyl group, and T represents any substituents indicated in Table 1 to Table 6 (hereinafter, referred to as Compound Class $SX_{38}$).

A compound (L-2) wherein $R^{3c}$ represents a trifluoromethyl group, $R^{3b}$ represents a hydrogen atom, and $R^{4c}$ represents a methoxy group, and T represents any substituents indicated in Table 1 to Table 6 (hereinafter, referred to as Compound Class $SX_{39}$).

A compound (L-2) wherein $R^{3c}$ represents a trifluoromethyl group, $R^{3b}$ represents a hydrogen atom, and $R^{4c}$ represents a chlorine atom, and T represents any substituents indicated in Table 1 to Table 6 (hereinafter, referred to as Compound Class $SX_{40}$).

A compound (L-2) wherein $R^{3c}$ represents a trifluoromethyl group, $R^{3b}$ represents a hydrogen atom, and $R^{4c}$ represents a bromine atom, and T represents any substituents indicated in Table 1 to Table 6 (hereinafter, referred to as Compound Class $SX_{41}$).

A compound (L-2) wherein $R^{3c}$ represents a trifluoromethyl group, $R^{3b}$ represents a hydrogen atom, and $R^{4c}$ represents a cyano group, and T represents any substituents indicated in Table 1 to Table 6 (hereinafter, referred to as Compound Class $SX_{42}$).

A compound represented by formula (L-3):

(L-3)

(hereinafter, referred to as compound (L-3)), wherein $R^{3b}$, $R^{3c}$ and $R^{4c}$ represent a hydrogen atom, and T represents any substituents indicated in Table 1 to Table 6 (hereinafter, referred to as Compound Class $SX_{43}$).

A compound (L-3) wherein $R^{3b}$ and $R^{3c}$ a represent hydrogen atom, $R^{4c}$ represents a methyl group, and T represents any substituents indicated in Table 1 to Table 6 (hereinafter, referred to as Compound Class $SX_{44}$).

A compound (L-3) wherein $R^{3b}$ and $R^{3c}$ a represent hydrogen atom, $R^{4c}$ represents an ethyl group, and T represents any substituents indicated in Table 1 to Table 6 (hereinafter, referred to as Compound Class $SX_{45}$).

A compound (L-3) wherein $R^{3b}$ and $R^{3c}$ a represent hydrogen atom, $R^{4c}$ represents a methoxy group, and T represents any substituents indicated in Table 1 to Table 6 (hereinafter, referred to as Compound Class $SX_{46}$).

A compound (L-3) wherein $R^{3b}$ and $R^{3c}$ a represent hydrogen atom, $R^{4c}$ represents a chlorine atom, and T represents any substituents indicated in Table 1 to Table 6 (hereinafter, referred to as Compound Class $SX_{47}$).

A compound (L-3) wherein $R^{3b}$ and $R^{3c}$ a represent hydrogen atom, $R^{4c}$ represents a bromine atom, and T represents any substituents indicated in Table 1 to Table 6 (hereinafter, referred to as Compound Class $SX_{48}$).

A compound (L-3) wherein $R^{3b}$ and $R^{3c}$ a represent hydrogen atom, $R^{4c}$ represents a cyano group, and T represents any substituents indicated in Table 1 to Table 6 (hereinafter, referred to as Compound Class $SX_{49}$).

A compound (L-3) wherein $R^{3b}$ represents a trifluoromethyl group, $R^{3c}$ and $R^{4c}$ represent a hydrogen atom, and T represents any substituents indicated in Table 1 to Table 6 (hereinafter, referred to as Compound Class $SX_{50}$).

A compound (L-3) wherein $R^{3b}$ represents a trifluoromethyl group, $R^{3c}$ represents a hydrogen atom, and $R^{4c}$ represents a methyl group, and T represents any substituents indicated in Table 1 to Table 6 (hereinafter, referred to as Compound Class $SX_{51}$).

A compound (L-3) wherein $R^{3b}$ represents a trifluoromethyl group, $R^{3c}$ represents a hydrogen atom, and $R^{4c}$ represents an ethyl group, and T represents any substituents indicated in Table 1 to Table 6 (hereinafter, referred to as Compound Class $SX_{52}$).

A compound (L-3) wherein $R^{3b}$ represents a trifluoromethyl group, $R^{3c}$ represents a hydrogen atom, and $R^{4c}$ represents a methoxy group, and T represents any substituents indicated in Table 1 to Table 6 (hereinafter, referred to as Compound Class $SX_{53}$).

A compound (L-3) wherein $R^{3b}$ represents a trifluoromethyl group, $R^{3c}$ represents a hydrogen atom, and $R^{4c}$ represents a chlorine atom, and T represents any substituents indicated in Table 1 to Table 6 (hereinafter, referred to as Compound Class $SX_{54}$).

A compound (L-3) wherein $R^{3b}$ represents a trifluoromethyl group, $R^{3c}$ represents a hydrogen atom, and $R^{4c}$ represents a bromine atom, and T represents any substituents indicated in Table 1 to Table 6 (hereinafter, referred to as Compound Class $SX_{55}$).

A compound (L-3) wherein $R^{3b}$ represents a trifluoromethyl group, $R^{3c}$ represents a hydrogen atom, and $R^{4c}$ represents a cyano group, and T represents any substituents indicated in Table 1 to Table 6 (hereinafter, referred to as Compound Class $SX_{56}$).

A compound (L-3) wherein $R^{3c}$ represents a trifluoromethyl group, $R^3$ and $R^{4c}$ represents a hydrogen atom, and T represents any substituents indicated in Table 1 to Table 6 (hereinafter, referred to as Compound Class $SX_{57}$).

A compound (L-3) wherein $R^{3c}$ represents a trifluoromethyl group, $R^{3b}$ represents a hydrogen atom, and $R^{4c}$ represents a methyl group, and T represents any substituents indicated in Table 1 to Table 6 (hereinafter, referred to as Compound Class $SX_{58}$).

A compound (L-3) wherein $R^{3c}$ represents a trifluoromethyl group, $R^{3b}$ represents a hydrogen atom, and $R^{4c}$ represents an ethyl group, and T represents any substituents indicated in Table 1 to Table 6 (hereinafter, referred to as Compound Class $SX_{59}$).

A compound (L-3) wherein $R^{3c}$ represents a trifluoromethyl group, $R^{3b}$ represents a hydrogen atom, and $R^{4c}$ represents a methoxy group, and T represents any substituents indicated in Table 1 to Table 6 (hereinafter, referred to as Compound Class $SX_{60}$).

A compound (L-3) wherein $R^{3c}$ represents a trifluoromethyl group, $R^{3b}$ represents a hydrogen atom, and $R^{4c}$ represents a chlorine atom, and T represents any substituents indicated in Table 1 to Table 6 (hereinafter, referred to as Compound Class $SX_{61}$).

A compound (L-3) wherein $R^{3c}$ represents a trifluoromethyl group, $R^{3b}$ represents a hydrogen atom, and $R^{4c}$ represents a bromine atom, and T represents any substituents indicated in Table 1 to Table 6 (hereinafter, referred to as Compound Class $SX_{62}$).

A compound (L-3) wherein $R^{3c}$ represents a trifluoromethyl group, $R^{3b}$ represents a hydrogen atom, and $R^{4c}$ represents a cyano group, and T represents any substituents indicated in Table 1 to Table 6 (hereinafter, referred to as Compound Class $SX_{63}$).

A compound represented by formula (L-4):

(L-4)

(hereinafter, referred to as compound (L-4)), wherein $R^{3b}$, $R^{3c}$ and $R^{4c}$ represent a hydrogen atom, and T represents any substituents indicated in Table 1 to Table 6 (hereinafter, referred to as Compound Class $SX_{64}$).

A compound (L-4) wherein $R^{3b}$ and $R^{3c}$ a represent hydrogen atom, $R^{4c}$ represents a methyl group, and T represents any substituents indicated in Table 1 to Table 6 (hereinafter, referred to as Compound Class $SX_{65}$).

A compound (L-4) wherein $R^{3b}$ and $R^{3c}$ a represent hydrogen atom, $R^{4c}$ represents an ethyl group, and T represents any substituents indicated in Table 1 to Table 6 (hereinafter, referred to as Compound Class $SX_{66}$).

A compound (L-4) wherein $R^{3b}$ and $R^{3c}$ a represent hydrogen atom, $R^{4c}$ represents a methoxy group, and T represents any substituents indicated in Table 1 to Table 6 (hereinafter, referred to as Compound Class $SX_{67}$).

A compound (L-4) wherein $R^{3b}$ and $R^{3c}$ a represent hydrogen atom, $R^{4c}$ represents a chlorine atom, and T represents any substituents indicated in Table 1 to Table 6 (hereinafter, referred to as Compound Class $SX_{68}$).

A compound (L-4) wherein $R^{3b}$ and $R^{3c}$ a represent hydrogen atom, $R^{4c}$ represents a bromine atom, and T represents any substituents indicated in Table 1 to Table 6 (hereinafter, referred to as Compound Class $SX_{69}$).

A compound (L-4) wherein $R^{3b}$ and $R^{3c}$ a represent hydrogen atom, $R^{4c}$ represents a cyano group, and T represents any substituents indicated in Table 1 to Table 6 (hereinafter, referred to as Compound Class $SX_{70}$).

A compound (L-4) wherein $R^{3b}$ represents a trifluoromethyl group, $R^{3c}$ and $R^{4c}$ represent a hydrogen atom, and T represents any substituents indicated in Table 1 to Table 6 (hereinafter, referred to as Compound Class $SX_{71}$).

A compound (L-4) wherein $R^{3b}$ represents a trifluoromethyl group, $R^{3c}$ represents a hydrogen atom, and $R^{4c}$ represents a methyl group, and T represents any substituents indicated in Table 1 to Table 6 (hereinafter, referred to as Compound Class $SX_{72}$).

A compound (L-4) wherein $R^{3b}$ represents a trifluoromethyl group, $R^{3c}$ represents a hydrogen atom, and $R^{4c}$ represents an ethyl group, and T represents any substituents indicated in Table 1 to Table 6 (hereinafter, referred to as Compound Class $SX_{73}$).

A compound (L-4) wherein $R^{3b}$ represents a trifluoromethyl group, $R^{3c}$ represents a hydrogen atom, and $R^{4c}$ represents a methoxy group, and T represents any substituents indicated in Table 1 to Table 6 (hereinafter, referred to as Compound Class $SX_{74}$).

A compound (L-4) wherein $R^{3b}$ represents a trifluoromethyl group, $R^{3c}$ represents a hydrogen atom, and $R^{4c}$ represents a chlorine atom, and T represents any substituents indicated in Table 1 to Table 6 (hereinafter, referred to as Compound Class $SX_{75}$).

A compound (L-4) wherein $R^{3b}$ represents a trifluoromethyl group, $R^{3c}$ represents a hydrogen atom, and $R^{4c}$ represents a bromine atom, and T represents any substituents indicated in Table 1 to Table 6 (hereinafter, referred to as Compound Class $SX_{76}$).

A compound (L-4) wherein $R^{3b}$ represents a trifluoromethyl group, $R^{3c}$ represents a hydrogen atom, and $R^{4c}$ represents a cyano group, and T represents any substituents indicated in Table 1 to Table 6 (hereinafter, referred to as Compound Class $SX_{77}$).

A compound (L-4) wherein $R^{3c}$ represents a trifluoromethyl group, $R^{3b}$ and $R^{4c}$ represents a hydrogen atom, and T represents any substituents indicated in Table 1 to Table 6 (hereinafter, referred to as Compound Class $SX_{78}$).

A compound (L-4) wherein $R^{3c}$ represents a trifluoromethyl group, $R^{3b}$ represents a hydrogen atom, and $R^{4c}$ represents a methyl group, and T represents any substituents indicated in Table 1 to Table 6 (hereinafter, referred to as Compound Class $SX_{79}$).

A compound (L-4) wherein $R^{3c}$ represents a trifluoromethyl group, $R^{3b}$ represents a hydrogen atom, and $R^{4c}$ represents an ethyl group, and T represents any substituents indicated in Table 1 to Table 6 (hereinafter, referred to as Compound Class $SX_{80}$).

A compound (L-4) wherein $R^{3c}$ represents a trifluoromethyl group, $R^{3b}$ represents a hydrogen atom, and $R^{4c}$ represents a methoxy group, and T represents any substituents indicated in Table 1 to Table 6 (hereinafter, referred to as Compound Class $SX_{81}$).

A compound (L-4) wherein $R^{3c}$ represents a trifluoromethyl group, $R^{3b}$ represents a hydrogen atom, and $R^{4c}$ represents a chlorine atom, and T represents any substituents indicated in Table 1 to Table 6 (hereinafter, referred to as Compound Class $SX_{82}$).

A compound (L-4) wherein $R^{3c}$ represents a trifluoromethyl group, $R^{3b}$ represents a hydrogen atom, and $R^{4c}$ represents a bromine atom, and T represents any substituents indicated in Table 1 to Table 6 (hereinafter, referred to as Compound Class $SX_{83}$).

A compound (L-4) wherein $R^{3c}$ represents a trifluoromethyl group, $R^{3b}$ represents a hydrogen atom, and $R^{4c}$ represents a cyano group, and T represents any substituents indicated in Table 1 to Table 6 (hereinafter, referred to as Compound Class $SX_{84}$).

A compound represented by formula (L-5):

(L-5)

(hereinafter, referred to as compound (L-5)), wherein $R^{3b}$, $R^{3c}$ and $R^{4c}$ represent a hydrogen atom, and T represents any substituents indicated in Table 1 to Table 6 (hereinafter, referred to as Compound Class $SX_{85}$).

A compound (L-5) wherein $R^{3b}$ and $R^{3c}$ a represent hydrogen atom, $R^{4c}$ represents a methyl group, and T represents any substituents indicated in Table 1 to Table 6 (hereinafter, referred to as Compound Class $SX_{86}$).

A compound (L-5) wherein $R^{3b}$ and $R^{3c}$ a represent hydrogen atom, $R^{4c}$ represents an ethyl group, and T represents any substituents indicated in Table 1 to Table 6 (hereinafter, referred to as Compound Class $SX_{87}$).

A compound (L-5) wherein $R^{3b}$ and $R^{3c}$ a represent hydrogen atom, $R^{4c}$ represents a methoxy group, and T represents any substituents indicated in Table 1 to Table 6 (hereinafter, referred to as Compound Class $SX_{88}$).

A compound (L-5) wherein $R^{3b}$ and $R^{3c}$ a represent hydrogen atom, $R^{4c}$ represents a chlorine atom, and T represents any substituents indicated in Table 1 to Table 6 (hereinafter, referred to as Compound Class $SX_{89}$).

A compound (L-5) wherein $R^{3b}$ and $R^{3c}$ a represent hydrogen atom, $R^{4c}$ represents a bromine atom, and T represents any substituents indicated in Table 1 to Table 6 (hereinafter, referred to as Compound Class $SX_{90}$).

A compound (L-5) wherein $R^{3b}$ and $R^{3c}$ a represent hydrogen atom, $R^{4c}$ represents a cyano group, and T represents any substituents indicated in Table 1 to Table 6 (hereinafter, referred to as Compound Class $SX_{91}$).

A compound (L-5) wherein $R^{3b}$ represents a trifluoromethyl group, $R^{3c}$ and $R^{4c}$ represent a hydrogen atom, and T represents any substituents indicated in Table 1 to Table 6 (hereinafter, referred to as Compound Class $SX_{92}$).

A compound (L-5) wherein $R^{3b}$ represents a trifluoromethyl group, $R^{3c}$ represents a hydrogen atom, and $R^{4c}$ represents a methyl group, and T represents any substituents indicated in Table 1 to Table 6 (hereinafter, referred to as Compound Class $SX_{93}$).

A compound (L-5) wherein $R^{3b}$ represents a trifluoromethyl group, $R^{3c}$ represents a hydrogen atom, and $R^{4c}$ represents an ethyl group, and T represents any substituents indicated in Table 1 to Table 6 (hereinafter, referred to as Compound Class $SX_{94}$).

A compound (L-5) wherein $R^{3b}$ represents a trifluoromethyl group, $R^{3c}$ represents a hydrogen atom, and $R^{4c}$ represents a methoxy group, and T represents any substituents indicated in Table 1 to Table 6 (hereinafter, referred to as Compound Class $SX_{95}$).

A compound (L-5) wherein $R^{3b}$ represents a trifluoromethyl group, $R^{3c}$ represents a hydrogen atom, and $R^{4c}$ represents a chlorine atom, and T represents any substituents indicated in Table 1 to Table 6 (hereinafter, referred to as Compound Class $SX_{96}$).

A compound (L-5) wherein $R^{3b}$ represents a trifluoromethyl group, $R^{3c}$ represents a hydrogen atom, and $R^{4c}$ represents a bromine atom, and T represents any substituents indicated in Table 1 to Table 6 (hereinafter, referred to as Compound Class $SX_{97}$).

A compound (L-5) wherein $R^{3b}$ represents a trifluoromethyl group, $R^{3c}$ represents a hydrogen atom, and $R^{4c}$ represents a cyano group, and T represents any substituents indicated in Table 1 to Table 6 (hereinafter, referred to as Compound Class $SX_{98}$).

A compound (L-5) wherein $R^{3c}$ represents a trifluoromethyl group, $R^{3b}$ and $R^{4c}$ represents a hydrogen atom, and T represents any substituents indicated in Table 1 to Table 6 (hereinafter, referred to as Compound Class $SX_{99}$).

A compound (L-5) wherein $R^{3c}$ represents a trifluoromethyl group, $R^{3b}$ represents a hydrogen atom, and $R^{4c}$ represents a methyl group, and T represents any substituents indicated in Table 1 to Table 6 (hereinafter, referred to as Compound Class $SX_{100}$).

A compound (L-5) wherein $R^{3c}$ represents a trifluoromethyl group, $R^{3b}$ represents a hydrogen atom, and $R^{4c}$ represents an ethyl group, and T represents any substituents indicated in Table 1 to Table 6 (hereinafter, referred to as Compound Class $SX_{101}$).

A compound (L-5) wherein $R^{3c}$ represents a trifluoromethyl group, $R^{3b}$ represents a hydrogen atom, and $R^{4c}$ represents a methoxy group, and T represents any substituents indicated in Table 1 to Table 6 (hereinafter, referred to as Compound Class $SX_{102}$).

A compound (L-5) wherein $R^{3c}$ represents a trifluoromethyl group, $R^{3b}$ represents a hydrogen atom, and $R^{4c}$ represents a chlorine atom, and T represents any substituents indicated in Table 1 to Table 6 (hereinafter, referred to as Compound Class $SX_{103}$).

A compound (L-5) wherein $R^{3c}$ represents a trifluoromethyl group, $R^{3b}$ represents a hydrogen atom, and $R^{4c}$ represents a bromine atom, and T represents any substituents indicated in Table 1 to Table 6 (hereinafter, referred to as Compound Class $SX_{104}$).

A compound (L-5) wherein $R^{3c}$ represents a trifluoromethyl group, $R^{3b}$ represents a hydrogen atom, and $R^{4c}$ represents a cyano group, and T represents any substituents indicated in Table 1 to Table 6 (hereinafter, referred to as Compound Class $SX_{105}$).

A compound represented by formula (L-6):

(L-6)

(hereinafter, referred to as compound (L-6)), wherein Rb, $R^{3c}$ and $R^{4c}$ represent a hydrogen atom, and T represents any substituents indicated in Table 1 to Table 6 (hereinafter, referred to as Compound Class $SX_{106}$).

A compound (L-6) wherein $R^{3b}$ and $R^{3c}$ a represent hydrogen atom, $R^{4c}$ represents a methyl group, and T represents any substituents indicated in Table 1 to Table 6 (hereinafter, referred to as Compound Class $SX_{107}$).

A compound (L-6) wherein $R^{3b}$ and $R^{3c}$ a represent hydrogen atom, $R^{4c}$ represents an ethyl group, and T represents any substituents indicated in Table 1 to Table 6 (hereinafter, referred to as Compound Class $SX_{108}$).

A compound (L-6) wherein $R^{3b}$ and $R^{3c}$ a represent hydrogen atom, $R^{4c}$ represents a methoxy group, and T represents any substituents indicated in Table 1 to Table 6 (hereinafter, referred to as Compound Class $SX_{109}$).

A compound (L-6) wherein $R^{3b}$ and $R^{3c}$ a represent hydrogen atom, $R^{4c}$ represents a chlorine atom, and T represents any substituents indicated in Table 1 to Table 6 (hereinafter, referred to as Compound Class $SX_{110}$).

A compound (L-6) wherein $R^{3b}$ and $R^{3c}$ a represent hydrogen atom, $R^{4c}$ represents a bromine atom, and T represents any substituents indicated in Table 1 to Table 6 (hereinafter, referred to as Compound Class $SX_{111}$).

A compound (L-6) wherein $R^{3b}$ and $R^{3c}$ a represent hydrogen atom, $R^{4c}$ represents a cyano group, and T represents any substituents indicated in Table 1 to Table 6 (hereinafter, referred to as Compound Class $SX_{112}$).

A compound (L-6) wherein $R^{3b}$ represents a trifluoromethyl group, $R^{3c}$ and $R^{4c}$ represent a hydrogen atom, and T represents any substituents indicated in Table 1 to Table 6 (hereinafter, referred to as Compound Class $SX_{113}$).

A compound (L-6) wherein $R^{3b}$ represents a trifluoromethyl group, $R^{3c}$ represents a hydrogen atom, and $R^{4c}$ represents a methyl group, and T represents any substituents indicated in Table 1 to Table 6 (hereinafter, referred to as Compound Class $SX_{114}$).

A compound (L-6) wherein $R^{3b}$ represents a trifluoromethyl group, $R^{3c}$ represents a hydrogen atom, and $R^{4c}$ represents an ethyl group, and T represents any substituents indicated in Table 1 to Table 6 (hereinafter, referred to as Compound Class $SX_{115}$).

A compound (L-6) wherein $R^{3b}$ represents a trifluoromethyl group, $R^{3c}$ represents a hydrogen atom, and $R^{4c}$ represents a methoxy group, and T represents any substituents indicated in Table 1 to Table 6 (hereinafter, referred to as Compound Class $SX_{116}$).

A compound (L-6) wherein $R^{3b}$ represents a trifluoromethyl group, $R^{3c}$ represents a hydrogen atom, and $R^{4c}$ represents a chlorine atom, and T represents any substituents indicated in Table 1 to Table 6 (hereinafter, referred to as Compound Class $SX_{117}$).

A compound (L-6) wherein $R^{3b}$ represents a trifluoromethyl group, $R^{3c}$ represents a hydrogen atom, and $R^{4c}$ represents a bromine atom, and T represents any substituents indicated in Table 1 to Table 6 (hereinafter, referred to as Compound Class $SX_{118}$).

A compound (L-6) wherein $R^{3b}$ represents a trifluoromethyl group, $R^{3c}$ represents a hydrogen atom, and $R^{4c}$ represents a cyano group, and T represents any substituents indicated in Table 1 to Table 6 (hereinafter, referred to as Compound Class $SX_{119}$).

A compound (L-6) wherein $R^{3c}$ represents a trifluoromethyl group, $R^{3b}$ and $R^{4c}$ represents a hydrogen atom, and T represents any substituents indicated in Table 1 to Table 6 (hereinafter, referred to as Compound Class $SX_{120}$).

A compound (L-6) wherein $R^{3c}$ represents a trifluoromethyl group, $R^{3b}$ represents a hydrogen atom, and $R^{4c}$ represents a methyl group, and T represents any substituents indicated in Table 1 to Table 6 (hereinafter, referred to as Compound Class $SX_{121}$).

A compound (L-6) wherein $R^{3c}$ represents a trifluoromethyl group, $R^{3b}$ represents a hydrogen atom, and $R^{4c}$ represents an ethyl group, and T represents any substituents indicated in Table 1 to Table 6 (hereinafter, referred to as Compound Class $SX_{122}$).

A compound (L-6) wherein $R^{3c}$ represents a trifluoromethyl group, $R^{3b}$ represents a hydrogen atom, and $R^{4c}$ represents a methoxy group, and T represents any substituents indicated in Table 1 to Table 6 (hereinafter, referred to as Compound Class $SX_{123}$).

A compound (L-6) wherein $R^{3c}$ represents a trifluoromethyl group, $R^{3b}$ represents a hydrogen atom, and $R^{4c}$ represents a chlorine atom, and T represents any substituents indicated in Table 1 to Table 6 (hereinafter, referred to as Compound Class $SX_{124}$).

A compound (L-6) wherein $R^{3c}$ represents a trifluoromethyl group, $R^{3b}$ represents a hydrogen atom, and $R^{4c}$ represents a bromine atom, and T represents any substituents indicated in Table 1 to Table 6 (hereinafter, referred to as Compound Class $SX_{125}$).

A compound (L-6) wherein $R^{3c}$ represents a trifluoromethyl group, $R^{3b}$ represents a hydrogen atom, and $R^{4c}$ represents a cyano group, and T represents any substituents indicated in Table 1 to Table 6 (hereinafter, referred to as Compound Class $SX_{126}$).

A compound represented by formula (L-7):

(hereinafter, referred to as compound (L-7)), wherein $G^1$ represents C1, $R^{3b}$ and $R^{4c}$ represent a hydrogen atom, and T represents any substituents indicated in Table 1 to Table 6 (hereinafter, referred to as Compound Class $SX_{127}$).

A compound (L-7) wherein $G^1$ represents CH, $R^{3b}$ represents a hydrogen atom, $R^{4c}$ represents a methyl group, and T represents any substituents indicated in Table 1 to Table 6 (hereinafter, referred to as Compound Class $SX_{128}$).

A compound (L-7) wherein $G^1$ represents CH, $R^{3b}$ represents a hydrogen atom, $R^{4c}$ represents an ethyl group, and T represents any substituents indicated in Table 1 to Table 6 (hereinafter, referred to as Compound Class $SX_{129}$).

A compound (L-7) wherein $G^1$ represents CH, $R^{3b}$ represents a hydrogen atom, $R^{4c}$ represents a methoxy group, and T represents any substituents indicated in Table 1 to Table 6 (hereinafter, referred to as Compound Class $SX_{130}$).

A compound (L-7) wherein $G^1$ represents CH, $R^{3b}$ represents a hydrogen atom, $R^{4c}$ represents a chlorine atom, and T represents any substituents indicated in Table 1 to Table 6 (hereinafter, referred to as Compound Class $SX_{131}$).

A compound (L-7) wherein $G^1$ represents CH, $R^{3b}$ represents a hydrogen atom, $R^{4c}$ represents a bromine atom, and T represents any substituents indicated in Table 1 to Table 6 (hereinafter, referred to as Compound Class $SX_{132}$).

A compound (L-7) wherein $G^1$ represents CH, $R^{3b}$ represents a hydrogen atom, $R^{4c}$ represents a cyano group, and T represents any substituents indicated in Table 1 to Table 6 (hereinafter, referred to as Compound Class $SX_{133}$).

A compound (L-7) wherein $G^1$ represents CH, $R^{3b}$ represents a hydrogen atom, $R^{4c}$ represents a hydrogen atom, and T represents any substituents indicated in Table 1 to Table 6 (hereinafter, referred to as Compound Class $SX_{134}$).

A compound (L-7) wherein $G^1$ represents CH, $R^{3b}$ represents a hydrogen atom, $R^{4c}$ represents a methyl group, and T represents any substituents indicated in Table 1 to Table 6 (hereinafter, referred to as Compound Class $SX_{135}$).

A compound (L-7) wherein $G^1$ represents CH, $R^{3b}$ represents a hydrogen atom, $R^{4c}$ represents an ethyl group, and T represents any substituents indicated in Table 1 to Table 6 (hereinafter, referred to as Compound Class $SX_{136}$).

A compound (L-7) wherein $G^1$ represents CH, $R^{3b}$ represents a hydrogen atom, $R^{4c}$ represents a methoxy group, and T represents any substituents indicated in Table 1 to Table 6 (hereinafter, referred to as Compound Class $SX_{137}$).

A compound (L-7) wherein $G^1$ represents CH, $R^{3b}$ represents a hydrogen atom, $R^{4c}$ represents a chlorine atom, and T represents any substituents indicated in Table 1 to Table 6 (hereinafter, referred to as Compound Class $SX_{138}$).

A compound (L-7) wherein $G^1$ represents CH, $R^{3b}$ represents a hydrogen atom, $R^{4c}$ represents a bromine atom, and T represents any substituents indicated in Table 1 to Table 6 (hereinafter, referred to as Compound Class $SX_{139}$).

A compound (L-7) wherein $G^1$ represents CH, $R^{3b}$ represents a hydrogen atom, $R^{4c}$ represents a cyano group, and T represents any substituents indicated in Table 1 to Table 6 (hereinafter, referred to as Compound Class $SX_{140}$).

A compound (L-7) wherein $G^1$ represents a nitrogen atom, $R^{3b}$ and $R^{4c}$ represent a hydrogen atom, and T represents any substituents indicated in Table 1 to Table 6 (hereinafter, referred to as Compound Class $SX_{141}$).

A compound (L-7) wherein $G^1$ represents a nitrogen atom, $R^{3b}$ represents a hydrogen atom, $R^{4c}$ represents a methyl group, and T represents any substituents indicated in Table 1 to Table 6 (hereinafter, referred to as Compound Class $SX_{142}$).

A compound (L-7) wherein $G^1$ represents a nitrogen atom, $R^{3b}$ represents a hydrogen atom, $R^{4c}$ represents an ethyl group, and T represents any substituents indicated in Table 1 to Table 6 (hereinafter, referred to as Compound Class $SX_{143}$).

A compound (L-7) wherein $G^1$ represents a nitrogen atom, $R^{3b}$ represents a hydrogen atom, $R^{4c}$ represents a methoxy group, and T represents any substituents indicated in Table 1 to Table 6 (hereinafter, referred to as Compound Class $SX_{144}$).

A compound (L-7) wherein $G^1$ represents a nitrogen atom, $R^{3b}$ represents a hydrogen atom, $R^{4c}$ represents a chlorine atom, and T represents any substituents indicated in Table 1 to Table 6 (hereinafter, referred to as Compound Class $SX_{145}$).

A compound (L-7) wherein $G^1$ represents a nitrogen atom, $R^{3b}$ represents a hydrogen atom, $R^{4c}$ represents a bromine atom, and T represents any substituents indicated in Table 1 to Table 6 (hereinafter, referred to as Compound Class $SX_{146}$).

A compound (L-7) wherein $G^1$ represents a nitrogen atom, $R^{3b}$ represents a hydrogen atom, $R^{4c}$ represents a cyano group, and T represents any substituents indicated in Table 1 to Table 6 (hereinafter, referred to as Compound Class $SX_{147}$).

A compound (L-7) wherein $G^1$ represents a nitrogen atom, $R^{3b}$ represents a trifluoromethyl group, $R^{4c}$ represents a hydrogen atom, and T represents any substituents indicated in Table 1 to Table 6 (hereinafter, referred to as Compound Class $SX_{148}$).

A compound (L-7) wherein $G^1$ represents a nitrogen atom, $R^{3b}$ represents a trifluoromethyl group, $R^{4c}$ represents a methyl group, and T represents any substituents indicated in Table 1 to Table 6 (hereinafter, referred to as Compound Class $SX_{149}$).

A compound (L-7) wherein $G^1$ represents a nitrogen atom, $R^{3b}$ represents a trifluoromethyl group, $R^{4c}$ represents an ethyl group, and T represents any substituents indicated in Table 1 to Table 6 (hereinafter, referred to as Compound Class $SX_{150}$).

A compound (L-7) wherein $G^1$ represents a nitrogen atom, $R^{3b}$ represents a trifluoromethyl group, $R^{4c}$ represents a methoxy group, and T represents any substituents indicated in Table 1 to Table 6 (hereinafter, referred to as Compound Class $SX_{151}$).

A compound (L-7) wherein $G^1$ represents a nitrogen atom, $R^{3b}$ represents a trifluoromethyl group, $R^{4c}$ represents a chlorine atom, and T represents any substituents indicated in Table 1 to Table 6 (hereinafter, referred to as Compound Class $SX_{152}$).

A compound (L-7) wherein $G^1$ represents a nitrogen atom, $R^{3b}$ represents a trifluoromethyl group, $R^{4c}$ represents a bromine atom, and T represents any substituents indicated in Table 1 to Table 6 (hereinafter, referred to as Compound Class $SX_{153}$).

A compound (L-7) wherein $G^1$ represents a nitrogen atom, $R^{3b}$ represents a trifluoromethyl group, $R^{4c}$ represents a cyano group, and T represents any substituents indicated in Table 1 to Table 6 (hereinafter, referred to as Compound Class $SX_{154}$).

A compound represented by formula (L-8):

(hereinafter, referred to as compound (L-8)), wherein $G^1$ represents CH, $R^{3b}$ and $R^{4c}$ represent a hydrogen atom, and T represents any substituents indicated in Table 1 to Table 6 (hereinafter, referred to as Compound Class $SX_{155}$).

A compound (L-8) wherein $G^1$ represents CH, $R^{3b}$ represents a hydrogen atom, $R^{4c}$ represents a methyl group, and T represents any substituents indicated in Table 1 to Table 6 (hereinafter, referred to as Compound Class $SX_{156}$).

A compound (L-8) wherein $G^1$ represents CH, $R^{3b}$ represents a hydrogen atom, $R^{4c}$ represents an ethyl group, and T represents any substituents indicated in Table 1 to Table 6 (hereinafter, referred to as Compound Class $SX_{157}$).

A compound (L-8) wherein $G^1$ represents CH, $R^{3b}$ represents a hydrogen atom, $R^{4c}$ represents a methoxy group, and T represents any substituents indicated in Table 1 to Table 6 (hereinafter, referred to as Compound Class $SX_{158}$).

A compound (L-8) wherein $G^1$ represents CH, $R^{3b}$ represents a hydrogen atom, $R^{4c}$ represents a chlorine atom, and T represents any substituents indicated in Table 1 to Table 6 (hereinafter, referred to as Compound Class $SX_{159}$).

A compound (L-8) wherein $G^1$ represents CH, $R^{3b}$ represents a hydrogen atom, $R^{4c}$ represents a bromine atom, and T represents any substituents indicated in Table 1 to Table 6 (hereinafter, referred to as Compound Class $SX_{160}$).

A compound (L-8) wherein $G^1$ represents CH, $R^{3b}$ represents a hydrogen atom, $R^{4c}$ represents a cyano group, and T represents any substituents indicated in Table 1 to Table 6 (hereinafter, referred to as Compound Class $SX_{161}$).

A compound (L-8) wherein $G^1$ represents CH, $R^{3b}$ represents a hydrogen atom, $R^{4c}$ represents a hydrogen atom, and T represents any substituents indicated in Table 1 to Table 6 (hereinafter, referred to as Compound Class $SX_{162}$).

A compound (L-8) wherein $G^1$ represents CH, $R^{3b}$ represents a hydrogen atom, $R^{4c}$ represents a methyl group, and T represents any substituents indicated in Table 1 to Table 6 (hereinafter, referred to as Compound Class $SX_{163}$).

A compound (L-8) wherein $G^1$ represents CH, $R^{3b}$ represents a hydrogen atom, $R^{4c}$ represents an ethyl group, and T represents any substituents indicated in Table 1 to Table 6 (hereinafter, referred to as Compound Class $SX_{164}$).

A compound (L-8) wherein $G^1$ represents CH, $R^{3b}$ represents a hydrogen atom, $R^{4c}$ represents a methoxy group, and T represents any substituents indicated in Table 1 to Table 6 (hereinafter, referred to as Compound Class $SX_{165}$).

A compound (L-8) wherein $G^1$ represents CH, $R^{3b}$ represents a hydrogen atom, $R^{4c}$ represents a chlorine atom, and T represents any substituents indicated in Table 1 to Table 6 (hereinafter, referred to as Compound Class $SX_{166}$).

A compound (L-8) wherein $G^1$ represents CH, $R^{3b}$ represents a hydrogen atom, $R^{4c}$ represents a bromine atom, and T represents any substituents indicated in Table 1 to Table 6 (hereinafter, referred to as Compound Class $SX_{167}$).

A compound (L-8) wherein $G^1$ represents CH, $R^{3b}$ represents a hydrogen atom, $R^{4c}$ represents a cyano group, and T represents any substituents indicated in Table 1 to Table 6 (hereinafter, referred to as Compound Class $SX_{168}$).

A compound (L-8) wherein $G^1$ represents a nitrogen atom, $R^{3b}$ and $R^{4c}$ represent a hydrogen atom, and T represents any substituents indicated in Table 1 to Table 6 (hereinafter, referred to as Compound Class $SX_{169}$).

A compound (L-8) wherein $G^1$ represents a nitrogen atom, $R^{3b}$ represents a hydrogen atom, $R^{4c}$ represents a methyl group, and T represents any substituents indicated in Table 1 to Table 6 (hereinafter, referred to as Compound Class $SX_{170}$).

A compound (L-8) wherein $G^1$ represents a nitrogen atom, $R^{3b}$ represents a hydrogen atom, $R^{4c}$ represents an ethyl group, and T represents any substituents indicated in Table 1 to Table 6 (hereinafter, referred to as Compound Class $SX_{171}$).

A compound (L-8) wherein $G^1$ represents a nitrogen atom, $R^{3b}$ represents a hydrogen atom, $R^{4c}$ represents a methoxy group, and T represents any substituents indicated in Table 1 to Table 6 (hereinafter, referred to as Compound Class $SX_{172}$).

A compound (L-7) wherein $G^1$ represents a nitrogen atom, $R^{3b}$ represents a hydrogen atom, $R^{4c}$ represents a chlorine atom, and T represents any substituents indicated in Table 1 to Table 6 (hereinafter, referred to as Compound Class $SX_{173}$).

A compound (L-8) wherein $G^1$ represents a nitrogen atom, $R^{3b}$ represents a hydrogen atom, $R^{4c}$ represents a bromine atom, and T represents any substituents indicated in Table 1 to Table 6 (hereinafter, referred to as Compound Class $SX_{174}$).

A compound (L-8) wherein $G^1$ represents a nitrogen atom, $R^{3b}$ represents a hydrogen atom, $R^{4c}$ represents a cyano group, and T represents any substituents indicated in Table 1 to Table 6 (hereinafter, referred to as Compound Class $SX_{175}$).

A compound (L-8) wherein $G^1$ represents a nitrogen atom, $R^{3b}$ represents a trifluoromethyl group, $R^{4c}$ represents a hydrogen atom, and T represents any substituents indicated in Table 1 to Table 6 (hereinafter, referred to as Compound Class $SX_{176}$).

A compound (L-8) wherein $G^1$ represents a nitrogen atom, $R^{3b}$ represents a trifluoromethyl group, $R^{4c}$ represents a methyl group, and T represents any substituents indicated in Table 1 to Table 6 (hereinafter, referred to as Compound Class $SX_{177}$).

A compound (L-8) wherein $G^1$ represents a nitrogen atom, $R^{3b}$ represents a trifluoromethyl group, $R^{4c}$ represents an ethyl group, and T represents any substituents indicated in Table 1 to Table 6 (hereinafter, referred to as Compound Class $SX_{178}$).

A compound (L-8) wherein $G^1$ represents a nitrogen atom, $R^{3b}$ represents a trifluoromethyl group, $R^{4c}$ represents a methoxy group, and T represents any substituents indicated in Table 1 to Table 6 (hereinafter, referred to as Compound Class $SX_{179}$).

A compound (L-8) wherein $G^1$ represents a nitrogen atom, $R^{3b}$ represents a trifluoromethyl group, $R^{4c}$ represents a chlorine atom, and T represents any substituents indicated in Table 1 to Table 6 (hereinafter, referred to as Compound Class $SX_{180}$).

A compound (L-8) wherein $G^1$ represents a nitrogen atom, $R^{3b}$ represents a trifluoromethyl group, $R^{4c}$ represents a bromine atom, and T represents any substituents indicated in Table 1 to Table 6 (hereinafter, referred to as Compound Class $SX_{181}$).

A compound (L-7) wherein $G^1$ represents a nitrogen atom, $R^{3b}$ represents a trifluoromethyl group, $R^{4c}$ represents a cyano group, and T represents any substituents indicated in Table 1 to Table 6 (hereinafter, referred to as Compound Class $SX_{182}$).

A compound represented by formula (L-9):

(hereinafter, referred to as compound (L-9)), wherein $A^1$ represents N—$CH_3$, $R^{4c}$ represents a hydrogen atom, and T represents any substituents indicated in Table 1 to Table 6 (hereinafter, referred to as Compound Class $SX_{183}$).

A compound (L-9) wherein $A^1$ represents N—$CH_3$, $R^{4c}$ represents a methyl group, and T represents any substituents indicated in Table 1 to Table 6 (hereinafter, referred to as Compound Class $SX_{184}$).

A compound (L-9) wherein $A^1$ represents N—$CH_3$, $R^{4c}$ represents an ethyl group, and T represents any substituents indicated in Table 1 to Table 6 (hereinafter, referred to as Compound Class $SX_{185}$).

A compound (L-9) wherein $A^1$ represents N—$CH_3$, $R^{4c}$ represents a methoxy group, and T represents any substituents indicated in Table 1 to Table 6 (hereinafter, referred to as Compound Class $SX_{186}$).

A compound (L-9) wherein $A^1$ represents N—$CH_3$, $R^{4c}$ represents a chlorine atom, and T represents any substituents indicated in Table 1 to Table 6 (hereinafter, referred to as Compound Class $SX_{187}$).

A compound (L-9) wherein $A^1$ represents N—$CH_3$, $R^{4c}$ represents a bromine atom, and T represents any substituents indicated in Table 1 to Table 6 (hereinafter, referred to as Compound Class $SX_{188}$).

A compound (L-9) wherein $A^1$ represents N—$CH_3$, $R^{4c}$ represents a cyano group, and T represents any substituents indicated in Table 1 to Table 6 (hereinafter, referred to as Compound Class $SX_{189}$).

A compound (L-9) wherein $A^1$ represents N—$CH_3$, $R^{4c}$ represents a hydrogen atom, and T represents any substituents indicated in Table 1 to Table 6 (hereinafter, referred to as Compound Class $SX_{190}$).

A compound (L-9) wherein $A^1$ represents N—$CH_3$, $R^{4c}$ represents a methyl group, and T represents any substituents indicated in Table 1 to Table 6 (hereinafter, referred to as Compound Class $SX_{191}$).

A compound (L-9) wherein $A^1$ represents N—$CH_3$, $R^{4c}$ represents an ethyl group, and T represents any substituents indicated in Table 1 to Table 6 (hereinafter, referred to as Compound Class $SX_{192}$).

A compound (L-9) wherein $A^1$ represents N—$CH_3$, $R^{4c}$ represents a methoxy group, and T represents any substituents indicated in Table 1 to Table 6 (hereinafter, referred to as Compound Class $SX_{193}$).

A compound (L-9) wherein $A^1$ represents N—$CH_3$, $R^{4c}$ represents a chlorine atom, and T represents any substituents indicated in Table 1 to Table 6 (hereinafter, referred to as Compound Class $SX_{194}$).

A compound (L-9) wherein $A^1$ represents N—$CH_3$, $R^{4c}$ represents a bromine atom, and T represents any substituents indicated in Table 1 to Table 6 (hereinafter, referred to as Compound Class $SX_{195}$).

A compound (L-9) wherein $A^1$ represents N—$CH_3$, $R^{4c}$ represents a cyano group, and T represents any substituents indicated in Table 1 to Table 6 (hereinafter, referred to as Compound Class $SX_{196}$).

A compound represented by formula (L-10):

(hereinafter, referred to as compound (L-10)), wherein $A^1$ represents N—$CH_3$, $R^{4c}$ represents a hydrogen atom, and T represents any substituents indicated in Table 1 to Table 6 (hereinafter, referred to as Compound Class $SX_{197}$).

A compound (L-10) wherein $A^1$ represents N—$CH_3$, $R^{4c}$ represents a methyl group, and T represents any substituents indicated in Table 1 to Table 6 (hereinafter, referred to as Compound Class $SX_{198}$).

A compound (L-10) wherein $A^1$ represents N—$CH_3$, $R^{4c}$ represents an ethyl group, and T represents any substituents indicated in Table 1 to Table 6 (hereinafter, referred to as Compound Class $SX_{199}$).

A compound (L-10) wherein $A^1$ represents N—$CH_3$, $R^{4c}$ represents a methoxy group, and T represents any substituents indicated in Table 1 to Table 6 (hereinafter, referred to as Compound Class $SX_{200}$).

A compound (L-10) wherein $A^1$ represents N—$CH_3$, $R^{4c}$ represents a chlorine atom, and T represents any substituents indicated in Table 1 to Table 6 (hereinafter, referred to as Compound Class $SX_{201}$).

A compound (L-10) wherein $A^1$ represents N—$CH_3$, $R^{4c}$ represents a bromine atom, and T represents any substituents indicated in Table 1 to Table 6 (hereinafter, referred to as Compound Class $SX_{202}$).

A compound (L-10) wherein $A^1$ represents N—$CH_3$, $R^{4c}$ represents a cyano group, and T represents any substituents indicated in Table 1 to Table 6 (hereinafter, referred to as Compound Class $SX_{203}$).

A compound (L-10) wherein $A^1$ represents N—$CH_3$, $R^{4c}$ represents a hydrogen atom, and T represents any substituents indicated in Table 1 to Table 6 (hereinafter, referred to as Compound Class $SX_{204}$).

A compound (L-10) wherein $A^1$ represents N—$CH_3$, $R^{4c}$ represents a methyl group, and T represents any substituents indicated in Table 1 to Table 6 (hereinafter, referred to as Compound Class $SX_{205}$).

A compound (L-10) wherein $A^1$ represents N—$CH_3$, $R^{4c}$ represents an ethyl group, and T represents any substituents indicated in Table 1 to Table 6 (hereinafter, referred to as Compound Class $SX_{206}$).

A compound (L-10) wherein $A^1$ represents N—$CH_3$, $R^{4c}$ represents a methoxy group, and T represents any substituents indicated in Table 1 to Table 6 (hereinafter, referred to as Compound Class $SX_{207}$).

A compound (L-10) wherein $A^1$ represents N—$CH_3$, $R^{4c}$ represents a chlorine atom, and T represents any substituents indicated in Table 1 to Table 6 (hereinafter, referred to as Compound Class $SX_{208}$).

A compound (L-10) wherein $A^1$ represents N—$CH_3$, $R^{4c}$ represents a bromine atom, and T represents any substituents indicated in Table 1 to Table 6 (hereinafter, referred to as Compound Class $SX_{209}$).

A compound (L-10) wherein $A^1$ represents N—$CH_3$, $R^{4c}$ represents a cyano group, and T represents any substituents indicated in Table 1 to Table 6 (hereinafter, referred to as Compound Class $SX_{210}$).

A compound represented by formula (L-11):

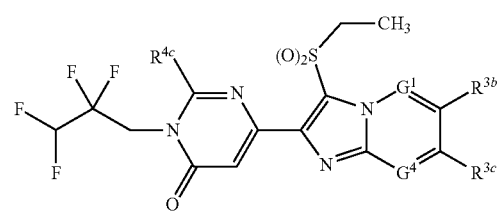

(L-11)

(hereinafter, referred to as compound (L-11)), wherein $G^1$ and $G^2$ represent CH, $R^{3b}$ and $R^{4c}$ represent a hydrogen atom, and $R^3$ represents any substituents indicated in Table 7 to Table 15 (hereinafter, referred to as Compound Class $SX_{211}$).

TABLE 7

| |
|---|
| F |
| Cl |
| Br |
| Me |
| Et |
| Pr |
| i-Pr |
| c-Pr |
| 1-CN-c-Pr |
| OMe |
| OEt |
| OPr |
| Oi-Pr |
| CN |
| C (O) OEt |
| CH = N-OH |
| CH = N-OMe |
| CH = N-OEt |
| CH = N-OCH$_2$CF$_3$ |
| CMe = N-OH |
| CMe = N-OMe |
| CMe = N-OEt |
| CMe = N-OCH$_2$CF$_3$ |
| C (NH$_2$) =N-OCH$_2$CF$_3$ |

TABLE 8

| |
|---|
| Ph |
| 3-F-Ph |
| 4-F-Ph |
| 3-Cl-Ph |
| 3-Cl-Ph |
| 4-Cl-Ph |
| 3-CF$_3$-Ph |
| 4-CF$_3$-Ph |
| 3-NMe$_2$-Ph |
| 4-NMe$_2$-Ph |
| 3-CN-Ph |
| 4-CN-Ph |
| 4-C (O) NMe$_2$-Ph |
| 4-NHC (O) Me-Ph |
| 3, 4-F$_2$-Ph |
| 3, 5-F$_2$-Ph |
| 2, 4-F$_2$--Ph |
| 3, 4, 5-F$_3$-Ph |
| 3, 4-Cl$_2$-Ph |
| 3, 5-Cl$_2$-Ph |
| 3, 5-Cl$_2$-4-F-Ph |
| OPh |
| O-2-F-Ph |
| NH$_2$ |
| NHCH$_2$CF$_3$ |

TABLE 9
Py2
4-F-Py2
5-F-Py2
4-Cl-Py2
5-Cl-Py2
4-CF$_3$-Py2
5-CF$_3$-Py2
3-Me-Py2
4-Me-Py2
5-Me-Py2
6-Me-Py2
5-CN-Py2
5-OCH$_2$CF$_2$CF$_3$-Py2
3, 5-F$_2$-Py2
Py3
6-CF$_3$-Py3
5-CF$_3$-Py3
6-F-Py3
6-Cl-Py3
Py4
OPy2
OPy3
NHC (O) c-Pr
NMeC (O) c-Pr
TABLE 10
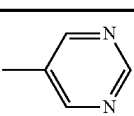
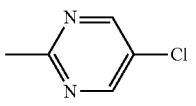
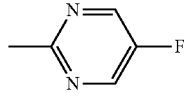
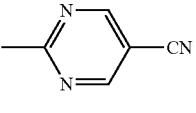
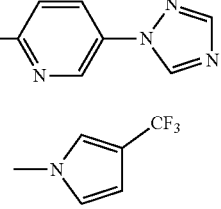
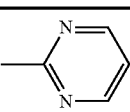
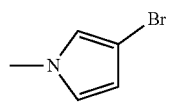
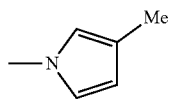
TABLE 11
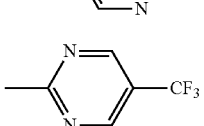
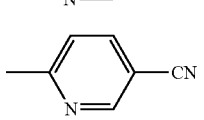
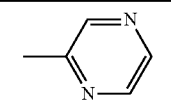
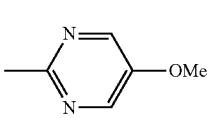
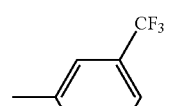
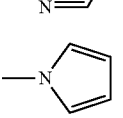
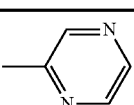
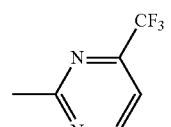
TABLE 12
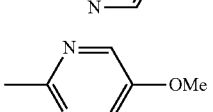
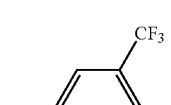
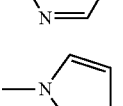

TABLE 12-continued
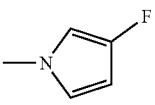
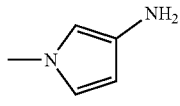
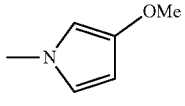
TABLE 13
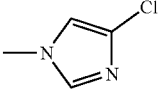
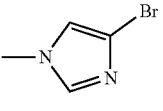
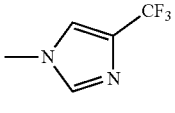
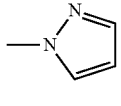
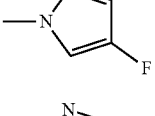
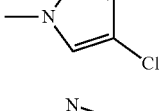
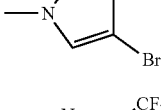
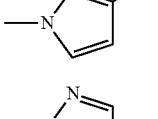
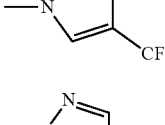
TABLE 14
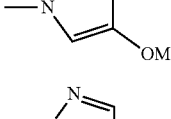
TABLE 14-continued
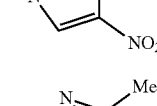
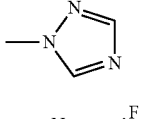
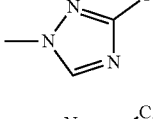
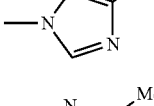
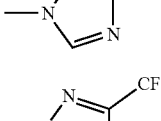
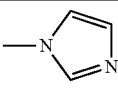
TABLE 15

TABLE 15-continued

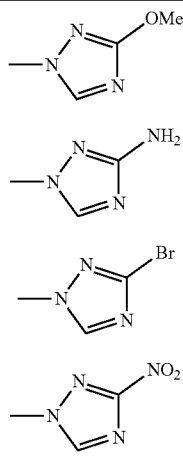

A compound represented by formula (L-11) wherein $G^1$ and $G^2$ represent CH, $R^{3b}$ represents a hydrogen atom, $R^{4c}$ represents a methyl group, $R^{3c}$ represents any substituents indicated in Table 7 to Table 15 (hereinafter, referred to as Compound Class $SX_{212}$).

A compound represented by formula (L-11) wherein $G^1$ and $G^2$ represent CH, $R^{3b}$ represents a hydrogen atom, $R^{4c}$ represents an ethyl group, $R^{3c}$ represents any substituents indicated in Table 7 to Table 15 (hereinafter, referred to as Compound Class $SX_{213}$).

A compound represented by formula (L-11) wherein $G^1$ and $G^2$ represent CH, $R^{3b}$ represents a hydrogen atom, $R^{4c}$ represents a methoxy group, $R^3$ represents any substituents indicated in Table 7 to Table 15 (hereinafter, referred to as Compound Class $SX_{214}$).

A compound represented by formula (L-11) wherein $G^1$ and $G^2$ represent CH, $R^{3b}$ represents a hydrogen atom, $R^{4c}$ represents a chlorine atom, $R^{3c}$ represents any substituents indicated in Table 7 to Table 15 (hereinafter, referred to as Compound Class $SX_{215}$).

A compound represented by formula (L-11) wherein $G^1$ and $G^2$ represent CH, $R^{3b}$ represents a hydrogen atom, $R^{4c}$ represents a bromine atom, $R^{3c}$ represents any substituents indicated in Table 7 to Table 15 (hereinafter, referred to as Compound Class $SX_{216}$).

A compound represented by formula (L-11) wherein $G^1$ and $G^2$ represent CH, $R^{3b}$ represents a hydrogen atom, $R^{4c}$ represents a cyano group, $R^{3c}$ represents any substituents indicated in Table 7 to Table 15 (hereinafter, referred to as Compound Class $SX_{217}$).

A compound represented by formula (L-11) wherein $G^1$ and $G^2$ represent CH, $R^{3b}$ represents a hydrogen atom, $R^{4c}$ represents a hydrogen atom, $R^{3c}$ represents any substituents indicated in Table 7 to Table 15 (hereinafter, referred to as Compound Class $SX_{218}$).

A compound represented by formula (L-11) wherein $G^1$ and $G^2$ represent CH, $R^{3b}$ represents a hydrogen atom, $R^{4c}$ represents a methyl group, $R^{3c}$ represents any substituents indicated in Table 7 to Table 15 (hereinafter, referred to as Compound Class $SX_{219}$).

A compound represented by formula (L-11) wherein $G^1$ and $G^2$ represent CH, $R^{3b}$ represents a hydrogen atom, $R^{4c}$ represents an ethyl group, $R^{3c}$ represents any substituents indicated in Table 7 to Table 15 (hereinafter, referred to as Compound Class $SX_{220}$).

A compound represented by formula (L-11) wherein $G^1$ and $G^2$ represent CH, $R^{3b}$ represents a hydrogen atom, $R^{4c}$ represents a methoxy group, $R^{3c}$ represents any substituents indicated in Table 7 to Table 15 (hereinafter, referred to as Compound Class $SX_{221}$).

A compound represented by formula (L-11) wherein $G^1$ and $G^2$ represent CH, $R^{3b}$ represents a hydrogen atom, $R^{4c}$ represents a chlorine atom, $R^{3c}$ represents any substituents indicated in Table 7 to Table 15 (hereinafter, referred to as Compound Class $SX_{222}$).

A compound represented by formula (L-11) wherein $G^1$ and $G^2$ represent CH, $R^{3b}$ represents a hydrogen atom, $R^{4c}$ represents a bromine atom, $R^{3c}$ represents any substituents indicated in Table 7 to Table 15 (hereinafter, referred to as Compound Class $SX_{223}$).

A compound represented by formula (L-11) wherein $G^1$ and $G^2$ represent CH, $R^{3b}$ represents a hydrogen atom, $R^{4c}$ represents a cyano group, $R^{3c}$ represents any substituents indicated in Table 7 to Table 15 (hereinafter, referred to as Compound Class $SX_{224}$).

A compound represented by formula (L-11) wherein $G^1$ represents CH, $G^4$ represents a nitrogen atom, $R^{3b}$ represents a hydrogen atom, $R^{4c}$ represents a hydrogen atom, $R^{3c}$ represents any substituents indicated in Table 7 to Table 15 (hereinafter, referred to as Compound Class $SX_{225}$).

A compound represented by formula (L-11) wherein $G^1$ represents CH, $G^4$ represents a nitrogen atom, $R^{3b}$ represents a hydrogen atom, $R^{4c}$ represents a methyl group, $R^{3c}$ represents any substituents indicated in Table 7 to Table 15 (hereinafter, referred to as Compound Class $SX_{226}$).

A compound represented by formula (L-11) wherein $G^1$ represents CH, $G^4$ represents a nitrogen atom, $R^{3b}$ represents a hydrogen atom, $R^{4c}$ represents an ethyl group, $R^{3c}$ represents any substituents indicated in Table 7 to Table 15 (hereinafter, referred to as Compound Class $SX_{227}$).

A compound represented by formula (L-11) wherein $G^1$ represents CH, $G^4$ represents a nitrogen atom, $R^3$ represents a hydrogen atom, $R^{4c}$ represents a methoxy group, $R^{3c}$ represents any substituents indicated in Table 7 to Table 15 (hereinafter, referred to as Compound Class $SX_{228}$).

A compound represented by formula (L-11) wherein $G^1$ represents CH, $G^4$ represents a nitrogen atom, $R^{3b}$ represents a hydrogen atom, $R^{4c}$ represents a chlorine atom, $R^{3c}$ represents any substituents indicated in Table 7 to Table 15 (hereinafter, referred to as Compound Class $SX_{229}$).

A compound represented by formula (L-11) wherein $G^1$ represents CH, $G^4$ represents a nitrogen atom, $R^{3b}$ represents a hydrogen atom, $R^{4c}$ represents a bromine atom, $R^{3c}$ represents any substituents indicated in Table 7 to Table 15 (hereinafter, referred to as Compound Class $SX_{230}$).

A compound represented by formula (L-11) wherein $G^1$ represents CH, $G^4$ represents a nitrogen atom, $R^{3b}$ represents a hydrogen atom, $R^{4c}$ represents a cyano group, $R^{3c}$ represents any substituents indicated in Table 7 to Table 15 (hereinafter, referred to as Compound Class $SX_{231}$).

A compound represented by formula (L-11) wherein $G^1$ represents CH, $G^4$ represents a nitrogen atom, $R^{3b}$ represents a hydrogen atom, $R^{4c}$ represents a hydrogen atom, $R^{3c}$ represents any substituents indicated in Table 7 to Table 15 (hereinafter, referred to as Compound Class $SX_{232}$).

A compound represented by formula (L-11) wherein $G^1$ represents CH, $G^4$ represents a nitrogen atom, $R^{3b}$ represents a hydrogen atom, $R^{4c}$ represents a methyl group, $R^{3c}$ represents any substituents indicated in Table 7 to Table 15 (hereinafter, referred to as Compound Class $SX_{233}$).

A compound represented by formula (L-11) wherein $G^1$ represents CH, $G^4$ represents a nitrogen atom, $R^{3b}$ represents a hydrogen atom, $R^{4c}$ represents an ethyl group, $R^{3c}$ represents any substituents indicated in Table 7 to Table 15 (hereinafter, referred to as Compound Class $SX_{234}$).

A compound represented by formula (L-11) wherein $G^1$ represents CH, $G^4$ represents a nitrogen atom, $R^{3b}$ represents a hydrogen atom, $R^{4c}$ represents a methoxy group, $R^3$ represents any substituents indicated in Table 7 to Table 15 (hereinafter, referred to as Compound Class $SX_{235}$).

A compound represented by formula (L-11) wherein $G^1$ represents CH, $G^4$ represents a nitrogen atom, $R^{3b}$ represents a hydrogen atom, $R^{4c}$ represents a chlorine atom, $R^{3c}$ represents any substituents indicated in Table 7 to Table 15 (hereinafter, referred to as Compound Class $SX_{236}$).

A compound represented by formula (L-11) wherein $G^1$ represents CH, $G^4$ represents a nitrogen atom, $R^{3b}$ represents a hydrogen atom, $R^{4c}$ represents a bromine atom, $R^{3c}$ represents any substituents indicated in Table 7 to Table 15 (hereinafter, referred to as Compound Class $SX_{237}$).

A compound represented by formula (L-11) wherein $G^1$ represents CH, $G^4$ represents a nitrogen atom, $R^3$ represents a hydrogen atom, $R^{4c}$ represents a cyano group, $R^{3c}$ represents any substituents indicated in Table 7 to Table 15 (hereinafter, referred to as Compound Class $SX_{238}$).

A compound represented by formula (L-11) wherein $G^1$ represents a nitrogen atom, $G^4$ represents CH, $R^{3b}$ represents a hydrogen atom, $R^{4c}$ represents a hydrogen atom, $R^{3c}$ represents any substituents indicated in Table 7 to Table 15 (hereinafter, referred to as Compound Class $SX_{239}$).

A compound represented by formula (L-11) wherein $G^1$ represents CH, $G^4$ represents a nitrogen atom, $R^{3b}$ represents a hydrogen atom, $R^{4c}$ represents a methyl group, $R^{3c}$ represents any substituents indicated in Table 7 to Table 15 (hereinafter, referred to as Compound Class $SX_{240}$).

A compound represented by formula (L-11) wherein $G^1$ represents a nitrogen atom, $G^4$ represents CH, $R^{3b}$ represents a hydrogen atom, $R^{4c}$ represents an ethyl group, $R^{3c}$ represents any substituents indicated in Table 7 to Table 15 (hereinafter, referred to as Compound Class $SX_{241}$).

A compound represented by formula (L-11) wherein $G^1$ represents a nitrogen atom, $G^4$ represents CH, $R^{3b}$ represents a hydrogen atom, $R^{4c}$ represents a methoxy group, $R^{3c}$ represents any substituents indicated in Table 7 to Table 15 (hereinafter, referred to as Compound Class $SX_{242}$).

A compound represented by formula (L-11) wherein $G^1$ represents a nitrogen atom, $G^4$ represents CH, $R^{3b}$ represents a hydrogen atom, $R^{4c}$ represents a chlorine atom, $R^{3c}$ represents any substituents indicated in Table 7 to Table 15 (hereinafter, referred to as Compound Class $SX_{243}$).

A compound represented by formula (L-11) wherein $G^1$ represents a nitrogen atom, $G^4$ represents CH, $R^{3b}$ represents a hydrogen atom, $R^{4c}$ represents a bromine atom, $R^{3c}$ represents any substituents indicated in Table 7 to Table 15 (hereinafter, referred to as Compound Class $SX_{244}$).

A compound represented by formula (L-11) wherein $G^1$ represents CH, $G^4$ represents a nitrogen atom, $R^{3b}$ represents a hydrogen atom, $R^{4c}$ represents a cyano group, $R^{3c}$ represents any substituents indicated in Table 7 to Table 15 (hereinafter, referred to as Compound Class $SX_{245}$).

A compound represented by formula (L-11) wherein G represents a nitrogen atom, $G^4$ represents CH, $R^{3b}$ represents a hydrogen atom, $R^{4c}$ represents a hydrogen atom, $R^{3c}$ represents any substituents indicated in Table 7 to Table 15 (hereinafter, referred to as Compound Class $SX_{246}$).

A compound represented by formula (L-11) wherein $G^1$ represents a nitrogen atom, $G^4$ represents CH, $R^{3b}$ represents a hydrogen atom, $R^{4c}$ represents a methyl group, $R^{3c}$ represents any substituents indicated in Table 7 to Table 15 (hereinafter, referred to as Compound Class $SX_{247}$).

A compound represented by formula (L-11) wherein $G^1$ represents a nitrogen atom, $G^4$ represents CH, $R^{3b}$ represents a hydrogen atom, $R^{4c}$ represents an ethyl group, $R^{3c}$ represents any substituents indicated in Table 7 to Table 15 (hereinafter, referred to as Compound Class $SX_{248}$).

A compound represented by formula (L-11) wherein $G^1$ represents a nitrogen atom, $G^4$ represents CH, $R^{3b}$ represents a hydrogen atom, $R^{4c}$ represents a methoxy group, $R^{3c}$ represents any substituents indicated in Table 7 to Table 15 (hereinafter, referred to as Compound Class $SX_{249}$).

A compound represented by formula (L-11) wherein $G^1$ represents CH, $G^4$ represents a nitrogen atom, $R^{3b}$ represents a hydrogen atom, $R^{4c}$ represents a chlorine atom, $R^3$ represents any substituents indicated in Table 7 to Table 15 (hereinafter, referred to as Compound Class $SX_{250}$).

A compound represented by formula (L-11) wherein $G^1$ represents a nitrogen atom, $G^4$ represents CH, $R^{3b}$ represents a hydrogen atom, $R^{4c}$ represents a bromine atom, $R^{3c}$ represents any substituents indicated in Table 7 to Table 15 (hereinafter, referred to as Compound Class $SX_{251}$).

A compound represented by formula (L-11) wherein $G^1$ represents a nitrogen atom, $G^4$ represents CH, $R^{3b}$ represents a hydrogen atom, $R^{4c}$ represents a cyano group, $R^{3c}$ represents any substituents indicated in Table 7 to Table 15 (hereinafter, referred to as Compound Class $SX_{252}$).

A compound represented by formula (L-12):

(L-12)

(hereinafter, referred to as compound (L-12)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{253}$).

A compound represented by formula (L-12) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{254}$).

A compound represented by formula (L-12) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{255}$).

A compound represented by formula (L-12) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{256}$).

A compound represented by formula (L-12) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{257}$).

A compound represented by formula (L-12) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{258}$).

A compound represented by formula (L-12) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{259}$).

A compound represented by formula (L-12) wherein $G^1$ and $G^4$ represent CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{260}$).

A compound represented by formula (L-12) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{261}$).

A compound represented by formula (L-12) wherein $G^1$ and $G^4$ represent CH, $R^3$ represents a hydrogen atom, $R^{4c}$ represents an ethyl group, and $R^{3b}$ represents any substituents indicated in Table 7 to Table 15 (hereinafter, referred to as Compound Class $SX_{262}$).

A compound represented by formula (L-12) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{263}$).

A compound represented by formula (L-12) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{264}$).

A compound represented by formula (L-12) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{265}$).

A compound represented by formula (L-12) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{266}$).

A compound represented by formula (L-12) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{267}$).

A compound represented by formula (L-12) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{268}$).

A compound represented by formula (L-12) wherein $G^1$ represents CH, $G^4$ represents a nitrogen atom, $R^{3b}$ represents a hydrogen atom, $R^{4c}$ represents an ethyl group, and $R^k$ represents any substituents indicated in Table 7 to Table 15 (hereinafter, referred to as Compound Class $SX_{269}$).

A compound represented by formula (L-12) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{270}$).

A compound represented by formula (L-12) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{271}$).

A compound represented by formula (L-12) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{272}$).

A compound represented by formula (L-12) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{273}$).

A compound represented by formula (L-12) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{274}$).

A compound represented by formula (L-12) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{275}$).

A compound represented by formula (L-12) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{276}$).

A compound represented by formula (L-12) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{277}$).

A compound represented by formula (L-12) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{278}$).

A compound represented by formula (L-12) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{279}$).

A compound represented by formula (L-12) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{280}$).

A compound represented by formula (L-12) wherein $G^1$ represents a nitrogen atom, $G^4$ represents CH, $R^{3b}$ represents a hydrogen atom, $R^{4c}$ represents a hydrogen atom, and $R^3$ represents any substituents indicated in Table 7 to Table 15 (hereinafter, referred to as Compound Class $SX_{281}$).

A compound represented by formula (L-12) wherein $G^1$ represents a nitrogen atom, $G^4$ represents CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{282}$).

A compound represented by formula (L-12) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{283}$).

A compound represented by formula (L-12) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{284}$).

A compound represented by formula (L-12) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{285}$).

A compound represented by formula (L-12) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{286}$).

A compound represented by formula (L-12) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{287}$).

A compound represented by formula (L-12) wherein $G^1$ represents a nitrogen atom, $G^4$ represents CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{288}$).

A compound represented by formula (L-12) wherein $G^1$ represents a nitrogen atom, $G^4$ represents CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{289}$).

A compound represented by formula (L-12) wherein $G^1$ represents a nitrogen atom, $G^4$ represents CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{290}$).

A compound represented by formula (L-12) wherein $G^1$ represents a nitrogen atom, $G^4$ represents CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{291}$).

A compound represented by formula (L-12) wherein $G^1$ represents a nitrogen atom, $G^4$ represents CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{292}$).

A compound represented by formula (L-12) wherein $G^1$ represents a nitrogen atom, $G^4$ represents CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{293}$).

A compound represented by formula (L-12) wherein $G^1$ represents a nitrogen atom, $G^4$ represents CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{294}$).

A compound represented by formula (L-13):

(L-13)

(hereinafter, referred to as compound (L-13)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{295}$).

A compound represented by formula (L-13) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{296}$).

A compound represented by formula (L-13) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{297}$).

A compound represented by formula (L-13) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{298}$).

A compound represented by formula (L-13) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{299}$).

A compound represented by formula (L-13) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{300}$).

A compound represented by formula (L-13) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{301}$).

A compound represented by formula (L-13) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{302}$).

A compound represented by formula (L-13) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{303}$).

A compound represented by formula (L-13) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{304}$).

A compound represented by formula (L-13) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{305}$).

A compound represented by formula (L-13) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{306}$).

A compound represented by formula (L-13) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{307}$).

A compound represented by formula (L-13) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{308}$).

A compound represented by formula (L-13) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{309}$).

A compound represented by formula (L-13) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{310}$).

A compound represented by formula (L-13) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{311}$).

A compound represented by formula (L-13) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{312}$).

A compound represented by formula (L-13) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{313}$).

A compound represented by formula (L-13) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{314}$).

A compound represented by formula (L-13) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{315}$).

A compound represented by formula (L-13) wherein $G^1$ represents CH, $G^4$ represents a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{316}$).

A compound represented by formula (L-13) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{317}$).

A compound represented by formula (L-13) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{318}$).

A compound represented by formula (L-13) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{319}$).

A compound represented by formula (L-13) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{320}$).

A compound represented by formula (L-13) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{321}$).

A compound represented by formula (L-13) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{322}$).

A compound represented by formula (L-13) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{323}$).

A compound represented by formula (L-13) wherein $G^1$ represents a nitrogen atom, $G^4$ represents CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{324}$).

A compound represented by formula (L-13) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{325}$).

A compound represented by formula (L-13) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{326}$).

A compound represented by formula (L-13) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{327}$).

A compound represented by formula (L-13) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{328}$).

A compound represented by formula (L-13) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{329}$).

A compound represented by formula (L-13) wherein $G^1$ represents a nitrogen atom, $G^4$ represents CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{330}$).

A compound represented by formula (L-13) wherein $G^1$ represents a nitrogen atom, $G^4$ represents CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{331}$).

A compound represented by formula (L-13) wherein $G^1$ represents a nitrogen atom, $G^4$ represents CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{332}$).

A compound represented by formula (L-13) wherein $G^1$ represents a nitrogen atom, $G^4$ represents CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{333}$).

A compound represented by formula (L-13) wherein $G^1$ represents a nitrogen atom, $G^4$ represents CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{334}$).

A compound represented by formula (L-13) wherein $G^1$ represents a nitrogen atom, $G^4$ represents CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{335}$).

A compound represented by formula (L-13) wherein $G^1$ represents a nitrogen atom, $G^4$ represents CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{336}$).

A compound represented by formula (L-14):

(L-14)

(hereinafter, referred to as compound (L-14)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{337}$).

A compound represented by formula (L-14) wherein $G^1$ and $G^1$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{338}$).

A compound represented by formula (L-14) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{339}$).

A compound represented by formula (L-14) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{340}$).

A compound represented by formula (L-14) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{341}$).

A compound represented by formula (L-14) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{342}$).

A compound represented by formula (L-14) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{343}$).

A compound represented by formula (L-14) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{344}$).

A compound represented by formula (L-14) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{345}$).

A compound represented by formula (L-14) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{346}$).

A compound represented by formula (L-14) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{347}$).

A compound represented by formula (L-14) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{348}$).

A compound represented by formula (L-14) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{349}$).

A compound represented by formula (L-14) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{350}$).

A compound represented by formula (L-14) wherein $G^1$ represents Cl, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{351}$).

A compound represented by formula (L-14) wherein $G^1$ a hydrogen atom, $R^{4c}$ represents a methyl group, and $R^{3c}$ represents any substituents indicated in Table 7 to Table 15 (hereinafter, referred to as Compound Class $SX_{352}$).

A compound represented by formula (L-14) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{353}$).

A compound represented by formula (L-14) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{354}$).

A compound represented by formula (L-14) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{355}$).

A compound represented by formula (L-14) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{356}$).

A compound represented by formula (L-14) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{357}$).

A compound represented by formula (L-14) wherein $G^1$ represents CH, $G^4$ represents a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{358}$).

A compound represented by formula (L-14) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{359}$).

A compound represented by formula (L-14) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{360}$).

A compound represented by formula (L-14) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{361}$).

A compound represented by formula (L-14) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{362}$).

A compound represented by formula (L-14) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{363}$).

A compound represented by formula (L-14) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{364}$).

A compound represented by formula (L-14) wherein $G^1$ represents a nitrogen atom, $G^4$ represents CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{365}$).

A compound represented by formula (L-14) wherein $G^1$ represents a nitrogen atom, $G^4$ represents CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{366}$).

A compound represented by formula (L-14) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{367}$).

A compound represented by formula (L-14) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{368}$).

A compound represented by formula (L-14) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{369}$).

A compound represented by formula (L-14) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{370}$).

A compound represented by formula (L-14) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{371}$).

A compound represented by formula (L-14) wherein $G^1$ represents a nitrogen atom, $G^4$ represents CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{372}$).

A compound represented by formula (L-14) wherein $G^1$ represents a nitrogen atom, $G^4$ represents CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{373}$).

A compound represented by formula (L-14) wherein $G^1$ represents a nitrogen atom, $G^4$ represents CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{374}$).

A compound represented by formula (L-14) wherein $G^1$ represents a nitrogen atom, $G^4$ represents CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{375}$).

A compound represented by formula (L-14) wherein $G^1$ represents a nitrogen atom, $G^4$ represents CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{376}$).

A compound represented by formula (L-14) wherein $G^1$ represents a nitrogen atom, $G^4$ represents CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{377}$).

A compound represented by formula (L-14) wherein $G^1$ represents a nitrogen atom, $G^4$ represents CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{371}$).

A compound represented by formula (L-15):

(hereinafter, referred to as compound (L-15)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{379}$).

A compound represented by formula (L-15) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{380}$).

A compound represented by formula (L-15) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{381}$).

A compound represented by formula (L-15) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{382}$).

A compound represented by formula (L-15) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{383}$).

A compound represented by formula (L-15) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{384}$).

A compound represented by formula (L-15) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{385}$).

A compound represented by formula (L-15) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{386}$).

A compound represented by formula (L-15) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{387}$).

A compound represented by formula (L-15) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{388}$).

A compound represented by formula (L-15) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{389}$).

A compound represented by formula (L-15) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{390}$).

A compound represented by formula (L-15) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{391}$).

A compound represented by formula (L-15) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{392}$).

A compound represented by formula (L-15) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{393}$).

A compound represented by formula (L-15) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{394}$).

A compound represented by formula (L-15) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{395}$).

A compound represented by formula (L-15) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{396}$).

A compound represented by formula (L-15) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{397}$).

A compound represented by formula (L-15) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{398}$).

A compound represented by formula (L-15) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{399}$).

A compound represented by formula (L-15) wherein $G^1$ represents CH, $G^4$ represents a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{400}$).

A compound represented by formula (L-15) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{401}$).

A compound represented by formula (L-15) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{402}$).

A compound represented by formula (L-15) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{403}$).

A compound represented by formula (L-15) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{404}$).

A compound represented by formula (L-15) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{405}$).

A compound represented by formula (L-15) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{406}$).

A compound represented by formula (L-15) wherein $G^1$ represents a nitrogen atom, $G^4$ represents CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{407}$).

A compound represented by formula (L-15) wherein $G^1$ represents a nitrogen atom, $G^4$ represents CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{408}$).

A compound represented by formula (L-15) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{409}$).

A compound represented by formula (L-15) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{410}$).

A compound represented by formula (L-15) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{411}$).

A compound represented by formula (L-15) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{412}$).

A compound represented by formula (L-15) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{413}$).

A compound represented by formula (L-15) wherein $G^1$ represents a nitrogen atom, $G^4$ represents CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{414}$).

A compound represented by formula (L-15) wherein $G^1$ represents a nitrogen atom, $G^4$ represents CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{415}$).

A compound represented by formula (L-15) wherein $G^1$ represents a nitrogen atom, $G^4$ represents CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{416}$).

A compound represented by formula (L-15) wherein $G^1$ represents a nitrogen atom, $G^4$ represents CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{417}$).

A compound represented by formula (L-15) wherein $G^1$ represents a nitrogen atom, $G^4$ represents CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{481}$).

A compound represented by formula (L-15) wherein $G^1$ represents a nitrogen atom, $G^4$ represents CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{419}$).

A compound represented by formula (L-15) wherein $G^1$ represents a nitrogen atom, $G^4$ represents CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{420}$).

A compound represented by formula (L-16):

$$(L\text{-}16)$$

(hereinafter, referred to as compound (L-16)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{421}$).

A compound represented by formula (L-16) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{422}$).

A compound represented by formula (L-16) wherein $G^1$ and $G^1$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{423}$).

A compound represented by formula (L-16) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{424}$).

A compound represented by formula (L-16) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{425}$).

A compound represented by formula (L-16) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{426}$).

A compound represented by formula (L-16) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{427}$).

A compound represented by formula (L-16) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{428}$).

A compound represented by formula (L-16) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{429}$).

A compound represented by formula (L-16) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{430}$).

A compound represented by formula (L-16) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{431}$).

A compound represented by formula (L-16) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{432}$).

A compound represented by formula (L-16) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{433}$).

A compound represented by formula (L-16) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{434}$).

A compound represented by formula (L-16) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{435}$).

A compound represented by formula (L-16) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{436}$).

A compound represented by formula (L-16) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{437}$).

A compound represented by formula (L-16) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{438}$).

A compound represented by formula (L-16) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{439}$).

A compound represented by formula (L-16) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{440}$).

A compound represented by formula (L-16) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{441}$).

A compound represented by formula (L-16) wherein $G^1$ represents CH, $G^4$ represents a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{442}$).

A compound represented by formula (L-16) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{443}$).

A compound represented by formula (L-16) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{444}$).

A compound represented by formula (L-16) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{445}$).

A compound represented by formula (L-16) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{446}$).

A compound represented by formula (L-16) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{447}$).

A compound represented by formula (L-16) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{448}$).

A compound represented by formula (L-16) wherein $G^1$ represents a nitrogen atom, $G^4$ represents CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{449}$).

A compound represented by formula (L-16) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{450}$).

A compound represented by formula (L-16) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{451}$).

A compound represented by formula (L-16) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{452}$).

A compound represented by formula (L-16) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{453}$).

A compound represented by formula (L-16) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{454}$).

A compound represented by formula (L-16) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{455}$).

A compound represented by formula (L-16) wherein $G^1$ represents a nitrogen atom, $G^4$ represents CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{456}$).

A compound represented by formula (L-16) wherein $G^1$ represents a nitrogen atom, $G^4$ represents CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{457}$).

A compound represented by formula (L-16) wherein $G^1$ represents a nitrogen atom, $G^4$ represents CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{458}$).

A compound represented by formula (L-16) wherein $G^1$ represents a nitrogen atom, $G^4$ represents CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{459}$).

A compound represented by formula (L-16) wherein $G^1$ represents a nitrogen atom, $G^4$ represents CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{460}$).

A compound represented by formula (L-16) wherein $G^1$ represents a nitrogen atom, $G^4$ represents CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{461}$).

A compound represented by formula (L-16) wherein $G^1$ represents a nitrogen atom, $G^4$ represents CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{462}$).

A compound represented by formula (L-17):

(L-17)

[Chemical structure]

(hereinafter, referred to as compound (L-17)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{463}$).

A compound represented by formula (L-17) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{464}$).

A compound represented by formula (L-17) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{465}$).

A compound represented by formula (L-17) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{466}$).

A compound represented by formula (L-17) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{467}$).

A compound represented by formula (L-17) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{468}$).

A compound represented by formula (L-17) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{469}$).

A compound represented by formula (L-17) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{470}$).

A compound represented by formula (L-17) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{471}$).

A compound represented by formula (L-17) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{472}$).

A compound represented by formula (L-17) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{473}$).

A compound represented by formula (L-17) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{474}$).

A compound represented by formula (L-17) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{475}$).

A compound represented by formula (L-17) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{476}$).

A compound represented by formula (L-17) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{477}$).

A compound represented by formula (L-17) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{478}$).

A compound represented by formula (L-17) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{479}$).

A compound represented by formula (L-17) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{480}$).

A compound represented by formula (L-17) wherein $G^1$ represents CH, $G^4$ represents a nitrogen atom, $R^{3b}$ represents a hydrogen atom, $R^{4c}$ represents a chlorine atom, and $R^{3e}$ represents any substituents indicated in Table 7 to Table 15 (hereinafter, referred to as Compound Class $SX_{481}$).

A compound represented by formula (L-17) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{482}$).

A compound represented by formula (L-17) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{483}$).

A compound represented by formula (L-17) wherein $G^1$ represents CH, $G^4$ represents a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{484}$).

A compound represented by formula (L-17) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{485}$).

A compound represented by formula (L-17) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{486}$).

A compound represented by formula (L-17) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{487}$).

A compound represented by formula (L-17) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{488}$).

A compound represented by formula (L-17) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{489}$).

A compound represented by formula (L-17) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{490}$).

A compound represented by formula (L-17) wherein $G^1$ represents a nitrogen atom, $G^4$ represents CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{491}$).

A compound represented by formula (L-17) wherein $G^1$ represents a nitrogen atom, $G^4$ represents CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{492}$).

A compound represented by formula (L-17) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{493}$).

A compound represented by formula (L-17) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{494}$).

A compound represented by formula (L-17) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{495}$).

A compound represented by formula (L-17) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{496}$).

A compound represented by formula (L-17) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{497}$).

A compound represented by formula (L-17) wherein $G^1$ represents a nitrogen atom, $G^4$ represents CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{498}$).

A compound represented by formula (L-17) wherein $G^1$ represents CH, $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{499}$).

A compound represented by formula (L-17) wherein $G^1$ represents a nitrogen atom, $G^4$ represents CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{500}$).

A compound represented by formula (L-17) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{501}$).

A compound represented by formula (L-17) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{502}$).

A compound represented by formula (L-17) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{503}$).

A compound represented by formula (L-17) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{504}$).

A compound represented by formula (L-18):

(L-18)

(hereinafter, referred to as compound (L-18)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{505}$).

A compound represented by formula (L-18) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{506}$).

A compound represented by formula (L-18) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{507}$).

A compound represented by formula (L-18) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{508}$).

A compound represented by formula (L-18) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{509}$).

A compound represented by formula (L-18) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{510}$).

A compound represented by formula (L-18) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{511}$).

A compound represented by formula (L-18) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{512}$).

A compound represented by formula (L-18) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{513}$).

A compound represented by formula (L-18) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{514}$).

A compound represented by formula (L-18) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{515}$).

A compound represented by formula (L-18) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{516}$).

A compound represented by formula (L-18) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{517}$).

A compound represented by formula (L-18) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{518}$).

A compound represented by formula (L-18) wherein $G^1$ represents CH, and $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{519}$).

A compound represented by formula (L-18) wherein $G^1$ represents CH, and $G^4$ represents a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{520}$).

A compound represented by formula (L-18) wherein $G^1$ represents CH, and $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{521}$).

A compound represented by formula (L-18) wherein $G^1$ represents CH, and $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{522}$).

A compound represented by formula (L-18) wherein $G^1$ represents CH, and $G^4$ represents a nitrogen atom, $R^{3b}$ represents a hydrogen atom, $R^{4c}$ represents a chlorine atom and $R^{3c}$ represents any substituents indicated in Table 7 to Table 15 (hereinafter, referred to as Compound Class $SX_{523}$).

A compound represented by formula (L-18) wherein $G^1$ represents CH, and $G^4$ represents a nitrogen atom, $R^{3b}$ represents a hydrogen atom, $R^{4c}$ represents a bromine atom and $R^{3c}$ represents any substituents indicated in Table 7 to Table 15 (hereinafter, referred to as Compound Class $SX_{524}$).

A compound represented by formula (L-18) wherein $G^1$ represents CH, and $G^4$ represents a nitrogen atom, $R^{3b}$ represents a hydrogen atom, $R^{4c}$ represents a cyano group and $R^{3c}$ represents any substituents indicated in Table 7 to Table 15 (hereinafter, referred to as Compound Class $SX_{525}$).

A compound represented by formula (L-18) wherein $G^1$ represents CH, and $G^4$ represents a nitrogen atom, $R^{3c}$ represents a hydrogen atom, $R^{4c}$ represents a hydrogen atom and $R^{3b}$ represents any substituents indicated in Table 7 to Table 15 (hereinafter, referred to as Compound Class $SX_{526}$).

A compound represented by formula (L-18) wherein $G^1$ represents CH, and $G^4$ represents a nitrogen atom, $R^{3c}$ represents a hydrogen atom, $R^{4c}$ represents a methyl group and $R^{3b}$ represents any substituents indicated in Table 7 to Table 15 (hereinafter, referred to as Compound Class $SX_{527}$).

A compound represented by formula (L-18) wherein $G^1$ represents CH, and $G^4$ represents a nitrogen atom, $R^{3c}$ represents a hydrogen atom, $R^{4c}$ represents an ethyl group and $R^{3b}$ represents any substituents indicated in Table 7 to Table 15 (hereinafter, referred to as Compound Class $SX_{528}$).

A compound represented by formula (L-18) wherein $G^1$ represents CH, and $G^4$ represents a nitrogen atom, $R^{3c}$ represents a hydrogen atom, $R^{4c}$ represents a methoxy group and $R^{3b}$ represents any substituents indicated in Table 7 to Table 15 (hereinafter, referred to as Compound Class $SX_{529}$).

A compound represented by formula (L-18) wherein $G^1$ represents CH, and $G^4$ represents a nitrogen atom, $R^{3c}$ represents a hydrogen atom, $R^{4c}$ represents a chlorine atom and $R^{3b}$ represents any substituents indicated in Table 7 to Table 15 (hereinafter, referred to as Compound Class $SX_{530}$).

A compound represented by formula (L-18) wherein $G^1$ represents CH, and $G^4$ represents a nitrogen atom, $R^{3c}$ represents a hydrogen atom, $R^{4c}$ represents a bromine atom and $R^{3b}$ represents any substituents indicated in Table 7 to Table 15 (hereinafter, referred to as Compound Class $SX_{531}$).

A compound represented by formula (L-18) wherein $G^1$ represents CH, and $G^4$ represents a nitrogen atom, $R^{3c}$ represents a hydrogen atom, $R^{4c}$ represents a cyano group and $R^{3b}$ represents any substituents indicated in Table 7 to Table 15 (hereinafter, referred to as Compound Class $SX_{532}$).

A compound represented by formula (L-18) wherein $G^1$ represents a nitrogen atom, and $G^4$ represents CH, $R^{3b}$ represents a hydrogen atom, $R^{4c}$ represents a hydrogen atom and $R^{3c}$ represents any substituents indicated in Table 7 to Table 15 (hereinafter, referred to as Compound Class $SX_{533}$).

A compound represented by formula (L-18) wherein $G^1$ represents a nitrogen atom, and $G^4$ represents CH, $R^{3b}$ represents a hydrogen atom, $R^{4c}$ represents a methyl group and $R^{3c}$ represents any substituents indicated in Table 7 to Table 15 (hereinafter, referred to as Compound Class $SX_{534}$).

A compound represented by formula (L-18) wherein $G^1$ represents a nitrogen atom, and $G^4$ represents CH, $R^{3b}$ represents a hydrogen atom, $R^{4c}$ represents an ethyl group and $R^{3c}$ represents any substituents indicated in Table 7 to Table 15 (hereinafter, referred to as Compound Class $SX_{535}$).

A compound represented by formula (L-18) wherein $G^1$ represents a nitrogen atom, and $G^4$ represents CH, $R^{3b}$ represents a hydrogen atom, $R^{4c}$ represents a methoxy group and $R^{3c}$ represents any substituents indicated in Table 7 to Table 15 (hereinafter, referred to as Compound Class $SX_{536}$).

A compound represented by formula (L-18) wherein $G^1$ represents a nitrogen atom, and $G^4$ represents CH, $R^{3b}$ represents a hydrogen atom, $R^{4c}$ represents a chlorine atom and $R^{3c}$ represents any substituents indicated in Table 7 to Table 15 (hereinafter, referred to as Compound Class $SX_{537}$).

A compound represented by formula (L-18) wherein $G^1$ represents a nitrogen atom, and $G^4$ represents CH, $R^{3b}$ represents a hydrogen atom, $R^{4c}$ represents a bromine atom and $R^{3c}$ represents any substituents indicated in Table 7 to Table 15 (hereinafter, referred to as Compound Class $SX_{538}$).

A compound represented by formula (L-18) wherein $G^1$ represents a nitrogen atom, and $G^4$ represents CH, $R^{3b}$ represents a hydrogen atom, $R^{4c}$ represents a cyano group and $R^{3c}$ represents any substituents indicated in Table 7 to Table 15 (hereinafter, referred to as Compound Class $SX_{539}$).

A compound represented by formula (L-18) wherein $G^1$ represents a nitrogen atom, and $G^4$ represents CH, $R^{3c}$ represents a hydrogen atom, $R^{4c}$ represents a hydrogen atom and $R^{3b}$ represents any substituents indicated in Table 7 to Table 15 (hereinafter, referred to as Compound Class $SX_{540}$).

A compound represented by formula (L-18) wherein $G^1$ represents a nitrogen atom, and $G^4$ represents CH, $R^{3c}$ represents a hydrogen atom, $R^{4c}$ represents a methyl group and $R^{3b}$ represents any substituents indicated in Table 7 to Table 15 (hereinafter, referred to as Compound Class $SX_{541}$).

A compound represented by formula (L-18) wherein $G^1$ represents a nitrogen atom, and $G^4$ represents CH, $R^{3c}$ represents a hydrogen atom, $R^{4c}$ represents an ethyl group and $R^{3b}$ represents any substituents indicated in Table 7 to Table 15 (hereinafter, referred to as Compound Class $SX_{542}$).

A compound represented by formula (L-18) wherein $G^1$ represents a nitrogen atom, and $G^4$ represents CH, $R^{3c}$ represents a hydrogen atom, $R^{4c}$ represents a methoxy group and $R^{3b}$ represents any substituents indicated in Table 7 to Table 15 (hereinafter, referred to as Compound Class $SX_{543}$).

A compound represented by formula (L-18) wherein $G^1$ represents a nitrogen atom, and $G^4$ represents CH, $R^{3c}$ represents a hydrogen atom, $R^{4c}$ represents a chlorine atom and $R^{3b}$ represents any substituents indicated in Table 7 to Table 15 (hereinafter, referred to as Compound Class $SX_{544}$).

A compound represented by formula (L-18) wherein $G^1$ represents a nitrogen atom, and $G^4$ represents CH, $R^{3c}$ represents a hydrogen atom, $R^{4c}$ represents a bromine atom and $R^{3b}$ represents any substituents indicated in Table 7 to Table 15 (hereinafter, referred to as Compound Class $SX_{545}$).

A compound represented by formula (L-18) wherein $G^1$ represents a nitrogen atom, and $G^4$ represents CH, $R^{3c}$ represents a hydrogen atom, $R^{4c}$ represents a cyano group and $R^{3b}$ represents any substituents indicated in Table 7 to Table 15 (hereinafter, referred to as Compound Class $SX_{546}$).

A compound represented by formula (L-19):

(L-19)

[Chemical structure showing $F_3C$-pyridyl group connected to a pyrimidinone ring with $R^{4c}$ substituent, linked to an imidazo-fused ring system bearing $(O)_2S$-$CH_3$ group, $G^1$, $G^4$, $R^{3b}$, and $R^{3c}$ substituents]

(hereinafter, referred to as compound (L-19)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{547}$).

A compound represented by formula (L-19) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{548}$).

A compound represented by formula (L-19) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{549}$).

A compound represented by formula (L-19) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{550}$).

A compound represented by formula (L-19) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{551}$).

A compound represented by formula (L-19) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{552}$).

A compound represented by formula (L-19) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{553}$).

A compound represented by formula (L-19) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{554}$).

A compound represented by formula (L-19) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{555}$).

A compound represented by formula (L-19) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{556}$).

A compound represented by formula (L-19) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{555}$).

A compound represented by formula (L-19) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{558}$).

A compound represented by formula (L-19) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{559}$).

A compound represented by formula (L-19) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{560}$).

A compound represented by formula (L-19) wherein $G^1$ represents CH, $G^4$ represents a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{561}$).

A compound represented by formula (L-19) wherein $G^1$ a hydrogen atom, $R^{4c}$ represents a methyl group, and $R^{3c}$ represents any substituents indicated in Table 7 to Table 15 (hereinafter, referred to as Compound Class $SX_{562}$).

A compound represented by formula (L-19) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{563}$).

A compound represented by formula (L-19) wherein $G^1$ represents CH, $G^4$ represents a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{564}$).

A compound represented by formula (L-19) wherein $G^1$ represents CH, $G^4$ represents a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{565}$).

A compound represented by formula (L-19) wherein $G^1$ represents CH, $G^4$ represents a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{566}$).

A compound represented by formula (L-19) wherein $G^1$ represents CH, $G^4$ represents a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{567}$).

A compound represented by formula (L-19) wherein $G^1$ represents CH, $G^4$ represents a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{558}$).

A compound represented by formula (L-19) wherein $G^1$ represents CH, $G^4$ represents a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{569}$).

A compound represented by formula (L-19) wherein $G^1$ represents CH, $G^4$ represents a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{570}$).

A compound represented by formula (L-19) wherein $G^1$ represents CH, $G^4$ represents a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{571}$).

A compound represented by formula (L-19) wherein $G^1$ represents CH, $G^4$ represents a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{572}$).

A compound represented by formula (L-19) wherein $G^1$ represents CH, $G^4$ represents a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{573}$).

A compound represented by formula (L-19) wherein $G^1$ represents CH, $G^4$ represents a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{574}$).

A compound represented by formula (L-19) wherein $G^1$ represents a nitrogen atom, $G^4$ represents CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{575}$).

A compound represented by formula (L-19) wherein $G^1$ represents a nitrogen atom, $G^4$ represents CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{576}$).

A compound represented by formula (L-19) wherein $G^1$ represents CH, $G^4$ represents a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{577}$).

A compound represented by formula (L-19) wherein $G^1$ represents a nitrogen atom, $G^4$ represents CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{578}$).

A compound represented by formula (L-19) wherein $G^1$ represents a nitrogen atom, $G^4$ represents CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{579}$).

A compound represented by formula (L-19) wherein $G^1$ represents a nitrogen atom, $G^4$ represents CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{580}$).

A compound represented by formula (L-19) wherein $G^1$ represents a nitrogen atom, $G^4$ represents CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{581}$).

A compound represented by formula (L-19) wherein $G^1$ represents a nitrogen atom, $G^4$ represents CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{592}$).

A compound represented by formula (L-19) wherein $G^1$ represents a nitrogen atom, $G^4$ represents CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{593}$).

A compound represented by formula (L-19) wherein $G^1$ represents a nitrogen atom, $G^4$ represents CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{584}$).

A compound represented by formula (L-19) wherein $G^1$ represents a nitrogen atom, $G^4$ represents CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{585}$).

A compound represented by formula (L-19) wherein $G^1$ represents a nitrogen atom, $G^4$ represents CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{586}$).

A compound represented by formula (L-19) wherein $G^1$ represents a nitrogen atom, $G^4$ represents CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{587}$).

A compound represented by formula (L-19) wherein $G^1$ represents a nitrogen atom, $G^4$ represents CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{588}$).

A compound represented by formula (L-20):

(hereinafter, referred to as compound (L-20)), wherein $G^1$ and $G^4$ represent CH, $R^{3b}$ and $R^{4c}$ represent a hydrogen atom, and $R^{3c}$ represents any substituents indicated in Table 7 to Table 15 (hereinafter, referred to as Compound Class $SX_{589}$).

A compound represented by formula (L-20) wherein $G^1$ and $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{550}$).

A compound represented by formula (L-20) wherein $G^1$ and $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{591}$).

A compound represented by formula (L-20) wherein $G^1$ and $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{592}$).

A compound represented by formula (L-20) wherein $G^1$ and $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{593}$).

A compound represented by formula (L-20) wherein $G^1$ and $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{594}$).

A compound represented by formula (L-20) wherein $G^1$ and $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{595}$).

A compound represented by formula (L-20) wherein $G^1$ and $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{596}$).

A compound represented by formula (L-20) wherein $G^1$ and $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{597}$).

A compound represented by formula (L-20) wherein $G^1$ and $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{598}$).

A compound represented by formula (L-20) wherein $G^1$ and $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{599}$).

A compound represented by formula (L-20) wherein $G^1$ and $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{600}$).

A compound represented by formula (L-20) wherein $G^1$ and $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{601}$).

A compound represented by formula (L-20) wherein $G^1$ and $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{602}$).

A compound represented by formula (L-20) wherein $G^1$ represents CH, $G^4$ represent a nitrogen atom, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{603}$).

A compound represented by formula (L-20) wherein $G^1$ represents CH, $G^4$ represent a nitrogen atom, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{604}$).

A compound represented by formula (L-20) wherein $G^1$ represents CH, $G^4$ represent a nitrogen atom, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{605}$).

A compound represented by formula (L-20) wherein $G^1$ represents CH, $G^4$ represent a nitrogen atom, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{606}$).

A compound represented by formula (L-20) wherein $G^1$ represents CH, $G^4$ represent a nitrogen atom, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{607}$).

A compound represented by formula (L-20) wherein $G^1$ represents CH, $G^4$ represent a nitrogen atom, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{608}$).

A compound represented by formula (L-20) wherein $G^1$ represents CH, $G^4$ represent a nitrogen atom, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{609}$).

A compound represented by formula (L-20) wherein $G^1$ represents CH, $G^4$ represent a nitrogen atom, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{610}$).

A compound represented by formula (L-20) wherein $G^1$ represents CH, $G^4$ represent a nitrogen atom, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{611}$).

A compound represented by formula (L-20) wherein $G^1$ represents CH, $G^4$ represent a nitrogen atom, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{612}$).

A compound represented by formula (L-20) wherein $G^1$ represents CH, $G^4$ represent a nitrogen atom, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{613}$).

A compound represented by formula (L-20) wherein $G^1$ represents CH, $G^4$ represent a nitrogen atom, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{614}$).

A compound represented by formula (L-20) wherein $G^1$ represents CH, $G^4$ represent a nitrogen atom, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{615}$).

A compound represented by formula (L-20) wherein $G^1$ represents CH, $G^4$ represent a nitrogen atom, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{616}$).

A compound represented by formula (L-20) wherein $G^1$ represents a nitrogen atom, $G^4$ represent CH, $R^{3b}$ represents a hydrogen atom, $R^{4c}$ represents a hydrogen atom, and $R^{3c}$ represents any substituents indicated in Table 7 to Table 15 (hereinafter, referred to as Compound Class $SX_{617}$).

A compound represented by formula (L-20) wherein $G^1$ represents a nitrogen atom, $G^4$ represent CH, $R^{3b}$ represents a hydrogen atom, $R^{4c}$ represents a methyl group, and $R^{3c}$ represents any substituents indicated in Table 7 to Table 15 (hereinafter, referred to as Compound Class $SX_{618}$).

A compound represented by formula (L-20) wherein $G^1$ represents a nitrogen atom, $G^4$ represent CH, $R^{3b}$ represents a hydrogen atom, $R^{4c}$ represents an ethyl group, and $R^{3c}$ represents any substituents indicated in Table 7 to Table 15 (hereinafter, referred to as Compound Class $SX_{619}$).

A compound represented by formula (L-20) wherein $G^1$ represents a nitrogen atom, $G^4$ represent CH, $R^{3b}$ represents a hydrogen atom, $R^{4c}$ represents a methoxy group, and $R^{3c}$ represents any substituents indicated in Table 7 to Table 15 (hereinafter, referred to as Compound Class $SX_{620}$).

A compound represented by formula (L-20) wherein $G^1$ represents a nitrogen atom, $G^4$ represent CH, $R^{3b}$ represents a hydrogen atom, $R^{4c}$ represents a chlorine atom, and $R^{3c}$ represents any substituents indicated in Table 7 to Table 15 (hereinafter, referred to as Compound Class $SX_{621}$).

A compound represented by formula (L-20) wherein $G^1$ represents a nitrogen atom, $G^4$ represent CH, $R^{3b}$ represents a hydrogen atom, $R^{4c}$ represents a bromine atom, and $R^{3c}$ represents any substituents indicated in Table 7 to Table 15 (hereinafter, referred to as Compound Class $SX_{622}$).

A compound represented by formula (L-20) wherein $G^1$ represents a nitrogen atom, $G^4$ represent CH, $R^{3b}$ represents a hydrogen atom, $R^{4c}$ represents a cyano group, and $R^{3c}$ represents any substituents indicated in Table 7 to Table 15 (hereinafter, referred to as Compound Class $SX_{623}$).

A compound represented by formula (L-20) wherein $G^1$ represents a nitrogen atom, $G^4$ represent CH, $R^{3c}$ represents a hydrogen atom, $R^{4c}$ represents a hydrogen atom, and $R^{3b}$ represents any substituents indicated in Table 7 to Table 15 (hereinafter, referred to as Compound Class $SX_{624}$).

A compound represented by formula (L-20) wherein $G^1$ represents a nitrogen atom, $G^4$ represent CH, $R^{3c}$ represents a hydrogen atom, $R^{4c}$ represents a methyl group, and $R^{3b}$ represents any substituents indicated in Table 7 to Table 15 (hereinafter, referred to as Compound Class $SX_{625}$).

A compound represented by formula (L-20) wherein $G^1$ represents a nitrogen atom, $G^4$ represent CH, $R^{3c}$ represents a hydrogen atom, $R^{4c}$ represents an ethyl group, and $R^{3b}$ represents any substituents indicated in Table 7 to Table 15 (hereinafter, referred to as Compound Class $SX_{626}$).

A compound represented by formula (L-20) wherein $G^1$ represents a nitrogen atom, $G^4$ represent CH, $R^{3c}$ represents a hydrogen atom, $R^{4c}$ represents a methoxy group, and $R^{3b}$ represents any substituents indicated in Table 7 to Table 15 (hereinafter, referred to as Compound Class $SX_{627}$).

A compound represented by formula (L-20) wherein $G^1$ represents a nitrogen atom, $G^4$ represent CH, $R^{3c}$ represents a hydrogen atom, $R^{4c}$ represents a chlorine atom, and $R^{3b}$ represents any substituents indicated in Table 7 to Table 15 (hereinafter, referred to as Compound Class $SX_{628}$).

A compound represented by formula (L-20) wherein $G^1$ represents a nitrogen atom, $G^4$ represent CH, $R^{3c}$ represents a hydrogen atom, $R^{4c}$ represents a bromine atom, and $R^{3b}$ represents any substituents indicated in Table 7 to Table 15 (hereinafter, referred to as Compound Class $SX_{629}$).

A compound represented by formula (L-20) wherein $G^1$ represents a nitrogen atom, $G^4$ represent CH, $R^{3c}$ represents a hydrogen atom, $R^{4c}$ represents a cyano group, and $R^{3b}$ represents any substituents indicated in Table 7 to Table 15 (hereinafter, referred to as Compound Class $SX_{630}$).

The compound of the present invention may be mixed or combined with one or more kinds of ingredients selected from a group consisting of the following Group (a), Group (b), Group (c), Group (d), Group (e), Group (f), Group (g), and Group (h) (hereinafter, referred to as Present ingredient).

The above-mentioned mixing or combining represents a use of the Present compound and the Present ingredient at same time, separately or at certain intervals.

When the Present compound and the present ingredient are used at the same time, the Present compound and the Present ingredient may be contained in separate formulations respectively or may be contained in the same one formulation.

One aspect of the present invention is a composition comprising one or more ingredients selected from Group (a) or Group (b) as well as the Present compound (hereinafter, referred to as Composition A).

Group (a) is a group consisting of
each active ingredient as Acetylcholinesterase inhibitors (for example, carbamate insecticides, or organophosphorus insecticides), GABA-gated chloride channel blockers (for example, phenylpyrazol insecticides), Sodium channel modulators (for example, pyrethroid insecticides), Nicotinic acetylcholine receptor competitive modulators (for example, neonicotinoid insecticides), Nicotinic acetylcholine receptor allosteric modulators, Glutamatergic chlorine ion channel allosteric modulators (for example, macrolide insecticides), Juvenile hormone mimic, Multisite inhibitors, chordotonal organ TRPV channel modulators, Mites growth inhibitors, Mitochondria ATP biosynthetic enzyme inhibitors, Uncouplers of oxidative phosphorylation, Nicotinic acetylcholine receptor channel blocker (for example, Nereistoxin insecticides), Chitin synthesis inhibitors, Molting inhibitors, Ecdysone receptor agonist, Octopamine receptor agonist, Inhibitors of Mitochondrial electron transport system complex I, II, III and IV, Voltage-dependent sodium channel blockers, Acetyl CoA carboxylase inhibitor, Ryanodine receptor modulator (for example, Diamide insecticides), Chordotonal organ modulators, Microbial pesticides; and
the other insecticidal, miticidal or nematicidal active ingredients.

These ingredients are classified as a class based on the action mechanism of IRAC.

Group (b) is a group consisting of
Nucleic acid synthesis inhibitors (for example, Phenylamide fungicides, or Acylamino acid fungicides), cell division and cytoskeleton inhibitors (for example, MBC fungicides), Respiratory inhibitors (for example, QoI fungicides or Qil fungicides), Amino acid synthesis and protein synthesis inhibitors (for example, anilinopyridine fungicides), Signal transduction inhibitors, Lipid synthesis and membrane synthesis inhibitors, sterol biosynthesis inhibitors (for example, DMI fungicides such as triazole), cell wall synthesis inhibitors, Melanin synthesis inhibitors, Plant defense inducers, Other action point contact active fungicides, Microbial fungicides, and the other fungicidal ingredients. These are classified as a class based on the action mechanism of FRAC.

Group (c) is a plant growth modulating ingredient group (including Mycorrhizal fungi, and Root nodule bacteria).

Group (d) is a phytotoxicity-reducing ingredient group.

Group (e) is a synergist group.

Group (f) is a group consisting of repellent components consisting of bird repellant components, insect repellant components, and animal repellant components.

Group (g) is a molluscicidal component group.

Group (h) is an insect pheromone group.

Examples of the combination of the Present ingredient and the Present compound are described below. For example, alanycarb+SX represents a combination of alanycarb and SX. The symbol of "SX" represents any one of the Present compound selected from the Compound Class $SX_1$ to the Compound Class $SX_{630}$. Also, all of the below-mentioned present active ingredient are known ingredients, and are commercially available or may be produced by the known method. If the present ingredient is a bacterium, it is available from the bacterial authority depository. The numerical number in bracket represents a CAS RN (®).

Combination of the Present ingredient of the above Group (a) and the Present compound:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of Celastrus angulatus+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, fluopyram+SX, flupyradifurone+SX, fluralaner+SX, fluvalinate+SX, fluxametamide+SX, formetanate+SX, fosthiazate+SX, furamethrin+SX, furathiocarb+SX, gamma-cyhalothrin+SX, halfenprox+SX, halofenozide+SX, heptafluthrin+SX, heptenophos+SX, hexaflumuron+SX, hexythiazox+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemoctin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, omethoate+SX, oxamyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultapdisodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, vamidothion+SX, XMC (3,5-dimethylphenyl N-methylcarbamate)+SX, xylylcarb+SX, zeta-cypermethrin+SX, zinc phosphide+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 2-[3-(ethanesulfonyl)pyridin-2-yl]-5-(trifluoromethanesulfonyl)benzoxazole (1616678-32-0)+SX, 4-[5-(3,5-dichlorophenyl)-5-(trifluoromethyl)-4,5-dihydro-1,2-oxazol-3-yl]-2-methyl-N-(1-oxothiethan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus+SX, *Anticarsia gemmatalis* mNPV+SX, *Autographa californica* mNPV FV #11+SX, *Cydia pomonella* GV V15+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* 1-1582+SX, *Bacillus megaterium*+SX, *Bacillus* sp.AQ175+SX, *Bacillus* sp.AQ177+SX, *Bacillus* sp.AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. *Aizawai* ABTS-1857+SX, *Bacillus thuringiensis* subsp. *Aizawai* AM65-52+SX, *Bacillus thuringiensis* subsp. *Aizawai* GC-91+SX, *Bacillus thuringiensis* subsp. *Aizawai* Serotype H-7+SX, *Bacillus thuringiensis* subsp. *Kurstaki* ABTS351+SX, *Bacillus thuringiensis* subsp. *Kurstaki* BMP123+SX, *Bacillus thuringiensis* subsp. *Kurstaki* EG234+SX, *Bacillus thuringiensis* subsp. *Kurstaki* EG7841+SX, *Bacillus thuringiensis* subsp. *Kurstaki* EVB113-19+SX, *Bacillus thuringiensis* subsp. *Kurstaki* F810+SX, *Bacillus thuringiensis* subsp. *Kurstaki* HD-1+SX, *Bacillus thuringiensis* subsp. *Kurstaki* PB54+SX, *Bacillus thuringiensis* subsp. *Kurstaki* SA-11+SX, *Bacillus thuringiensis* subsp. *Kurstaki* SA-12+SX, *Bacillus thuringiensis* subsp. *Tenebriosis* NB176+SX, *Bacillus thuringiensis* subsp. *Thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *japonensis buibui*+SX, *Bacillus thuringiensis* var. *san diego* M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX,

*Lagenidium giganteum*+SX, *Lecanicillium lecanii* KV01+SX, *Metarhizium arisopliae* F52+SX, *Metarhizium anisopliae* var. *acridum*+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* NCIM1312+SX.

Combination of the Present ingredient of the above Group (b) and the Present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper chloride+SX, basic copper sulfate+SX, benalaxyl+SX, benalaxyl-M+SX, benodanil+SX, benomyl+SX, benthiavalicarb+SX, benthivalicarb-isopropyl+SX, benzcvindiflupyr+SX, binapacryl+SX, biphenyl+SX, bitertanol+SX, bixafen+SX, blasticidin-S+SX, boscalid+SX, bromuconazole+SX, bupirimate+SX, captafol+SX, captan+SX, carbendazim+SX, carboxin+SX, carpropamid+SX, chinomethionat+SX, chloroneb+SX, chlorothalonil+SX, chlozolinate+SX, colletochlorin B+SX, copper(II) hydroxide+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, imethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, fluazinam+SX, fludioxonil+SX, flufenoxystrobin+SX, fluindapyr+SX, flumorph+SX, fluopicolide+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fuberidazole+SX, furalaxyl+SX, furametpyr+SX, guazatine+SX, hexaconazole+SX, hymexazole+SX, imazalil+SX, imibenconazole+SX, iminoctadine+SX, inpyrfluxam+SX, iodocarb+SX, ipconazole+SX, ipfentrifluconazole+SX, iprobenfos+SX, iprodione+SX, iprovalicarb+SX, isofetamid+SX, soflucypram+SX, isoprothiolane+SX, isopyrazam+SX, isotianil+SX, kasugamycin+SX, kresoximmethyl+SX, laminarin+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazcle+SX, methasulfocarb+SX, metiram+SX, metominostrobin+SX, metrafenone+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phthalide+SX, picarbutrazox+SX, picoxystrobin+SX, piperalin+SX, polyoxins+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyraziflumid+SX, pyrazophos+SX, pyribencarb+SX, pyributicarb+SX, pyrifenox+SX, pyrimethanil+SX, pyrimorph+SX, pyriofenone+SX, pyrisoxazole+SX, pyroquilon+SX, quinofumelin+SX, quinoxyfen+SX, quintozene+SX, sedaxane+SX, silthiofam+SX, simeconazole+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, zineb+SX, ziram+SX, zoxamide+SX, 3-difluoromethyl-N-methoxy-1-methyl-N-[(1R)-1-methyl-2-(2,4,6-trichlorophenyl)ethyl]pyrazol-4-carboxamide (1639015-48-7)+SX, 3-difluoromethyl-N-methoxy-1-methyl-N-[(1S)-1-methyl-2-(2,4,6-trichlorophenyl)ethyl]pyrazol-4-carboxamide (1639015-49-8)+SX, 3-difluoromethyl-1-methyl-N-(1,1,3-trimethylindan-4-yl)pyrazole-4-carboxamide (141573-94-6)+SX, 3-(difluoromethyl)-1-methyl-N-[(3R)-1,1,3-trimethylindan-4-yl]pyrazole-4-carboxamide (1352994-67-2)+SX, 3-difluoromethyl-N-[(3R)-7-fluoro-1,1,3-trimethylindan-4-yl]-1-methylpyrazole-4-carboxamide (1513466-73-3)+SX, 3-chloro-5-phenyl-6-methyl-4-(2,6-difluorophenyl)pyridazine (1358061-55-8)+SX, N'-[4-({3-[(4-chlorophenyl)methyl]-1,2,4-thiadiazol-5-yl}oxy-2,5-dimethylphenyl]-N-ethyl-N-methylmethaneimidamide (1202781-91-6+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidine-2(1H)-one (1616664-98-2)+SX, N'-(2,5-dimethyl-4-phenoxyphenyl)-N-ethyl-N-methyl-methaneimidamide (1052688-31-9)+SX, N'-(4-[(4,5-dichlorothiazol-2-yl)oxy]-2,5-dimethylphenyl)-N-ethyl-N-methyl-methaneimidamide (929908-57-6)+SX, ethyl (2Z)-3-amino-2-cyano-3-phenylacrylate (39491-78-6)+SX, N-{(2-chlorothiazol-5-yl)methyl}-N-ethyl-6-methoxy-3-nitropyridine-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX, α-[3-(4-chloro-2-fluorophenyl)-5-(2,4-difluorophenyl)-4-isoxazolyl]-3-pyridine methanol (1229605-96-2)+SX, (αS)-[3-(4-chloro-2-fluorophenyl)-5-(2,4-difluorophenyl)-4-isoxazolyl]-3-pyridine methanol (1229606-46-5)+SX, (αS)-[3-(4-chloro-2-fluorophenyl)-5-(2,4-difluorophenyl)-4-isoxazolyl]-3-pyridine methanol (1229606-46-5)+SX), (αR)-[3-(4-chloro-2-fluorophenyl)-5-(2,4-difluorophenyl)-4-isoxazolyl]-3-pyridine methanol (1229606-02-3)+SX), 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-([(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanate (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1)+SX, 1-{[(2S,3R)-3-(2-chlorophenyl)-2-(2,4-difluorophenyl)oxiran-2-yl]methyl)-1H-1,2,4-triazol-5-yl thiocyanate (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R2S,5S)-5-(4-chlorobenzyl)-2-chloromethyl-2-methyl-1-(1H-1,2,4-triazol-1-ylmethyl)cyclopentanol (1801930-06-2)+SX, (1S,2R5R)-5-(4-chlorobenzyl)-2-chloromethyl-2-methyl-1-(1H-1,2,4-triazol-1-ylmethyl)cyclopentanol (1801930-07-3)+SX, 1.0 (1R2R5S)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R2R5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R2S, 5R)-5-(4-chlorobenzyl)-2-chloromethyl-2-methyl-1-(1H-1,2,4-triazol-1-ylmethyl)cyclopentanol (1801919-57-2)+SX, (1S, 2R5S)-5-(4-chlorobenzyl)-2-chloromethyl-2-methyl-1-(1H-1,2,4-triazol-1-ylmethyl)cyclopentanol (1801919-58-3)+SX, Methyl=3-[4-(chlorophenyl)methyl]-2-hydroxy-1-methyl-2-(1H-1,2,4-triazol-1-ylmethyl)cyclopentane carboxylate (1791398-02-1)+SX, Methyl=(1R2S, 3S)-3-[(4-chlorophenyl)methyl]-2-hydroxy-1-methyl-2-(1H-1,2,4-triazol-1-ylmethyl)cyclopentane carboxylate+SX, Methyl=(1S,2R,3R)-3-[(4-chlorophenyl)methyl]-2-hydroxy-1-methyl-2-(1H-1,2,4-triazol-1-ylmethyl)cyclopentane carboxylate+SX, Methyl=(1R2R, 3R)-3-[(4-chlorophenyl)methyl]-2-hydroxy-1-methyl-2-(1H-1,2,4-triazol-1-ylmethyl)cyclopentane carboxylate+SX, Methyl=(1S,2S, 3S)-3-[(4-chlorophenyl)methyl]-2-hydroxy-1-methyl-2-(1H-1,2,4-triazol-1-ylmethyl)cyclopentane carboxylate+SX, Methyl=(1R2R, 3S)-3-[(4-chlorophenyl)methyl]-2-hydroxy-1-methyl-2-(1H-1,2,4-triazol-1-ylmethyl)cyclopentane carboxylate+SX, Methyl=(1S,2S, 3R)-3-[(4-chlorophenyl)methyl]-2-hydroxy-1-methyl-2-(1H-1,2,4-triazol-1-ylmethyl)cyclopentane carboxylate+SX, Methyl=(1R2S, 3R)-3-[(4-chlorophenyl)methyl]-2-hydroxy-1-methyl-2-(1H-1,2,4-triazol-1-ylmethyl)cyclopentane carboxylate+SX, Methyl=(1S,2R, 3S)-3-[(4-chlorophenyl)methyl]-2-hydroxy-1-methyl-2-(1H-1,2,4-triazol-1-ylmethyl) cyclopentane carboxylate+SX, 2-chloromethyl-5-(4-fluorobenzyl)-2-methyl-1-(1H-1,2,4-triazol-1-ylmethyl)cyclopentanol (1394057-13-6)+SX, (1R2S, 5S)-2-chloromethyl-5-(4-fluorobenzyl)-2-methyl-1-(1H-1,2,4-triazol-1-ylmethyl)cyclopentanol (1801930-08-4)+SX, (1S,2R5R)-2-chloromethyl-5-(4-fluorobenzyl)-2-methyl-1-(1H-1,2,4-triazol-1-ylmethyl)cyclopentanol (1801930-09-5)+SX, (1R2R5R)-2-chloromethyl-5-(4-fluorobenzyl)-2-methyl-1-(1H-1,2,4-triazol-1-ylmethyl)cyclopentanol (1638898-08-4)+SX, (1S,2S, 5S)-2-chloromethyl-5-(4-fluorobenzyl)-2-methyl-1-(1H-1,2,4-triazol-1-ylmethyl)cyclopentanol (1638898-10-8)+SX, (1R2R5S)-2-chloromethyl-5-(4-fluorobenzyl)-2-methyl-1-(1H-1,2,4-triazol-1-ylmethyl)cyclopentanol (1638898-13-1)+SX, (1S,2S, 5R)-2-chloromethyl-5-(4-fluorobenzyl)-2-methyl-1-(1H-1,2,4-triazol-1-ylmethyl)cyclopentanol (1638898-16-4)+SX, (1R2S, 5R)-2-chloromethyl-5-(4-fluorobenzyl)-2-methyl-1-(1H-1,2,4-triazol-1-ylmethyl)cyclopentanol (1638898-20-0)+SX, (1S,2R5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy)phenyl]-1-(1,2,4-triazol-1-yl)pent-3-yne-2-ol (1801919-59-4)+SX, (R)-2-[4-(4-chlorophenoxy)-2-(trifluoromethyl)phenyl]-1-(1,2,4-triazol-1-yl)propane-2-ol (1616236-94-2)+SX, (R)-1-[4-(4-chlorophenoxy)-2-(trifluoromethyl)phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butane-2-ol (1801919-61-8)+SX, 3-[5-(4-chlorophenyl)-2,3-dimethyl-1,2-oxazolydin-3-yl]pyridine (847749-37-5)+SX, *Agrobacterium radiobactor* K1026+SX, *Agrobacterium radiobactor* K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SB3086+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* D747+SX, *Bacillus subtilis* DB101+SX, *Bacillus subtilis* GB03+SX, *Bacillus subtilis* HAI0404+SX, *Bacillus subtilis* IAB/BS03+SX, *Bacillus subtilis* MBI600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* O+SX, *Candida saitoana*+SX, *Chaetomium cupreum*+SX, *Clonostachys rosea*+SX, *Coniothyrium minitans* CGMCC8325+SX, *Coniothyrium minitans* CON/M/91-8+SX, *cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas syringae* 742RS+SX, *Pseudomonas syringae* MA-4+SX, *Pseudozyma flocculosa* PF-A22UL+SX, *Pseudomonas rhodesiae* HAI-0804+SX, *Pythium oligandrum* DV74+SX, *Streptomyces griseoviridis* K61+SX, *Streptomyces lydicus* WYCD108US+SX, *Strepto-*

*myces lydicus* WYEC108+SX, *Talaromyces flavus* SAY-Y-94-01+SX, *Trichoderma asperellum* ICC012+SX, *Trichoderma asperellum* T34+SX, *Trichoderma atroviride* CNCM 1-1237+SX, *Trichoderma atroviride* LC52+SX, *Trichoderma atroviride* SC1+SX, *Trichoderma atroviride* SKT-1+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum* kd+SX, *Trichoderma harzianum* MO1+SX, *Trichoderma harzianum* SF+SX, *Trichoderma harzianum* T22+SX, *Trichoderma harzianum* T39+SX, *Trichoderma polysporum* IMI206039+SX, *Trichoderma stromaticum*+SX, *Trichoderma virens* GL-21+SX, *Variovorax paradoxus* CGF4526+SX, and Harpin protein+SX.

Combination of the Present ingredient of the above Group (c) and the Present compound:

1-methylcyclopropene+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequatchloride+SX, chlorpropham+SX, choline chloride+SX, cloprop+SX, cyanamide+SX, cyanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalene-1-yl)acetamide+SX, [4-oxo-4-(2-phenyethyl)amino]butyric acid+SX, Methyl 5-(trifluoromethyl) benzo[b]thiophen-2-carboxylate+SX, 3-[(6-chloro-4-phenylquinazolin-2-yl)amino]-1-propanol+SX, isoflavone formononetin+SX, *Glomus* spp.+SX, *Glomus intraradices*+SX, *Glomus mosseae*+SX, *Glomus aggregatum*+SX, *Glomus etunicatum*+SX, *Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+SX, *Rhizobium fredii*+SX, *Rhizobium loti*+SX, *Rhizobium trifolii*+SX, and *Rhizobium tropici*+SX.

Combination of the Present ingredient of the above Group (d) and the Present compound:

allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dichloroacetyl)-1-oxa-4-azaspiro [4.5] decane)+SX, CL-304415 (4-carboxy-3,4-dihydro-2H-1-benzopyran-4-acetic acid)+SX, CSB (1-bromo-4-[(chloromethyl)sulfonyl] benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R28725 (3-(dichloroacetyl)-2,2-dimethyl-1,3-oxazolidine)+SX, R29148 (3-(dichloroacetyl)-2,2,5-trimethyl-1,3-oxazolidine)+SX, and TI-35 (1-(dichloroacetyl)azepane)+SX.

Combination of the Present ingredient of the above Group (e) and the Present compound:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)+SX, and TPP (triphenyl phosphate)+SX.

Combination of the Present ingredient of the above Group (f) and the Present compound:

anthraquinone+SX, chloralose+SX, acrep+SX, butopyronoxyl+SX, camphor+SX, d-camphor+SX, carboxide+SX, dibutyl phthalate+SX, deet+SX, dimethyl carbate+SX, dimethyl phthalate+SX, dibutyl succinate+SX, dibutyl adipate+SX, ethchexadiol+SX, hexamide+SX, icaridin+SX, methoquin-butyl+SX, methylneodecanamide+SX, 2-(octylthio) ethanol+SX, butoxypolypropylene glycol+SX, oxamate+SX, quwenzhi+SX, quyingding+SX, zengxiaon+SX, rebemide+SX, copper naphthenate+SX, and zinc naphthenate+SX.

Combination of the Present ingredient of the above Group (g) and the Present compound:

bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, and trifenmorph+SX.

Combination of the Present ingredient of the above Group (h) and the Present compound:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethyicyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R5R)-ethyl-1,6-dioxaspiro[4,4]nonane+SX, (2R5S)-ethyl-1,6-dioxaspiro[4,4]nonane+SX, (4R8 R)-4,8-dimethyldecanal+SX, (4R8 S)-4,8-dimethyldecanal+SX, 2,4-dimethyl-5-ethyl-6,8-dioxabicyclo[3,2,1]octane+SX, (−)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyl eugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, and (S)-verbenone+SX.

The ratio of the Present compound to the Present ingredient includes, but not limited thereto, as a ratio by weight (the Present compound:the Present ingredient) 1,000:1 to 1:1,000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, oR11 to 1:10, and the others.

Examples of the pest on which the Present compound has control efficacies include harmful arthropods such as harmful insects, harmful mites, harmful nematodes, and harmful mollusks. Specific examples of the pest include, but are not limited to, the followings.

Hemiptera:

from the family Delphacidae, for example, small brown planthopper (*Laodelphax striatella*), brown planthopper (*Nilaparvata lugens*), white-backed planthopper (*Sogatella furcifera*), corn planthopper (*Peregrinus maidis*), cereal leafhopper (*Javeseila pellucida*), sugarcane leafhopper (*Perkinsiella saccharicida*), and *Tagosodes orizicolus;* from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, Mahanarva posticata, and Mahanarva fimbriolata;

from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigerum*);

from the family Phylloxeridae, for example, grapevine phylloxera (*Daktulosphaira vitifoliae*), Pecan phylloxera (*Phylloxera devastatrix*), Pecan leaf phylloxera (*Phylloxera notabilis*), and Southern pecan leaf phylloxera (*Phylloxera russellae*);

from the family Adelgidae, for example, hemlock woolly aphid (*Adelges tsugae*), balsam woolly aphid (*Adelges piceae*), and *Aphrastasia pectinatae;* from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined buq (*Eysarcoris lewisi*), white-spotted bug (*Eysarcoris ventralis*), *Eysarcoris annamita*, brown marmorated stink bug (*Halyomorpha halys*), green plant bug (*Nezara viridula*), brown stink bug (*Euschistus heros*), red banded stink bug (*Piezodorus guildinii*), *Oebalus pugnax*, and *Dichelops melacanthus;* from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, *Cletus punctiger*, and Australian leaf-footed bug (*Leptoglossus australis*);

from the family Lygaeidae, for example, oriental chinch bug (*Caverelius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae;* from the family Diaspididae, for example, *Abgrallaspis cyanophylli*, red scale (*Aonidiella aurantii*), San José scale (*Diaspidiotus perniciosus*), white peach scale (*Pseudaulacaspis pentagona*), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear psylla (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*);

from the family Cicadidae, for example, Giant Cicada (*Quesada gigas*);

from *Triatoma* spp., for example, *Triatoma infestans*; and the others.

Lepidoptera:

from the family Crambidae, for example, rice stem borer (*Chilo suppressalis*), Darkheaded stem borer (*Chilo polychrysus*), white stem borer (*Scirpophaga innotata*), yellow paddy borer (*Scirpophaga incertulas*), Rupela albina, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*) mealworm moth (*Plodia interpunctella*), and persimmon bark borer (*Euzophera batangensis*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and, corn earworm (*Helicoverpa zea*)), velvetbean caterpillar (*Anticarsia gemmatalis*), cotton leafworm (*Alabama argillacea*), and hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit tortrix (*Adoxophyes orana fasciata*), smaller tea tortrix (*Adoxophyes honmai*), Japanese tea tortrix (*Homona magnanima*), apple tortrix (*Archips fuscocupreanus*), codling moth (*Cydia pomonella*), sugarcane shoot borer (*Tetramoera schistaceana*), bean shoot borer (*Epinotia aporema*), and citrus fruit borer (*Ecdytolopha aurantiana*);

from the family Gracillariidae, for example, tea leaf roller (*Caloptilia theivora*), and Asiatic apple leaf miner (*Phyllonorycter ringoniella*);

from the family Carposinidae, for example, peach fruit moth (*Carposina sasakii*);

from the family Lyonetiidae, for example, Coffee leaf miner (*Leucoptera coffeella*), peach leaf miner (*Lyonetia clerkella*), and *Lyonetia prunifoliella;* from the family Lymantriidae, for example, *Lymantria* spp. (such as gypsy moth (*Lymantria dispar*)) and, *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta;* from the family Arctiidae, for example, American white moth (*Hyphantria cunea*);

from the family Castniidae, for example, giant sugarcane borer (*Telchin licus*);

from the family Cossidae, for example, *Cossus insularis;* from the family Geometridae, for example, *Ascotis selenaria;* from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*, cherry borer (*Synanthedon hector*), and *Synanthedon tenuis;* from the family Hesperiidae, for example, rice skipper (*Parnara guttata*);

from the family Tineidae, for example, casemaking clothes moth (*Tinea translucens*), and common clothes moth (*Tineola bisselliella*); and the others.

Thysanoptera:

from the family Thripidae, for example, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice thrips (*Stenchaetothrips biformis*), and *Echinothrips americanus;* from the family Phlaeothripidae, for example, aculeated rice thrips (*Haplothrips aculeatus*);

and the others.

Diptera:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (*Rhacochlaena japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*);

from the family Phoridae, for example, *Megaselia spiracularis*;

from the family Psychodidae, for example, *Clogmia albipunctata*;

from the family Sciaridae, for example, *Bradysia difformis*;

from the family Cecidomyiidae, for example, hessian fly (*Mayetiola destructor*) and, paddy gall fly (*Orseolia oryzae*);

from the family Diopsidae, for example, *Diopsis macrophthalma*;

from the family Tipulidae, for example, rice crane fly (*Tipula aino*), common cranefly (*Tipula oleracea*), and European cranefly (*Tipula paludosa*);

from the family Culicidae, for example, southern house mosquito (*Culex pipiens pallens*), dengue mosquito (*Aedes aegypti*), Asian tiger mosquito (*Aedes albopictus*), Chinese malaria mosquito (*Anopheles hyracanus sinensis*), *Culex quinquefasciatus, Culex pipiens molestus* Forskal, and brown house mosquito (*Culex quinquefasciatus*);

from the family Simulidae, for example, *Prosimulium yezoensis*, and *Simulium ornatum*;

from the family Tabanidae, for example, *Tabanus trigonus*;

from the family Muscidae, for example, house fly (*Musca domestica*), false stable fly (*Muscina stabulans*), biting house fly (*Stomoxys calcitrans*), and buffalo fly (*Haematobia irritans*);

from the family Tabanidae, for example, *Tabanus trigonus*;

from the family Calliphoridae;

from the family Sarcophagidae;

from the family Chironomidae, for example, *Chironomus plumosus, Chironomus yoshimatsui*, and *Glyptotendipes tokunagai*;

from the family Fannidae;

and the others.

Coleoptera:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), cucurbit beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), cabbage flea beetle (*Phyllotreta cruciferae*), western black flea beetle (*Phyllotreta pusilla*), cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, and tobacco flea beetle (*Epitrix hirtipennis*);

from the family Carabidae, for example, Seedcorn beetle (*Stenolophus lecontei*), and slender seedcorn beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice plant weevil (*Echinocnemus squameus*), rice water weevil (*Lissorhoptrus oryzophilus*), *Rhabdoscelus lineaticollis*, boll weevil (*Anthonomus grandis*), nunting billbug (*Sphenophorus venatus*), southern corn billbug (*Sphenophorus callosus*), soybean stalk weevil (*Sternechus subsignatus*), sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), coffee berry borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*), and mason beetle (*Tribolium confusum*);

from the family Coccinellidae, for example, twenty-eight-spotted ladybird (*Epilachna vigintioctopunctata*);

from the family Bostrychidae, for example, common powder-post beetle (*Lyctus brunneus*);

from the family Ptinidae;

from the family Cerambycidae, for example, citrus long-horned beetle (*Anoplophora malasiaca*) and, *Migdolus fryanus*;

from the family Elateridae, for example, *Melanotus okinawensis*, barley wireworm (*Agriotes fuscicollis*), *Melanotus legatus, Anchastus* spp., *Conoderus* spp., *Ctenicera* spp., *Limonius* spp., and *Aeolus* spp.;

from the family Staphylinidae, for example, *Paederus fuscipes*;

from the family Dermestidae, for example, varied carpet beetle (*Anthrenus verbasci*) and, hide beetle (*Dermestes maculates*);

from the family Anobiidae, for example, tobacco beetle (*Lasioderma serricorne*), and biscuit beetle (*Stegobium paniceum*);

and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), brown locust (*Locustana pardalina*), tree locust (*Anacridium melanorhodon*), Italian locust (*Calliptamus italicus*), differential grasshopper (*Melanoplus differentialis*), two-striped grasshopper (*Melanoplus bivittatus*), migratory grasshopper (*Melanoplus sanguinipes*), red-legged grasshopper (*Melanoplus femurrubrum*), clear-winged grasshopper (*Camnula pellucida*), desert locust (*Schistocerca gregaria*), Yellow-winged locust (*Gastrimargus musicus*), spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryliidae, for example, house cricket (*Acheta domestica*), and emma field cricket (*Teleogryllus emma*);

from the family Tettigoniidae, for example, mormon cricket (*Anabrus simplex*);
and the others.
Hymenoptera:
from the family Tenthredinidae, for example, beet sawfly (*Athalia rosae*), and nippon cabbage sawfly (*Athalia japonica*);
from the family Formicidae, for example, *Solenopsis* spp. (such as red imported fire ant (*Solenopsis invicta*) and, tropical fire ant (*Solenopsis geminata*)), *Atta* spp. (such as brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica japonica*, *Pristomyrmex punctutus*, *Pheidole noda*, big-headed ant (*Pheidole megacephala*), *Camponotus* spp. (such as *Camponotus japonicus*, and *Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);
from the family Vespidae, for example, Asian giant hornet (*Vespa mandarinia japonica*), *Vespa simillima*, *Vespa analis Fabriciusi*, Asian hornet (*Vespa velutina*), and *Polistes jokahamae*;
from the family Siricidae, for example, pine wood wasp (*Urocerus gigas*);
from the family Bethylidae;
and the others.
Blattodea:
from the family Blattellidae, for example, German cockroach (*Blattella germanica*);
from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*);
from the family Termitidae, for example, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*; and the others.
Siphonaptera:
for example, cat flea (*Ctenocephalides felis*), dog flea (*Ctenocephalides canis*), human flea (*Pulex irritans*), oriental rat flea (*Xenopsylla cheopis*), chigoe flea (*Tunga penetrans*), chicken flea (*Echidnophaga gallinacea*), and European rat flea (*Nosopsyllus fasciatus*);
and the others.
Anoplura:
for example, pig louse (*Haematopinus suis*), short-nosed cattle louse (*Haematopinus eurysternus*), sheep biting louse (*Dalmalinia ovis*), *Linognathus seypsus*, *Pediculus humanis*, *Pediculuc humanus corporis*, *Pediculus humanus humanus*, and *Phthirus pubis*;
and the others.
Mallophagida:
for example, *Bovicola* spp. (such as cattle biting louse (*Dalmalinia bovis*) and, sheep biting louse (*Dalmalinia ovis*)), *Trichodestes* spp. (such as dog biting louse (*Trichodectes canis*)), *Felicola* spp. (such as cat louse (*Felicola subrostrata*)), *Lipeurus* spp. (such as chicken wing louse (*Lipeurus caponis*)), and Menoponidae family (such as *Trimenopon* spp. and, *Menopon* spp.);
and the others.
Acari:
from the family Tetranychidae, for example, common red spider mite (*Tetranychus urticae*), kanzawa spider mite (*Tetranychus kanzawai*), red spider mite (*Tetranychus evansi*), citrus red mile (*Panonychus citri*), fruit-tree red spider mite (*Panonychus ulmi*), and *Oligonychus* spp.;
from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, and *Shevtchenkella* sp.;
from the family Tarsonemidae, for example, broad mite (*Polyphagotarsonemus latus*);
from the family Tenuipalpidae, for example, *Brevipalpus phoenicis*;
from the family Tuckerellidae;
from the family Ixodidae, for example, *Haemaphysalis longicornis*, *Haemaphysalis flava*, *Dermacentor taiwanensis*, American dog tick (*Dermacentor variabilis*), *Dermacentor andersoni*, *Ixodes ovatus*, *Ixodes persulcatus*, *Ixodes ricinus*, black-legged tick (*Ixodes scapularis*), lone star tick (*Amblyomma americanum*), *Amblyomma maculatum*, cattle tick (*Boophilus microplus*), *Boophilus annulatus*, and brown dog tick (*Rhipicephalus sanguineus*);
from the family Acaridae, for example, cereal mite (*Tyrophagus putrescentiae*), and grassland mite (*Tyrophagus similis*);
from the family Pyroglyphidae, for example, American house dust mite (*Dermatophagoides farinae*), and European house dust mite (*Dermatophagoides pteronyssinus*);
from the family Cheyletidae, for example, *Cheyletus eruditus*, *Cheyletus malaccensis*, *Cheyletus moorei*, and *Cheyletiella yasguri*;
from the family Sarcoptidae, for example, ear mange mite (*Otodectes cynotis*), and itch mite (*Sarcoptes scabiei*);
from the family Demodicidae, for example, dog follicle mite (*Demodex canis*);
from the family Listrophoridae;
from the family Haplochthoniidae;
from the family Macronyssidae, for example, tropical rat mite (*Ornithonyssus bacoti*), and feather mite (*Ornithonyssus sylviarum*);
from the family Dermanyssidae, for example, bird mite (*Dermanyssus gallinae*);
from the family Trombiculidae, for example, *Leptotrombidium akamushi*;
and the others.
Araneae:
from the family Eutichuridae, for example, *Cheiracanthium japonicum*;
from the family Theridiidae, for example, red-back spider (*Latrodectus hasseltii*);
and the others.
Polydesmida:
from the family Paradoxosomatidae, for example, flat-backed millipede (*Oxidus gracilis*), and *Nedyopus tambanus*;
and the others.
Isopoda:
from the family Armadillidiidae, for example, common pill bug (*Armadillidium vulgare*);
and the others.

Chilopoda:
from the family Scutigeridae, for example, *Thereuonema hilgendorfi;*
from the family Scolopendridae, for example, giant tropical centipede (*Scolopendra subspinipes*);
from the family Ethopolidae, for example, *Bothropolys rugosus;*
and the others.

Gastropoda:
from the family Limacidae, for example, tree slug (*Limax marginatus*), and garden tawny slug (*Limax flavus*);
from the family Philomycidae, for example, *Meghimatium bilineatum;*
from the family Ampullariidae, for example, golden apple snail (*Pomacea canaliculata*);
from the family Lymnaeidae, for example, *Austropeplea ollula;*
and the others.

Nematoda:
from the family Aphelenchoididae, for example, rice white-tip nematode (*Aphelenchoides besseyi*);
from the family Pratylenchidae, for example, root lesion nematode (*Pratylenchus coffeae*), *Pratylenchus brachyurus*, California meadow nematode (*Pratylenchus neglectus*), and *Radopholus similis;*
from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);
from the family Hoplolaimidae, for example, *Rotylenchulus reniformis;*
from the family Anguinidae, for example, strawberry bud nematode (*Nothotylenchus acris*), and stem nematode (*Ditylenchus dipsaci*);
from the family Tylenchulidae, for example, citrus nematode (*Tylenchulus semipenetrans*);
from the family Longidoridae, for example, dagger nematode (*Xiphinema index*);
from the family Trichodoridae;
from the family Parasitaphelenchidae, for example, pine wilt disease (*Bursaphelenchus xylophilus*);
and the others.

The target harmful insects and harmful mites may have a reduced agent-sensitivity to or a developed agent-resistance to an insecticide or a miticide. However, when the agent-sensitivity is greatly reduced or the agent-resistance is greatly developed, a composition of the present invention comprising an insecticide and a miticide other than the intended insecticide and miticide is preferably used.

The Present compound may be also used to protect a plant from a plant disease caused by insect-borne viruses or insect-borne bacteria.

Examples of the insect-borne viruses are recited as follows.

Rice tungro spherical virus, Rice tungro baciliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, *Chrysanthemum* stem necrosis virus, Impatiens necrotic spot virus, Iris yellow spot virus, Lily mottle cirus, Lilly symptomless virus, Tulip mosaic virus, and the others.

Examples of the insect-borne bacteria are recited as follows.

Candidatus Phytoplasma oryzae, Candidatus Phytoplasma asteris, Maize bushy stunt phytoplasma, Candidatus Liberbacter asiaticus, Candidatus Liberbacter africanus, Candidatus Liberbacter americanus, and the others.

The composition for controlling harmful arthropods of the present invention comprises the compound of the present invention or the composition A and an inert carrier (hereinafter, referred to as Composition of the present invention or Present composition). The composition for controlling harmful arthropods of the present invention is usually prepared by mixing the compound of the present invention or the composition A with an inert carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, and tablets and the others. Such formulations may be processed into mosquito repellent coils, electric mosquito repellent mats, liquid mosquito formulations, smoking agents, fumigants, sheet formulations, spot-on formulations or formulations for oral treatment. The composition for controlling harmful arthropods of the present invention comprises usually 0.01 to 95% by weight of the compound of the present invention.

Examples of the solid carrier to be used in the formulation include fine powders or granules of clays (for example, kaolin clay, diatomaceous earth, bentonite, Fubasami clay, or acid white clay), dry silica, wet silica, hydrated silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl etheR14-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseed oil).

Examples of gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is carried out by applying an effective amount of the compound of the present invention or the composition of the present invention to a harmful arthropod directly and/or a habitat thereof (for example, plant bodies, soil, an interior of a house, animal bodies). Also, the method for controlling harmful arthropods of the present invention can be applied to seeds. In the method for controlling harmful arthropods of the present invention, the compound of the present invention is usually applied in a form of the composition for controlling harmful arthropods of the present invention.

When a composition for controlling harmful arthropods of the present invention is used for controlling harmful arthropods in an agricultural field, the application dose as an amount of the compound of the present invention is usually within a range from 1 to 10,000 g per 10,000 m$^2$. In the case of being applied to seeds, the effective amount of the compound of the present invention is within a range of usually 0.001 to 100 g per 1 Kg seeds. When the composition for controlling harmful arthropods of the present invention is formulated into emulsifiable concentrate, wettable powder, or flowable formulation, the composition of the present invention is usually applied by diluting it with water in such a way that a concentration of the active ingredient is within a range from 0.01 to 10,000 ppm. The granular formulation, or the dust formulation etc., is usually applied as itself without diluting it.

These formulations or an aqueous dilution thereof may be sparged directly to harmful arthropods or plants such crops to be protected from harmful arthropods, and also may be applied to the soil of crop land in order to control harmful arthropods which live in soil of the crop land.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the composition for controlling harmful arthropods of the present invention is used to control harmful arthropods that live inside a house, the application dose as an amount of the compound of the present invention is usually within a range from 0.01 to 1,000 mg per 1 m$^2$ of an area to be treated, in the case of using it on a planar area. In the case of using it spatially, the application dose as an amount of the compound of the present invention is usually within a range from 0.01 to 500 mg per 1 m$^3$ of the space to be treated. When the composition for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm. In the case of being formulated into oil solutions, aerosols, smoking agents, poison baits and the others, such formulations are used as itself without diluting it.

When the composition of the present invention is used for controlling external parasites of livestock such as cows, horses, pigs, sheep, goats and chickens and small animals such as dogs, cats, rats and mice, the composition of the present invention may be applied to the animals by a known method in the veterinary field. Specifically, when systemic control is intended, the composition of the present invention is administered to the animals as a tablet, a mixture with feed or a suppository, or by injection (including intramuscular, subcutaneous, intravenous and intraperitoneal injections). On the other hand, when non-systemic control is intended, the composition of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of being administered to an animal body, the dose of the compound of the present invention is usually within a range from 0.1 to 1,000 mg per 1 kg of an animal body weight.

Also, the composition of the present invention may be used as an agent for controlling harmful arthropods in agricultural lands such as paddy fields, fields, turfs, and orchards. The compound of the present invention or the composition of the present invention may be controlled the harmful arthropods where lives in agricultural lands where the following plants etc., are grown.

Crops:
  corn, rice, wheat, barley, rye, oat, sorghum, cotton, soybean, peanut, buckwheat, beet, rapeseed, sunflower, sugar cane, tobacco, and the others; Vegetables:
  solanaceous vegetables (for example, eggplant, tomato, pimento, pepper, or potato),
  cucurbitaceous vegetables (for example, cucumber, pumpkin, zucchini, water melon, or melon),
  cruciferous vegetables (for example, Japanese radish, white turnip, horseradish, kohlrabi, Chinese cabbage, cabbage, leaf mustard, broccoli, or cauliflower),
  asteraceous vegetables (for example, burdock, crown daisy, artichoke, or lettuce),
  liliaceous vegetables (for example, green onion, onion, garlic, or asparagus),
  ammiaceous vegetables (for example, carrot, parsley, celery, or parsnip),
  chenopodiaceous vegetables (for example, spinach, or Swiss chard),
  lamiaceous vegetables (for example, *Perilla frutescens*, mint, or basil),
  strawberry, sweet potato, *Dioscorea japonica*, colocasia, or the others;
Flowers:
  Ornamental foliage plants:
  Lawn:
Fruits:
  pomaceous fruits (for example, apple, pear, Japanese pear, Chinese quince, or quince),
  stone fleshy fruits (for example, peach, plum, nectarine, *Prunus mume*, cherry fruit, apricot, or prune),
  citrus fruits (for example, *Citrus unshiu*, orange, lemon, lime, or grapefruit),
  nuts (for example, chestnut, walnuts, hazelnuts, almond, pistachio, cashew nuts, or macadamia nuts),
berry fruits (for example, blueberry, cranberry, blackberry or raspberry),
  grapes, kaki persimmon, olive, Japanese plum, banana, coffee, date palm, coconuts, and the others;
Trees other than fruit trees:
  tea, mulberry, flowering plant, roadside trees (for example, ash, birch, dogwood, *Eucalyptus, Ginkgo biloba*, lilac, maple, Quercus, poplar, Judas tree, *Liquidambar formosana*, plane tree, zelkova, *Japanese arborvitae*, fir wood, hemlock, juniper, *Pinus, Picea*, and *Taxus cuspidate*); and the others.

The above-described plants may be genetically modified crops.

EXAMPLES

Hereinafter, the present invention is explained in more detail by using Preparation Examples, Reference Preparation Examples, Formulation Examples, and Test Examples, however, the present invention should not be limited to these examples.

First, the preparation examples of the compound of the present invention are described.

Reference Preparation Example 1

To a mixture of 6-methoxypyrimidine-4-carboxylic acid 8.97 g, N,O-dimethylhydroxylamine hydrochloride salt 6.24 g, and acetonitrile 250 mL were added 1-ethyl-3-(3-dimethylaminopropyl)carbodiimide hydrochloride salt 13.4 g, 1-hydroxybenzotriazole 0.79 g, and triethylamine 9.7 ml successively at room temperature, and the mixture was stirred at room temperature for 1 hour. Water was added to the resulting mixture, and the mixture was extracted with ethyl acetate. The resulting organic layers were washed with water and saturated brine successively, dried over anhydrous sodium sulfate, and concentrated under reduced pressure. The residues were subjected to a silica gel column chromatography to obtain an intermediate compound represented by the following formula 9.59 g.

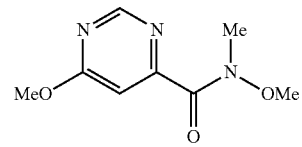 [SMILES: COc1cc(C(=O)N(C)OC)ncn1]

Intermediate compound 1: $^1$H-NMR (CDCl$_3$) δ: 8.80 (1H, d), 6.98 (1H, d), 4.02 (3H, s), 3.74 (3H, s), 3.37 (3H, s).

Reference Preparation Example 2

To a mixture of the intermediate compound 1 9.03 g and THF 150 mL was added methyl magnesium bromide (IM, THF solution) 50 mL under ice-cooling, and the mixture was stirred at room temperature for 2 hours. To the resulting mixture was added 1N hydrochloric acid, and the mixture was extracted with ethyl acetate. The resulting organic layer was washed with water and saturated brine successively, dried over anhydrous sodium sulfate, and concentrated under reduced pressure. The resulting residues were subjected to a silica gel column chromatography to obtain an intermediate compound 2 represented by the following formula 2 4.99 g.

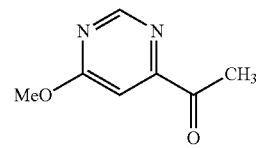

Intermediate compound 2: $^1$H-NMR (CDCl$_3$) δ: 8.89 (1H, d), 7.31 (1H, d), 4.03 (3H, s), 2.69 (3H, s).

Reference Preparation Example 3

To a mixture of the intermediate compound 2 4.99 g and THF 150 mL was added trimethyl phenyl ammonium tribromide 13.6 g, and the mixture was stirred under reflux for 8 hours. Water was added to the resulting mixture, and the mixture was extracted with MTBE. The resulting organic layers were washed with water and saturated brine successively, dried over anhydrous sodium sulfate, and concentrated under reduced pressure. The resulting residues were subjected to a silica gel chromatography to obtain an intermediate compound 3 represented by the following formula 4.44 g.

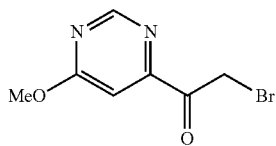

Intermediate compound 3: $^1$H-NMR (CDCl$_3$) δ: 8.89 (1H, d), 7.37 (1H, d), 4.74 (2H, s), 4.05 (3H, s).

Reference Preparation Example 4

To a mixture of the intermediate compound 3 4.44 g and ethanol 30 mL was added 5-(trifluoroethyl)-2-aminopyridine 3.4 g at room temperature, and the mixture was stirred under reflux for 9 hours. Water was added to the resulting mixture, and the mixture was extracted with ethyl acetate. The resulting organic layers were dried over sodium sulfate, and concentrated under reduced pressure. The resulting residues were subjected to a silica gel chromatography to obtain an intermediate compound 4 represented by the following formula 3.05 g.

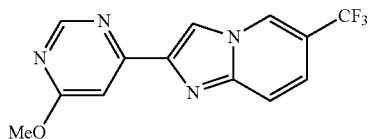 [SMILES: COc1cc(-c2cn3cc(C(F)(F)F)ccc3n2)ncn1]

Intermediate compound 4: $^1$H-NMR (CDCl$_3$) δ: 8.80 (1H, d), 8.54-8.53 (1H, m), 8.40 (1H, d), 7.75 (1H, dd), 7.55 (1H, d, J=1.1 Hz), 7.38 (1H, dd), 4.05 (3H, s).

Reference Preparation Example 5

The mixture of the intermediate compound 4 3.05 g, N-iodosuccinimide 2.45 g, and DMF 20 mL was stirred at 70° C. for 6 hours. An aqueous sodium thiosulfate solution was added to the resulting mixture, and the resulting solids were collected by filtration, and dried under reduced pressure to obtain the intermediate compound 5 represented by the following formula 3.45 g.

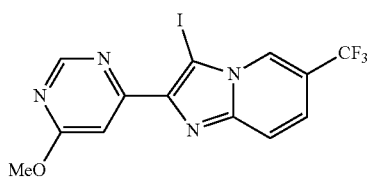 [SMILES: COc1cc(-c2nc3ccc(C(F)(F)F)cn3c2I)ncn1]

Intermediate compound 5: $^1$H-NMR (CDCl$_3$) δ: 8.92 (1H, s), 8.70 (1H, s), 7.75 (1H, d), 7.64 (1H, d), 7.46 (1H, dd), 4.06 (3H, s).

Reference Preparation Example 6

The mixture of the intermediate compound 5 3.45 g, tris(dibenzylideneacetone)dipalladium(0) 0.38 g, Xantphos 0.48 g, diisopropylethylamine 4.22 mL, ethanethiol 0.93 mL and 1,4-dioxane 40 mL was stirred under reflux for 6 hours. Water was added to the resulting mixture, and the mixture was extracted with MTBE. The resulting organic layers were dried over sodium sulfate, and concentrated under reduced pressure. The resulting residues were subjected to a silica gel chromatography to obtain an intermediate compound 6 represented by the following formula 3.78 g.

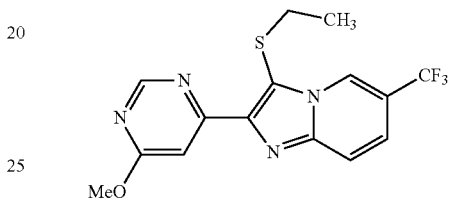

Intermediate compound 6: $^1$H-NMR (CDCl$_3$) δ: 8.96 (1H, d), 8.95 (1H, dd), 7.82 (1H, dd), 7.80 (1H, dd), 7.46 (1H, dd), 4.06 (3H, s), 2.94 (2H, q), 1.18 (3H, t).

Reference Preparation Example 7

A mixture of the intermediate compound 6 3.78 g, concentrated hydrochloric acid 20 mL and THF 5 mL was stirred at 60° C. for 3 hours. The resulting mixture was stood to cool to room temperature, and the mixture was then neutralized with saturated aqueous sodium hydrogen carbonate. The resulting solids were collected by filtration, and dried under reduced pressure to obtain an intermediate compound 7 represented by the following formula 3.55 g.

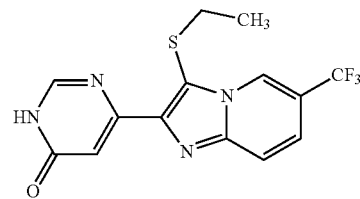 [SMILES: CCSc1c(-c2cc(=O)[nH]cn2)nc2ccc(C(F)(F)F)cn12]

Intermediate compound 7: $^1$H-NMR (DMSO-d$_6$) δ: 8.99 (1H, dd), 8.34 (1H, d), 7.91 (1H, d), 7.69 (1H, dd), 7.05 (1H, d), 2.97 (2H, q), 1.06 (3H, t).

Preparation Example 1

A mixture of the intermediate compound 7 800 mg, cesium carbonate 840 mg, and 2,2,3,4,4,4-hexafluorobutyl=trifluoromethanesulfonate 810 mg, and DMF 4 mL was stirred at 70° C. for 5 hours. The resulting mixture was stood to cool to room temperature, and water was then added thereto, and the mixture was extracted with MTBE. The resulting organic layers were washed with saturated brine, dried over anhydrous sodium sulfate, and concentrated under reduced pressure. The resulting residues were subjected to a silica gel chromatography (hexane:ethyl acetate 2:1) to obtain a present compound 1 represented by the following formula 300 mg.

Present compound 1: $^1$H-NMR (CDCl$_3$) δ: 8.97 (1H, d), 8.96-8.95 (1H, m), 7.92 (1H, d), 7.80 (1H, d), 7.48 (1H, dd), 5.23-5.04 (1H, m), 4.90-4.83 (2H, m), 2.98 (2H, q), 1.19 (3H, t).

Preparation Example 2

The compound which was prepared according to the Preparation Example 1 and its physical property value was shown below.
A compound represented by formula (A-1):

(A-1)

wherein a combination of T, R$^2$, G$^1$, G$^2$, G$^3$ and G4 represents any combinations indicated in Table 16.

TABLE 16

| Present compound | T | R$^2$ | G$^1$ | G$^2$ | G$^3$ | G$^4$ |
|---|---|---|---|---|---|---|
| 2 | CH$_2$CF$_2$CF$_3$ | Et | CH | CCF$_3$ | CH | CH |
| 3 | CH$_2$CF$_2$CF$_2$CF$_3$ | Et | CH | CCF$_3$ | CH | CH |
| 4 | CH$_2$CF$_2$CHF$_3$ | Et | CH | CCF$_3$ | CH | CH |

Present compound 2: $^1$H-NMR (CDCl$_3$) δ: 8.97 (1H, d), 8.96-8.95 (1H, m), 7.94 (1H, d, J=1.1 Hz), 7.80 (1H, d), 7.48 (1H, dd), 4.97 (2H, t), 2.97 (2H, q), 1.19 (3H, t).
Present compound 3: $^1$H-NMR (CDCl$_3$) δ: 8.91 (1H, s), 8.28 (1H, s), 7.81 (1H, d), 7.72 (1H, d), 7.48 (1H, dd), 4.74 (2H, t), 2.89 (2H, q), 1.21 (3H, t).
Present compound 4: $^1$H-NMR (CDCl$_3$) δ: 8.92 (1H, dd), 8.29 (1H, d), 7.81 (1H, d), 7.70 (1H, d), 7.48 (1H, dd), 5.98 (1H, tt), 4.62 (2H, t), 2.89 (2H, q), 1.21 (3H, t).

Preparation Example 3

To a mixture of the present compound 1 300 mg and chloroform 20 mL was added mCPBA (purity 70%) 0.31 g under ice-cooling, and the mixture was stirred at room temperature for 6 hours. To the resulting mixture were added saturated aqueous solution of sodium hydrogen carbonate and then an aqueous solution of sodium thiosulfate, and the mixture was extracted with chloroform. The resulting organic layers were dried over sodium sulfate, and concentrated under reduced pressure. The resulting residues were subjected to silica gel chromatography (hexane:ethyl acetate=2:1) to a present compound 5 represented by the following formula 0.31 g.

Present compound 5: $^1$H-NMR (CDCl$_3$) δ: 9.62 (1H, s), 8.21 (1H, s), 7.88 (1H, d), 7.65 (1H, dd), 7.31 (1H, d), 5.14-5.00 (1H, m), 4.74-4.50 (2H, m), 3.90 (2H, q), 1.42 (3H, t).

Preparation Example 4

The compound which was prepared according to the Preparation Example 3 and its physical property value was shown below.
A compound represented by formula (A-2):

(A-2)

wherein a combination of T, R$^2$, G$^1$, G$^2$, G$^3$ and G4 represents any combinations indicated in Table 17.

TABLE 17

| Present compound | T | R$^2$ | G$^1$ | G$^2$ | G$^3$ | G$^4$ |
|---|---|---|---|---|---|---|
| 6 | CH$_2$CF$_2$CF$_3$ | Et | CH | CCF$_3$ | CH | CH |
| 7 | CH$_2$CF$_2$CF$_2$CF$_3$ | Et | CH | CCF$_3$ | CH | CH |
| 8 | CH$_2$CF$_2$CHF$_3$ | Et | CH | CCF$_3$ | CH | CH |

Present compound 6: $^1$H-NMR (CDCl$_3$) δ: 9.61 (1H, s), 8.20 (1H, d), 7.88 (1H, d), 7.65 (1H, dd), 7.31 (1H, s), 4.68 (2H, t), 3.90 (2H, q), 1.42 (3H, t).
Present compound 7: $^1$H-NMR (CDCl$_3$) δ: 9.61 (1H, d), 8.20 (1H, d), 7.88 (1H, t), 7.65 (1H, dd), 7.31 (1H, d), 4.72 (2H, t), 3.89 (2H, q), 1.42 (3H, t).
Present compound 8: $^1$H-NMR (CDCl$_3$) δ: 9.62 (1H, dd), 8.21 (1H, d), 7.88 (1H, d), 7.65 (1H, dd), 7.30 (1H, d), 5.97 (1H, tt), 4.60 (2H, t), 3.90 (2H, q), 1.42 (3H, t).
Next, the formulation Examples of the Present compound is described. The "parts" represents "part by weight" unless otherwise specified.

Formulation Example 1

Into a mixture of 35 parts of xylene and 35 parts of DMF, 10 parts of any one of the Present compounds 1 to 8 is added, followed by mixing, and then 14 parts of polyoxyethylene styryl phenyl ether and 6 parts of calcium dodecylbenzene sulfonate are added thereto, followed by mixing them to obtain each formulation.

Formulation Example 2

Four (4) parts of sodium lauryl sulfate, 2 parts of calcium lignin sulfonate, 20 parts of synthetic hydrated silicon oxide fine powder, and 54 parts of diatomaceous earth are mixed, and further 20 parts of any one of the Present compounds 1 to 8 is added, followed by mixing them to obtain each formulation.

Formulation Example 3

To 2 parts of any one of the Present compounds 1 to 65, 1 part of synthetic hydrated silicon oxide fine powder, 2 parts of calcium lignin sulfonate, 30 parts of bentonite and 8 parts of kaolin clay are added, followed by mixing. Then the mixtures are stirred, granulated with a granulator, and forced-air dried to obtain each formulation.

Formulation Example 4

Into an appropriate amount of acetone, 1 part of any one of the Present compounds 1 to 8 is added, followed by mixing, and then 5 parts of hydrous silica, 0.3 parts of isopropyl acid phosphate, and 93.7 parts of kaolin clay are added, followed by mixing with stirring thoroughly and removal of acetone from the mixtures by evaporation to obtain each formulation.

Formulation Example 5

Thirty five (35) parts of a mixture of polyoxyethylene alkyl ether sulfate ammonium salt and hydrous silica (weight ratio of 1:1), 20 parts of any one of the Present compounds 1 to 8, and 45 parts of water are mixed thoroughly to obtain each formulation.

Formulation Example 6

Into a mixture of 5 parts of xylene and 5 parts of trichloroethane, 0.1 parts of any one of the Present compounds 1 to 8 is added, followed by mixing, and the resulting mixture is then mixed with 89.9 parts of kerosene to obtain each formulation.

Formulation Example 7

Into 0.5 mL of acetone, 10 mg of any one of the Present compounds 1 to 8 is added, followed by mixing, and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the Present compounds 1 to 8 and 49.9 parts of Neothiozole (Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 part of any one of the Present compounds 1 to 8, 0.01 part of BHT (2,6-di-tert-butyl-4-methylphenol), 5 parts of xylene, 3.39 parts of deodorized kerosene and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain each aqueous aerosol.

Formulation Example 10

Zero point one (0.1) parts of any one of the Present compounds 1 to 8 are mixed into 2 mL of propylene glycol, and the resulting solution is impregnated into a ceramic plate having a size of 4.0 cm×4.0 cm and a thickness of 1.2 cm, to obtain each thermal fumigant.

Formulation Example 11

Five (5) parts of any one of the Present compounds 1 to 8, and 95 parts of ethylene-methyl methacrylate copolymer (the ratio of the methyl methacrylate in the copolymer:10 weight %), Acryft (registered by trademark) WD 301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding die to obtain each rod-shaped molded product having a length of 15 cm and a diameter of 3 mm.

Formulation Example 12

Five (5) parts of any one of the Present compounds 1 to 8, and 95 parts of plasticized polyvinyl chloride resin are melted and kneaded with a closed type pressure kneader (manufactured by Moriyama Manufacturing Co. Ltd.), and the resulting kneaded product is extruded from an extrusion molding machine through a molding die to obtain each rod-shaped molded product having a length of 15 cm and a diameter of 3 mm.

Formulation Example 13

One hundred (100) mg of any one of the Present compounds 1 to 8, 68.75 mg of lactose, 237.5 mg of corn starch, 43.75 mg of microcrystalline cellulose, 18.75 mg of polyvinylpyrrolidone, 28.75 mg of sodium carbomethyl starch and 2.5 mg of magnesium stearate are mixed, and the resulting mixture was compressed to an appropriate size to obtain each tablet.

Formulation Example 14

Twenty five (25) mg of any one of the Present compounds 1 to 8, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain each capsule.

Formulation Example 15

To 100 mg of any one of the Present compounds 1 to 8, 500 mg of fumaric acid, 2,000 mg of sodium chloride, 150 mg of methyl paraben, 50 mg of propyl paraben, 25,000 mg of granulated sugar, 13,000 mg of sorbitol (70% solution), 100 mg of Veegum K (manufactured by Vanderbilt Co.), 35 mg of perfume and 500 mg of coloring agent, a distilled water is added so that a final volume is set to be 100 mL, followed by mixing them to obtain each suspension for oral administration.

Formulation Example 16

Into a mixture of 5% by weight of an emulsifier, 3% by weight of benzyl alcohol and 30% by weight of propylene glycol, 5% by weight of any one of the Present compounds 1 to 8 is dissolved, and phosphate buffer is added thereto so that a pH of the solution is set to be 6.0 to 6.5, and water is added as the rest parts to obtain each solution for oral administration.

Formulation Example 17

To a mixture of 57% by weight of fractional distillated palm oil and 3% by weight of polysorbate 85, 5% by weight of aluminum distearate is added, and heated to disperse it. The resulting mixture is cooled to room temperature, and 25% by weight of saccharin is dispersed in an oil vehicle. Ten (10) % by weight of any one of the Present compounds 1 to 8 is divided thereto to obtain each paste for oral administration.

Formulation Example 18

Five (5) % by weight of any one of the Present compounds 1 to 8 is mixed with 95% by weight of limestone filler, followed by a wet granulation of the resulting mixture to obtain each granule for oral administration.

Formulation Example 19

Into 80 parts of diethylene glycol monomethyl ether, 5 parts of any one of the Present compounds 1 to 8 is dissolved, and 15 parts of propylene carbonate is added thereto, and the resulting mixture is mixed to obtain each spot-on solution.

Formulation Example 20

Into 70 parts of diethylene glycol monomethyl ether, 10 parts of any one of the Present compounds 1 to 8 is dissolved, and 20 parts of 2-octyldodecanol is added thereto, and the resulting mixture is mixed to obtain a pour-on solution.

Formulation Example 21

To 0.5 parts of any one of the Present compounds 1 to 8, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain each hydrogenous solution of shampoo formulation.

Formulation Example 22

Zero point one five (0.15)% by weight of any one of the Present compounds 1 to 8, 95% by weight of animal feed, as well as 4.85% by weight of a mixture of dibasic calcium phosphate, diatomaceous earth, aerosol and carbonate (or chalk) are mixed with stirring thoroughly to obtain each premix for animal feed.

Formulation Example 23

Seven point two (7.2) g of any one of the Present compounds 1 to 8, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain each suppository.

Next, Test Examples are used to show an efficacy of the Present compound on controlling harmful arthropods.

The following test examples were carried out at 25° C.

Test Example 1

The test compounds is made to a formulation according to a similar method to that described in the Formulation Example 5, and thereto is added water containing 0.03 v/v % of shindain (registered trademark) to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all stages of life) are released onto the leaves of the cucumber. After 1 day, the diluted solutions are sprayed into the seedling in a ratio of 10 mL/seedling. Further, after 5 days, the number of the surviving insects is examined and the controlling value is calculated by the following equation.

Controlling value (%)=$\{1-(Cb \times Tai)/(Cai \times Tb)\} \times 100$ wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

The test was conducted by making the prescribed concentration 500 ppm and using the below-mentioned Present compounds as a test compound according to the test example 1. As a result of the test, the below-mentioned Present compounds showed 90% or greater as the controlling value.

Present compound number: Present compounds 5 to 8.

Test Example 2

The test compounds are made to a formulation according to a similar method to that described in the Formulation Example 5, and thereto is added water to prepare a diluted solution containing a prescribed concentration of the test compound.

Cucumber seedling (on the developmental stage of the second true leaf) is planted in a container, and the diluted solutions are irrigated into the plant foot in the ratio of 5 mL/seedling. After 7 days, approximately 30 cotton aphids (*Aphis gossypii*) (all stages of life) are inoculated onto the cucumber leaves. Further, after additional 6 days, the number of the surviving insects is examined, and the controlling value is calculated by the following equation.

$$\text{Controlling value (\%)} = \{1-(Cb \times Tai)/(Cai \times Tb)\} \times 100$$

wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

The test was conducted by making the prescribed concentration 1,000 ppm and using the below-mentioned Present compounds as a test compound according to the test example 2. As a result of the test, the below-mentioned Present compounds showed 90% or greater as the controlling value.

Present compound number: Present compounds 5 and 6.

Test Example 3

The test compounds are made to a formulation according to a similar method to that described in the Formulation Example 5, and thereto is added water containing 0.03 v/v % of shindain (registered trademark) to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mL/seedling. Thereafter, the stem and leaf thereof is cut out and then is installed into the container that is covered with the filter paper. Five common cutworms (*Spodoptera litura*) at the second instar larval stages are released into the cup. After 5 days, the surviving insects are counted, and the mortality of insects is calculated by the following equation.

$$\text{Morality (\%)} = \{1-\text{Number of the surviving insects}/5\} \times 100$$

The test was conducted by making the prescribed concentration 500 ppm and using the below-mentioned Present compounds as a test compound according to the test example 3. As a result of the test, the below-mentioned Present compounds showed 80% or greater as the morality.

Present compound number: Present compounds 5 to 8.

Test Example 4

The test compounds are made to a formulation according to a similar method to that described in the Formulation Example 5, and thereto is added water containing 0.03 v/v % of shindain (registered trademark) to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mL/seedling. Thereafter, the stem and leaf thereof is cut out and then is installed into the container that is covered with the filter paper. Five cabbage moths (*Plutella xylostella*) at the second instar larval stages are released into the cup. After 5 days, the surviving insects are counted, and the mortality of insects is calculated by the following equation.

$$\text{Morality (\%)} = \{1-\text{Number of the surviving insects}/5\} \times 100$$

The test was conducted by making the prescribed concentration 500 ppm and using the below-mentioned Present compounds as a test compound according to the Test Example 4. As a result of the test, the below-mentioned Present compounds showed 80% or greater as the morality.

Present compound number: Present compounds 2 to 8.

Test Example 5

The test compounds are dissolved into a mixed solution of polyoxyethylene sorbitan mono-cocoate and acetone (acetone and polyoxyethylene sorbitan mono-cocoate=5:95 (v/v ratio)) in a ratio of 50 µL of the mixed solution per 1 mg of the test compound. Thereto is added water containing 0.03% by volume of shindain (registered trademark) to prepare a diluted solution containing a prescribed concentration of the test compound.

The young seedling Corns (*Zea mays*) are immersed into the diluted solution for 30 seconds. Thereafter, two grains of the seedling are installed in a plastic petri dish (90 mm radius), and 10 western corn rootworms (*Diabrotica virgifera virgifera*) at the second instar larval stages are released onto the container. After 5 days, the number of the died insects are counted and the mortality of insects is calculated by the following equation.

$$\text{Morality (\%)} = (\text{Number of the died insects}/10) \times 100$$

The test was conducted by making the prescribed concentration 500 ppm and using the below-mentioned Present compounds as a test compound according to the Test Example 5. As a result of the test, the below-mentioned Present compounds showed 80% or greater as the morality.

Present compound number: Present compounds 2 and 5 to 8.

Test Example 6

The test compounds are made to a formulation according to a similar method to that described in the Formulation Example 5, and thereto is added water to prepare a diluted solution containing a prescribed concentration of the test compound.

A filter paper having a diameter of 5.5 cm was spread on the bottom of a polyethylene cup having a diameter of 5.5 cm, and each test solution (0.7 ml) was added dropwise onto the filter paper. As a bait sucrose (30 mg) was uniformly placed on the filter paper. Into the polyethylene cup, 10 female imagoes of housefly (*Musca domestica*) were released and the cup was sealed with a lid. After 24 hours, the number of died houseflies are counted and the mortality of insects is calculated by the following equation.

$$\text{Morality (\%)} = (\text{Number of the died insects}/\text{the number of the tested insects}) \times 100$$

The test was conducted by making the prescribed concentration 500 ppm and using the below-mentioned Present compounds as a test compound according to the Test Example 6. As a result of the test, the below-mentioned Present compounds showed 100% as the morality.

Present compound number:Present compounds 2 and 5.

Test Example 7

The test compounds are made to a formulation according to a similar method to that described in the Formulation Example 5, and thereto is added water to prepare a diluted solution containing a prescribed concentration of the test compound.

A filter paper having a diameter of 5.5 cm was spread on the bottom of a polyethylene cup having a diameter of 5.5 cm, and each test solution (0.7 ml) was added dropwise onto the filter paper. As a bait sucrose (30 mg) was uniformly placed on the filter paper. Into the polyethylene cup, 2 male imagoes of German cockroach (*Blattella germanica*) were released and the cup was sealed with a lid. After 6 days, the number of died cockroaches are counted and the mortality of insects is calculated by the following equation.

Morality (%)=(Number of the died insects/the number of the tested insects)×100

The test was conducted by making the prescribed concentration 500 ppm and using the below-mentioned Present compounds as a test compound according to the Test Example 7. As a result of the test, the below-mentioned Present compounds showed 100% as the morality.

Present compound number:Present compounds 2, 6 and 8.

INDUSTRIAL APPLICABILITY

The Present compound shows an excellent control effect against a harmful arthropod.

The invention claimed is:

1. A compound represented by formula (I):

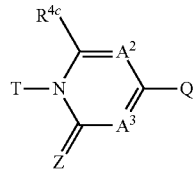

wherein

Q represents a group represented by formula Q1,

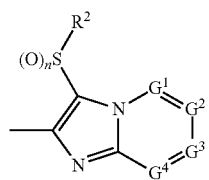

n is 0, 1 or 2, $G^1$ represents $CR^{3a}$, $G^2$ represents $CR^{3b}$, $G^3$ represents $CR^{3c}$, $G^4$ represents $CR^{3d}$, $R^{3a}$, $R^{3b}$, $R^{3c}$ and $R^{3d}$ are identical to or different from each other and each represents a C1-C6 chain hydrocarbon group optionally having one or more halogen atoms, or a hydrogen atom, $A^2$ represents a nitrogen atom, $A^3$ represents $CR^{4b}$, $R^{4b}$ represents a hydrogen atom, $R^{4c}$ represents a C1-C6 chain hydrocarbon group optionally having one or more halogen atoms, or a hydrogen atom, Z represents an oxygen atom, T represents a C2-C10 chain hydrocarbon group having one or more halogen atoms, $R^2$ represents a C1-C6 alkyl group optionally having one or more halogen atoms, a cyclopropyl group, or a cyclopropylmethyl group.

2. The compound according to claim 1 wherein T represents a C2-C10 alkyl group having three or more fluorine atoms.

3. The compound according to claim 1 wherein $G^1$ represents CH, $G^2$ represents $CR^{3b}$, $G^3$ represents $CR^{3c}$, $G^4$ represents CH, $R^{3b}$ and $R^{3c}$ are identical to or different from each other and each represents a C1-C6 alkyl group which may have optionally one or more halogen atoms, or a hydrogen atom, and $R^{4c}$ represents a hydrogen atom.

4. The compound according to claim 1 wherein $G^1$ represents CH, $G^2$ represents $CR^{3b}$, $G^3$ represents $CR^{3c}$, $G^4$ represents CH, and $R^{3b}$ and $R^{3c}$ each independently represents a C1-C6 alkyl group optionally having one or more halogen atoms, or a hydrogen atom.

5. The compound according to claim 1 wherein $R^2$ represents an ethyl group.

6. A composition for controlling harmful arthropod which comprises the compound according to claim 1 and an inert carrier.

7. A method for controlling harmful arthropod which comprises applying a composition comprising an effective amount of the compound according to claim 1 to a harmful arthropod or a habitat where a harmful arthropod lives.

8. A composition comprising the compound according to claim 1 and one or more ingredients selected from the group consisting of the following Groups (a) and (b):

Group (a): a group consisting of insecticidal ingredients, miticidal ingredients, and nematicidal ingredients; and Group (b): fungicidal ingredients.

* * * * *